(12) United States Patent
Saito et al.

(10) Patent No.: US 12,038,650 B2
(45) Date of Patent: Jul. 16, 2024

(54) MULTILAYER PHASE DIFFERENCE PLATE, POLARIZING PLATE, AND IMAGE DISPLAY DEVICE

(71) Applicant: ZEON CORPORATION, Tokyo (JP)

(72) Inventors: Masakazu Saito, Tokyo (JP); Kazuhiro Osato, Tokyo (JP); Masashi Aimatsu, Tokyo (JP); Kei Sakamoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 99 days.

(21) Appl. No.: 17/651,810

(22) Filed: Feb. 21, 2022

(65) Prior Publication Data

US 2022/0177419 A1    Jun. 9, 2022

Related U.S. Application Data

(62) Division of application No. 16/493,029, filed as application No. PCT/JP2018/010646 on Mar. 16, 2018, now abandoned.

(30) Foreign Application Priority Data

Mar. 28, 2017    (JP) .................................. 2017-063958

(51) Int. Cl.
*G02F 1/13363* (2006.01)
*B29D 11/00* (2006.01)
(Continued)

(52) U.S. Cl.
CPC .... *G02F 1/13363* (2013.01); *B29D 11/00644* (2013.01); *C07C 251/88* (2013.01);
(Continued)

(58) Field of Classification Search
CPC .......... G02F 1/13363; G02F 1/133634; G02F 1/133637; G02F 1/133638
(Continued)

(56) References Cited

U.S. PATENT DOCUMENTS 6,362,862 B1 * 3/2002 Itoh ...................... H04N 9/3105
349/5
9,207,360 B2    12/2015 Sakamoto et al.
(Continued)

FOREIGN PATENT DOCUMENTS

JP    2000147260 A    5/2000
JP    2002321302 A    11/2002
(Continued)

OTHER PUBLICATIONS

Jun. 12, 2018, International Search Report issued in the International Patent Application No. PCT/JP2018/010646.
(Continued)

*Primary Examiner* — Dung T Nguyen
*Assistant Examiner* — David Y Chung
(74) *Attorney, Agent, or Firm* — KENJA IP LAW PC

(57) ABSTRACT

A phase difference plate includes a phase difference plate P1 and a phase difference plate P2. An in-plane slow axis of the phase difference plate P1 is orthogonal to an in-plane slow axis of the phase difference plate P2. The phase difference plate P2 includes a layer of a liquid crystal material oriented in an in-plane direction. An in-plane retardation $\text{ReP2}(\lambda)$ at a wavelength $\lambda$ nm of the phase difference plate P2 satisfies the following formulae (e1) and (e2): $\{\text{Re2}(400)-\text{Re2}(550)\}/\{\text{Re2}(550)-\text{Re2}(700)\}<2.90$ (e1), and $\text{Re2}(400)/\text{Re2}(700)>1.13$ (e2). An in-plane retardation $\text{ReP1}(\lambda)$ of the phase difference plate P1 at a wavelength $\lambda$ nm and the in-plane retardation $\text{ReP2}(\lambda)$ of the phase difference plate P2 at the wavelength $\lambda$ nm satisfy the following formulae (e4) and (e5): $\text{ReP1}(550)>\text{ReP2}(550)$ (e4), and $\text{ReP1}(400)/\text{ReP1}(700)<\text{ReP2}(400)/\text{ReP2}(700)$ (e5).

8 Claims, 1 Drawing Sheet

(51) Int. Cl.
  *C07C 251/88* (2006.01)
  *C07D 333/10* (2006.01)
  *C07D 333/22* (2006.01)
  *C08F 22/20* (2006.01)
  *C08F 22/22* (2006.01)
  *C08F 22/24* (2006.01)
  *C08J 5/18* (2006.01)
  *G02B 5/30* (2006.01)

(52) U.S. Cl.
  CPC ......... *C07D 333/10* (2013.01); *C07D 333/22* (2013.01); *C08F 22/20* (2013.01); *C08F 22/22* (2013.01); *C08F 22/24* (2013.01); *C08J 5/18* (2013.01); *G02B 5/30* (2013.01); *G02B 5/3016* (2013.01); *G02F 1/133633* (2021.01); *G02F 1/133635* (2021.01); *C08J 2335/02* (2013.01)

(58) Field of Classification Search
  USPC .................................................. 349/117–121
  See application file for complete search history.

(56) References Cited

U.S. PATENT DOCUMENTS

| | | | |
|---|---|---|---|
| 9,234,056 B2 * | 1/2016 | Sakamoto | C09K 19/3477 |
| 9,586,917 B2 | 3/2017 | Sakamoto et al. | |
| 10,173,992 B2 | 1/2019 | Sakamoto et al. | |
| 10,227,292 B2 | 3/2019 | Sakamoto et al. | |
| 2002/0012085 A1 * | 1/2002 | Honda | G02B 5/0278 349/112 |
| 2009/0033835 A1 | 2/2009 | Fukagawa et al. | |
| 2009/0051858 A1 * | 2/2009 | Nakamura | G02F 1/13363 427/536 |
| 2016/0145363 A1 | 5/2016 | Sakamoto et al. | |
| 2019/0062289 A1 | 2/2019 | Sakamoto et al. | |

FOREIGN PATENT DOCUMENTS

| | | | |
|---|---|---|---|
| JP | 2006163169 A | 6/2006 | |
| JP | 2006268033 A | 10/2006 | |
| JP | 4410092 B2 | 2/2010 | |
| JP | 2013213012 A | 10/2013 | |
| JP | 2014206684 A | 10/2014 | |
| WO | 2012141245 A1 | 10/2012 | |
| WO | 2012147904 A1 | 11/2012 | |
| WO | 2014010325 A1 | 1/2014 | |
| WO | 2014126113 A1 | 8/2014 | |

OTHER PUBLICATIONS

Oct. 1, 2019, International Preliminary Report on Patentability issued in the International Patent Application No. PCT/JP2018/010646.

* cited by examiner

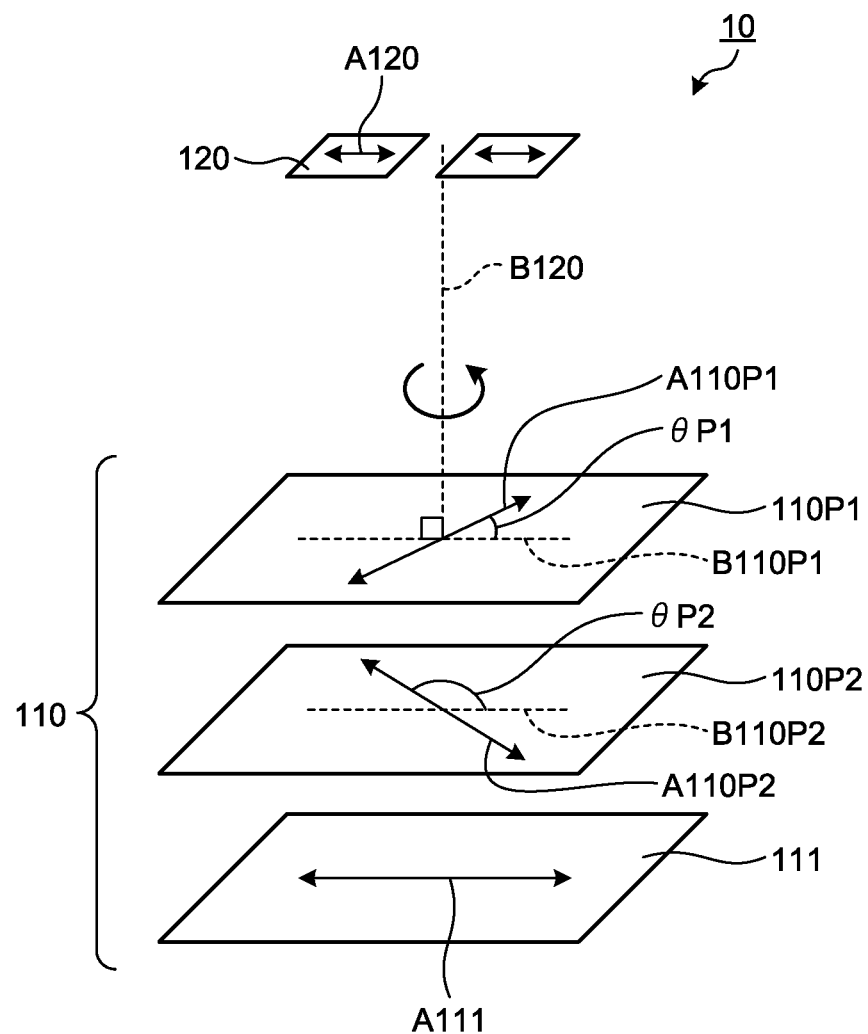

MULTILAYER PHASE DIFFERENCE PLATE, POLARIZING PLATE, AND IMAGE DISPLAY DEVICE

CROSS-REFERENCE TO RELATED APPLICATIONS

The present application is a divisional application of U.S. patent application Ser. No. 16/493,029 filed Sep. 11, 2019, which is a National Stage Application of PCT/JP2018/010646 filed Mar. 16, 2018, which claims priority of Japanese Patent Application No. 2017-063958 filed Mar. 28, 2017. The disclosures of the prior applications are hereby incorporated by reference herein in their entirety.

FIELD

The present invention relates to a phase difference plate and a multilayer phase difference plate, a polarizing plate, and an image display device including the phase difference plate, as well as a polymerizable compound.

BACKGROUND

A phase difference plate is widely used as a constituent element of a display device such as a liquid crystal display device and an organic electroluminescent display device. For example, a ¼ wavelength plate is widely used for the purpose of converting circularly polarized light into linearly polarized light and converting linearly polarized light into circularly polarized light. A liquid crystal material is known as a material constituting such a phase difference plate. For example, a material obtained by rendering a polymerizable liquid crystal compound to be in a liquid crystal state and polymerizing the compound while the liquid crystal state is maintained is known (e.g., Patent literatures 1 and 2).

CITATION LIST

Patent Literature

Patent Literature 1: Japanese Patent Application Laid-Open No. 2014-206684 A
Patent Literature 2: Japanese Patent Application Laid-Open No. 2006-268033 A (corresponding publication: U.S. Patent Application Publication No. 2009/033835)

SUMMARY

Technical Problem

However, the phase difference plates used in prior art fail to achieve uniform optical effects in a wide wavelength range.

Thus, an object of the present invention is to provide a phase difference plate, a multilayer phase difference plate, and a polymerizable compound, capable of achieving uniform optical effects in a wide wavelength range.

Another object of the present invention is to provide a polarizing plate and an image display device, capable of exhibiting uniform performance in a wide wavelength range.

Solution to Problem

The present inventor has conducted studies to solve the aforementioned problem. As a result, the inventor has found that the aforementioned problem can be solved by a phase difference plate which is formed of a liquid crystal material and has a specific in-plane retardation. In particular, the present inventor has found that such a phase difference plate can particularly be easily produced by using a liquid crystal compound having a specific structure. The present invention has been completed on the basis of such findings.

That is, the present invention is as follows.

<1> A phase difference plate comprising a layer of a liquid crystal material oriented in an in-plane direction, wherein an in-plane retardation $Re(\lambda)$ at a wavelength $\lambda$ nm of the phase difference plate satisfies the following formulae (e1) and (e2):

$$\{Re(400)-Re(550)\}/\{Re(550)-Re(700)\}<2.90 \quad (e1),$$

and $$Re(400)/Re(700)>1.13 \quad (e2).$$

<2> The phase difference plate according to <1>, wherein the in-plane retardation $Re(\lambda)$ satisfies the following formula (e3):

$$Re(400)/Re(700) \geq 1.50 \quad (e3).$$

<3> The phase difference plate according to <1> or <2>, wherein the liquid crystal material comprises a polymer of a liquid crystal compound represented by the following formula (I):

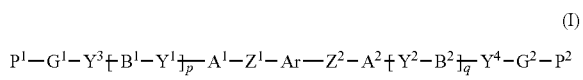

(I)

[in the formula (I),
Ar is a divalent aromatic hydrocarbon ring group having D as a substituent, or a divalent aromatic heterocyclic ring group having D as a substituent,
D is an organic group of 1 to 67 carbon atoms having one or more aromatic rings selected from the group consisting of an aromatic hydrocarbon ring and an aromatic heterocyclic ring,
$Z^1$ and $Z^2$ are each independently a single bond, —O—, —O—CH$_2$—, —CH$_2$—O—, —O—CH$_2$—CH$_2$—, —CH$_2$—CH$_2$—O—, —C(=O)—O—, —O—C(=O)—, —C(=O)—S—, —S—C(=O)—, —NR$^{21}$—C(=O)—, —C(=O)—NR$^{21}$—, —CF$_2$—O—, —O—CF$_2$—, —CH$_2$—CH$_2$—, —CF$_2$—CF$_2$—, —O—CH$_2$—CH$_2$—O—, —CH=CH—C(=O)—O—, —O—C(=O)—CH=CH—, —CH$_2$—C(=O)—O—, —O—C(=O)—CH$_2$—, —CH$_2$—O—C(=O)—, —C(=O)—O—CH$_2$—, —CH$_2$—CH$_2$—C(=O)—O—, —O—C(=O)—CH$_2$—CH$_2$—, —CH$_2$—CH$_2$—O—C(=O)—, —C(=O)—O—CH$_2$—CH$_2$—, —CH=CH—, —N=CH—, —CH=N—, —N=C(CH$_3$)—, —C(CH$_3$)=N—, —N=N—, or —C=C—, and $R^{21}$ independently represents a hydrogen atom or an alkyl group of 1 to 6 carbon atoms,
$A^1$ and $A^2$, and $B^1$ and $B^2$ each independently represent a cyclic aliphatic group optionally having a substituent or an aromatic group optionally having a substituent,
$Y^1$ to $Y^4$ each independently represent a single bond, —O—, —C(=O)—, —C(=O)—O—, —O—C(=O)—, —NR$^{22}$—C(=O)—, —C(=O)—NR$^{22}$—, —O—C(=O)—O—, —NR$^{22}$—C(=O)—O—, —O—C(=O)—NR$^{22}$—, or —NR$^{22}$—C(=O)—

$NR^{23}$, and $R^{22}$ and $R^{23}$ each independently represent a hydrogen atom or an alkyl group of 1 to 6 carbon atoms, $G^1$ and $G^2$ are each independently any of organic groups that are an aliphatic hydrocarbon group of 1 to 20 carbon atoms and a group in which one or more methylene groups (—$CH_2$—) contained in an aliphatic hydrocarbon group of 3 to 20 carbon atoms are substituted by —O— or —C(=O)—, and hydrogen atoms in the organic groups of $G^1$ and $G^2$ may be substituted by an alkyl group of 1 to 5 carbon atoms, an alkoxy group of 1 to 5 carbon atoms, or a halogen atom, $P^1$ and $P^2$ each independently represent a polymerizable group, and p and q are each independently 0 or 1].

<4> A multilayer phase difference plate comprising a phase difference plate $P^1$ and a phase difference plate $P^2$, wherein an in-plane slow axis of the phase difference plate $P^1$ is orthogonal to an in-plane slow axis of the phase difference plate $P^2$, the phase difference plate $P^2$ is the phase difference plate according to any one of <1> to <3>, an in-plane retardation $ReP1(\lambda)$ of the phase difference plate $P^1$ at a wavelength $\lambda$ nm and an in-plane retardation $ReP2(\lambda)$ of the phase difference plate $P^2$ at the wavelength $\lambda$ nm satisfy the following formulae (e4) and (e5):

$$ReP1(550)>ReP2(550) \qquad (e4),\ and$$

$$ReP1(400)/ReP1(700)<ReP2(400)/ReP2(700) \qquad (e5).$$

<5> The multilayer phase difference plate according to <4>, wherein the $ReP1(\lambda)$ satisfies the following formula (e6):

$$ReP1(400)/ReP1(700)<1.10 \qquad (e6).$$

<6> The multilayer phase difference plate according to <4> or <5>, wherein the phase difference plate P1 is a stretched product of a film made of a resin containing an alicyclic structure-containing polymer.

<7> The multilayer phase difference plate according to any one of <4> to <6>, wherein the $ReP1(\lambda)$ and the $ReP2(\lambda)$ satisfy the following formula (e7):

$$90\ nm<ReP1(550)-ReP2(550)<160\ nm \qquad (e7).$$

<8> The multilayer phase difference plate according to any one of <4> to <7>, wherein the $ReP1(\lambda)$ and $ReP2(\lambda)$ satisfy the following formulae (e8) and (e9):

$$180\ nm \leq ReP1(550) \leq 350\ nm \qquad (e8),\ and$$

$$90\ nm \leq ReP2(550) \leq 160\ nm \qquad (e9).$$

<9> A polarizing plate comprising the multilayer phase difference plate according to any one of <4> to <8>, and a linear polarizer.

<10> An image display device comprising the polarizing plate according to <9>.

<11> A polymerizable compound represented by the following formula (I):

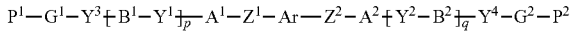

(I)

[in the formula (I),

Ar is a divalent aromatic hydrocarbon ring group having D as a substituent, or a divalent aromatic heterocyclic ring group having D as a substituent, D is an organic group of 1 to 67 carbon atoms having one or more aromatic rings selected from the group consisting of an aromatic hydrocarbon ring and an aromatic heterocyclic ring, $Z^1$ and $Z^2$ are each independently a single bond, —O—, —O—$CH_2$—, —$CH_2$—O—, —O—$CH_2$—$CH_2$—, —$CH_2$—$CH_2$—O—, —C(=O)—O—, —O—C(=O)—, —C(=O)—S—, —S—C(=O)—, —$NR^{21}$—C(=O)—, —C(=O)—$NR^{21}$—, —$CF_2$—O—, —O—$CF_2$—, —$CH_2$—$CH_2$—, —$CF_2$—$CF_2$—, —O—$CH_2$—$CH_2$—O—, —CH=CH—C(=O)—O—, —O—C(=O)—CH=CH—, —$CH_2$—C(=O)—O—, —O—C(=O)—$CH_2$—, —$CH_2$—O—C(=O)—, —C(=O)—O—$CH_2$—, —$CH_2$—$CH_2$—C(=O)—O—, —O—C(=O)—$CH_2$—$CH_2$—, —$CH_2$—$CH_2$—O—C(=O)—, —C(=O)—O—$CH_2$—$CH_2$—, —CH=CH—, —N=CH—, —CH=N—, —N=C($CH_3$)—, —C($CH_3$)=N—, —N=N—, or —C≡C—, and $R^{21}$ independently represents a hydrogen atom or an alkyl group of 1 to 6 carbon atoms, $A^1$ and $A^2$, and $B^1$ and $B^2$ each independently represent a cyclic aliphatic group optionally having a substituent or an aromatic group optionally having a substituent, $Y^1$ to $Y^4$ each independently represent a single bond, —O—, —C(=O)—, —C(=O)—O—, —O—C(=O)—, —$NR^{22}$—C(=O)—, —C(=O)—$NR^{22}$—, —O—C(=O)—O—, —$NR^{22}$—C(=O)—O—, —O—C(=O)—$NR^{22}$—, or —$NR^{22}$—C(=O)—$NR^{23}$, and $R^{22}$ and $R^{23}$ each independently represent a hydrogen atom or an alkyl group of 1 to 6 carbon atoms, $G^1$ and $G^2$ are each independently any of organic groups that are an aliphatic hydrocarbon group of 1 to 20 carbon atoms and a group in which one or more methylene groups (—$CH_2$—) contained in an aliphatic hydrocarbon group of 3 to 20 carbon atoms are substituted by —O— or —C(=O)—, and hydrogen atoms in the organic groups of $G^1$ and $G^2$ may be substituted by an alkyl group of 1 to 5 carbon atoms, an alkoxy group of 1 to 5 carbon atoms, or a halogen atom, $P^1$ and $P^2$ each independently represent a polymerizable group, and p and q are each independently 0 or 1], wherein an in-plane retardation Re(A) at a wavelength $\lambda$ nm of a layer in which the compound is oriented in an in-plane direction satisfies the following formulae (e1) and (e2):

$$\{Re(400)-Re(550)\}/\{Re(550)-Re(700)\}<2.90 \qquad (e1),$$

and $$Re(400)/Re(700)>1.13 \qquad (e2).$$

<12> The polymerizable compound according to <11>, wherein the number of n electrons contained in D is 4 to 12.

<13> The polymerizable compound according to <11> or <12>, wherein

D is a group selected from the group consisting of:

an aromatic hydrocarbon ring group optionally having a substituent, an aromatic heterocyclic ring group optionally having a substituent, a group represented by a formula of —C($R^f$)=N—N($R^g$)$R^h$, a group represented by a formula of —C($R^f$)=N—N=C($R^{g1}$)$R^h$, and a group represented by a formula of —C($R^f$)=N—N=$R^{h1}$, in the formulae $R^f$ represents a hydrogen atom or an alkyl group of 1 to 6 carbon atoms, $R^g$ and $R^{g1}$ represent a hydrogen atom or an organic group of 1 to 30 carbon atoms optionally having a substituent, and $R^h$ and $R^{h1}$ represent an organic group having one or more aromatic rings selected from the group consisting of an aromatic hydrocarbon ring of 6 to 30 carbon atoms and an aromatic heterocyclic ring of 2 to 30 carbon atoms.

Advantageous Effects of Invention

According to the present invention, there can be provided a phase difference plate, a multilayer phase difference plate, and a polymerizable compound, capable of achieving uniform optical effects in a wide wavelength range; and a polarizing plate and an image display device, capable of exhibiting uniform performance in a wide wavelength range.

BRIEF DESCRIPTION OF DRAWINGS

FIG. 1 is an exploded perspective view illustrating a simulation model assumed in Examples.

DESCRIPTION OF EMBODIMENTS

Hereinafter, the present invention will be described in detail with reference to embodiments and examples. However, the present invention is not limited to the following embodiments and examples, and may be freely modified for implementation without departing from the scope of claims of the present invention and the scope of their equivalents.

In the following description, a "long-length" film refers to a film with the length that is 5 times or more the width, and preferably a film with the length that is 10 times or more the width, and specifically refers to a film having a length that allows a film to be wound up into a rolled shape for storage or transportation. The upper limit of the ratio of the length of the film is not particularly limited, but is 10,000 times or less the width thereof, for example.

In the following description, an in-plane retardation Re of a film is a value represented by Re=(nx−ny)×d unless otherwise specified. A thickness direction retardation Rth of a film is a value represented by Rth={(nx+ny)/2−nz} unless otherwise specified. Herein, nx represents a refractive index in a direction in which the maximum refractive index is given among directions perpendicular to the thickness direction of the film (in-plane directions), ny represents a refractive index in a direction, among the above-mentioned in-plane directions of the film, orthogonal to the direction giving nx, nz represents a refractive index in the thickness direction of the film, and d represents the thickness of the film. The measurement wavelength is 550 nm unless otherwise specified. However, when a combination of a plurality of phase difference plates is regarded as a single phase difference plate, nx is a refractive index in the in-plane direction set as the slow axis direction, and ny is a refractive index in the in-plane direction orthogonal thereto. As the in-plane retardation Re, if necessary, a value obtained by performing a processing such as Cauchy fitting to reduce the influence of measurement errors may be adopted.

In the following description, a direction of a constituent element being "parallel", "perpendicular", and "orthogonal" may allow an error within the range of not impairing the advantageous effects of the present invention, for example, within a range of +5°, unless otherwise specified.

In the following description, a "polarizing plate" and a "wavelength plate" include not only a rigid member but also a flexible member such as a resin film, unless otherwise specified.

In the following description, an angle formed by an optical axis (a transmission axis of a polarizer, a slow axis of a phase difference plate, etc.) of each film in a member including a plurality of films represents an angle when the film is viewed from the thickness direction unless otherwise specified.

In the following description, the adhesive includes not only an adhesive in a narrow sense (an adhesive having a shear storage elastic modulus at 23° C. of 1 MPa to 500 MPa after being irradiated with energy rays or after being heat-treated) but also a tackiness agent having a shear storage elastic modulus at 23° C. of less than 1 MPa, unless otherwise specified.

In the following description, the slow axis of a film refers to a slow axis in a plane of the film, unless otherwise specified.

[1. Phase Difference Plate]

The phase difference plate of the present invention includes a layer of a liquid crystal material oriented in an in-plane direction.

In the present application, the term "liquid crystal material" refers to a material obtained by curing a liquid crystal composition containing a liquid crystal compound (i.e., a compound capable of exhibiting, by itself or as a mixture with other substances, a liquid crystal phase). The liquid crystal material may usually include a polymer of a polymerizable liquid crystal compound.

In the present application, a layer of the liquid crystal material being "oriented in the in-plane direction" is a liquid crystal material that, in the layer, has a structure in which the entirety or a part of molecules of the liquid crystal compound is oriented in a certain direction within a plane of the layer. The liquid crystal material oriented in the in-plane direction may be usually obtained by forming a layer of the liquid crystal composition, giving orientation to the liquid crystal compound in the liquid crystal composition, and curing the liquid crystal composition while the orientation is maintained. The orientation of the liquid crystal material may be set to one direction, although the manner of the orientation is not limited thereto. For example, in a case where the liquid crystal compound for forming the liquid crystal material has a plurality of mesogens per molecule and these mesogens can be oriented in different directions, the liquid crystal material oriented in two or more directions within the plane can be obtained. The layer of the liquid crystal material may be usually a layer formed of the liquid crystal material.

The phase difference plate of the present invention may be formed only of the layer of the liquid crystal material or include other layers in addition to the layer of the liquid crystal material.

The thickness of the layer of the liquid crystal material is not particularly limited and may be any thickness as long as desired optical characteristics are exhibited. The thickness of the layer of the liquid crystal material may be usually 0.3 to 8 μm.

In the phase difference plate of the present invention, an in-plane retardation Re(λ) at a wavelength λ nm satisfies the following formulae (e1) and (e2).

$$\{Re(400)-Re(550)\}/\{Re(550)-Re(700)\}<2.90 \quad (e1)$$

$$Re(400)/Re(700)>1.13 \quad (e2)$$

According to the finding by the present inventor, when the in-plane retardation Re(λ) of the phase difference plate satisfies the formula (e1), a combination of the phase difference plate with another phase difference plate gives a multilayer phase difference plate that can have uniform optical effects in a wide wavelength range. Specifically, when the phase difference plate is combined with another phase difference plate to be used as a multilayer wavelength plate such as a ¼ wavelength plate, effects close to those obtained by an ideal wavelength plate can be obtained in a wide range or the entire range of the visible light region. More specifically, the ¼ wavelength plate ideally satisfies a relationship of Re(λ)=λ/4 at all wavelengths in the visible light range. The multilayer phase difference plate obtained by combining the phase difference plate satisfying the aforementioned formula (e1) with other phase difference plates can easily achieve such a linear correlation. Further, the uniform optical effects can be achieved in a wide wavelength range in a thin phase difference plate by satisfying the aforementioned formula (e2).

In the following description, the left side of the formula (e1) of a given phase difference plate, i.e. a value of {Re(400)−Re(550)}/{Re(550)−Re(700)}, may be referred to as a linear index of the given phase difference plate. The linear index of the phase difference plate of the present invention is 2.90 or less, preferably 2.4 or less, and further preferably 2.0 or less. An ideal multilayer phase difference plate can be constituted if the linear index is exactly 1. Thus, the lower limit of the linear index may be set to, for example, 1 or more.

It is preferable that the phase difference plate of the present invention satisfies the following formula (e3).

$$Re(400)/Re(700) \geq 1.50 \quad (e3)$$

When the formula (e3) is satisfied, uniform optical effects can be achieved in a wide wavelength range in a thin multilayer phase difference plate. This allows a polarizing plate and image display device including the phase difference plate of the present invention to be made thinner in thickness and lighter in weight. The value of Re(400)/Re(700) is preferably 1.50 or more, more preferably 1.70 or more, and further preferably 1.90 or more. On the other hand, the upper limit of the value of Re(400)/Re(700) is not particularly limited, but it may be set to, for example, 3.5 or less.

[2. Method for Producing Phase Difference Plate]

The phase difference plate of the present invention may be produced by curing a liquid crystal composition containing a liquid crystal compound. More specifically, the phase difference plate may be produced by forming a layer of the liquid crystal composition, giving orientation to the liquid crystal compound in the liquid crystal composition, and curing the liquid crystal composition while the orientation is maintained, to thereby form a liquid crystal material.

As a preferable example, the liquid crystal material may contain a polymer of a liquid crystal compound represented by the following general formula (I). That is, as a preferable example of the liquid crystal compound for producing the phase difference plate of the present invention, a polymerizable liquid crystal compound represented by the following general formula (I) may be mentioned.

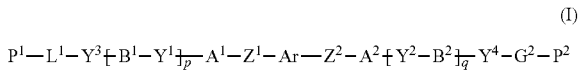

(I)

In the formula (I), Ar is a divalent aromatic hydrocarbon ring group having D as a substituent, or a divalent aromatic heterocyclic ring group having D as a substituent. The number of D's in one Ar is usually one. The aromatic hydrocarbon ring group and aromatic heterocyclic ring group constituting Ar may have another substituent in addition to D.

Herein, D is an organic group of 1 to 67 carbon atoms, preferably 2 to 67 carbon atoms, having one or more aromatic rings selected from the group consisting of an aromatic hydrocarbon ring and an aromatic heterocyclic ring. That is, D may be a group composed only of an aromatic ring, and may be an organic group having both an aromatic ring and a structure other than an aromatic ring.

D may be an aromatic hydrocarbon ring group, an aromatic heterocyclic ring group, or any other organic group.

The term "aromatic hydrocarbon ring group" used herein refers to a moiety of a molecule that includes an aromatic hydrocarbon ring and is connected to the remainder of the molecule via a bond, and in which the bond is a bond that extends from the aromatic hydrocarbon ring of that moiety directly to the remainder. For example, an alkylphenyl group is an aromatic hydrocarbon ring group. On the other hand, although a phenylalkyl group is an organic group having an aromatic hydrocarbon ring, it is an organic group other than an aromatic hydrocarbon ring group.

Similarly, the term "aromatic heterocyclic ring group" refers to a moiety of a molecule that includes an aromatic heterocyclic ring and is connected to the remainder of the molecule via a bond, and in which the bond is a bond that extends from the aromatic heterocyclic ring of that moiety directly to the remainder.

Examples of the divalent aromatic hydrocarbon ring group constituting Ar may include a 1,4-phenylene group, a 1,3-phenylene group, a 1,4-naphthylene group, a 2,6-naphthylene group, a 1,5-naphthylene group, an anthracenyl-9,10-diyl group, an anthracenyl-1,4-diyl group, and an anthracenyl-2,6-diyl group.

Among these, as the divalent aromatic hydrocarbon ring group, a 1,4-phenylene group, a 1,4-naphthylene group, and a 2,6-naphthylene group are preferable, and a 1,4-phenylene group is particularly preferable.

Examples of the divalent aromatic heterocyclic ring group constituting Ar may include a benzothiazole-4,7-diyl group, a 1,2-benzisothiazole-4,7-diyl group, a benzoxazole-4,7-diyl group, an indole-4,7-diyl group, a benzimidazole-4,7-diyl group, a benzopyrazole-4,7-diyl group, a 1-benzofuran-4,7-diyl group, a 2-benzofuran-4,7-diyl group, a benzo[1,2-d:4,5-d']dithiazolyl-4,8-diyl group, a benzo[1,2-d:5,4-d']dithiazolyl-4,8-diyl group, a benzothiophenyl-4,7-diyl group, a 1H-isoindole-1,3(2H)-dione-4,7-diyl group, a benzo[1,2-b:5,4-b']dithiophenyl-4,8-diyl group, a benzo[1,2-b:4,5-b']dithiophenyl-4,8-diyl group, a benzo[1,2-b:5,4-b']difuranyl-4,8-diyl group, a benzo[1,2-b:4,5-b']difuranyl-4,8-diyl group, a benzo[2,1-b:4,5-b']dipyrrole-4,8-diyl group, a benzo[1,2-b:5,4-b']dipyrrole-4,8-diyl group, and a benzo[1,2-d:4,5-d']diimidazole-4,8-diyl group.

Among these, preferable examples of the divalent aromatic heterocyclic ring group may include a benzothiazole-4,7-diyl group, a benzoxazole-4,7-diyl group, a 1-benzofuran-4,7-diyl group, a 2-benzofuran-4,7-diyl group, a benzo[1,2-d:4,5-d']dithiazolyl-4,8-diyl group, a benzo[1,2-d:5,4-d']dithiazolyl-4,8-diyl group, a benzothiophenyl-4,7-diyl group, a 1H-isoindole-1,3(2H)-dione-4,7-diyl group, a benzo[1,2-b:5,4-b']dithiophenyl-4,8-diyl group, a benzo[1,2-b:4,5-b']dithiophenyl-4,8-diyl group, a benzo[1,2-b:5,4-b']difuranyl-4,8-diyl group, and a benzo[1,2-b:4,5-b']difuranyl-4,8-diyl group.

The aromatic hydrocarbon ring group and the aromatic heterocyclic ring group constituting Ar may have a substituent $R^o$ described later in addition to D.

In the present specification, the term "aromatic ring" means a cyclic structure having aromaticity in a broad sense in accordance with the Huckel law. That is, the term means a cyclic conjugate structure having $(4n+2)\pi$ electrons, and a cyclic structure typified by thiophene, furan, benzothiazole, and the like in which a lone pair of electrons of heteroatom such as sulfur, oxygen, nitrogen, and the like is involved in a $\pi$ electron system to thereby exhibit aromaticity.

The number of $\pi$ electrons contained in the Ar is usually 20 or less, and preferably 8 or more and 12 or less.

The number of $\pi$ electrons contained in the aromatic ring constituting Ar is usually 20 or less, preferably 8 or more and 18 or less, and particularly preferably 8 or more and 12 or less, per aromatic ring. When the aromatic ring has a substituent and the substituent further includes an aromatic ring, "the number of $\pi$ electrons" included in the aromatic ring constituting Ar means the total number of $\pi$ electrons which adds in the number of $\pi$ electrons included in the aromatic ring of the substituent. When $\pi$ electrons are present in a ring structure other than the aromatic ring in Ar, those directly incorporated in the ring structure are counted, but $\pi$ electrons not directly incorporated in the ring structure (e.g., $\pi$ electrons present in connecting bonds) are not counted.

Specific examples of the aromatic hydrocarbon ring constituting D may include a benzene ring, a naphthalene ring, an anthracene ring, a phenanthrene ring, a pyrene ring, and a fluorene ring.

Among these, a benzene ring, a naphthalene ring, and an anthracene ring are preferable as the aromatic hydrocarbon ring.

Specific examples of the aromatic heterocyclic rings constituting D may include a 1H-isoindole-1,3(2H)-dione ring, a 1-benzofuran ring, a 2-benzofuran ring, an acridine ring, an isoquinoline ring, an imidazole ring, an indole ring, an oxadiazole ring, an oxazole ring, an oxazolopyrazine ring, an oxazolopyridine ring, an oxazolopyridazine ring, an oxazolopyrimidine ring, a quinazoline ring, a quinoxaline ring, a quinoline ring, a cinnoline ring, a thiadiazole ring, a thiazole ring, a thiazolopyrazine ring, a thiazolopyridine ring, a thiazolopyridazine ring, a thiazolopyrimidine ring, a thiophene ring, a triazine ring, a triazole ring, a naphthyridine ring, a pyrazine ring, a pyrazole ring, a pyranone ring, a pyran ring, a pyridine ring, a pyridazine ring, a pyrimidine ring, a pyrrole ring, a phenanthridine ring, a phthalazine ring, a furan ring, a benzo[c]thiophene ring, a benzo[b]thiophene ring, a benzoisoxazole ring, a benzisothiazole ring, a benzimidazole ring, a benzoxadiazole ring, a benzoxazole ring, a benzothiadiazole ring, a benzothiazole ring, a benzotriazine ring, a benzotriazole ring, and a benzopyrazole ring.

Among these, as the aromatic heterocyclic ring, a monocyclic aromatic heterocyclic ring such as a furan ring, a pyran ring, a thiophene ring, an oxazole ring, an oxadiazole ring, a thiazole ring, and a thiadiazole ring, and a condensed aromatic heterocyclic ring such as a benzothiazole ring, a benzoxazole ring, a quinoline ring, a 1-benzofuran ring, a 2-benzofuran ring, a 1H-isoindole-1,3(2H)-dione ring, a benzo[c]thiophene ring, a benzo[b]thiophene ring, a thiazolopyridine ring, a thiazolopyrazine ring, a benzoisoxazol ring, a benzoxadiazole ring, and a benzothiadiazole ring are preferable.

Without any particular limitation, specific examples of D may include
(D-1) an aromatic hydrocarbon ring group optionally having a substituent,
(D-2) an aromatic heterocyclic ring group optionally having a substituent,
(D-3) a group represented by —C($R^f$)=N—N($R^g$)$R^h$,
(D-4) a group represented by —C($R^f$)=N—N=C($R^{g1}$)$R^h$, and
(D-5) a group represented by —C($R^f$)=N—N=$R^{h1}$.

In the above-described formulae, $R^f$ represents a hydrogen atom or an alkyl group of 1 to 6 carbon atoms such as a methyl group, an ethyl group, a propyl group, and an isopropyl group.

In the above-described formulae, $R^g$ and $R^{g1}$ each independently represent a hydrogen atom or an organic group of 1 to 30 carbon atoms optionally having a substituent. Examples of the organic group of 1 to 30 carbon atoms and the substituent thereof may include the same examples as those listed as the specific examples of the organic group of 1 to 30 carbon atoms and the substituent thereof for Ay, which will be described later.

Further, in the above-described formula, $R^h$ represents an organic group having one or more aromatic rings selected from the group consisting of an aromatic hydrocarbon ring of 6 to 30 carbon atoms and an aromatic heterocyclic ring of 2 to 30 carbon atoms. Specific examples of $R^h$ may include the same examples as those listed as the specific examples of the organic group having one or more aromatic rings selected from the group consisting of an aromatic hydrocarbon ring of 6 to 30 carbon atoms and an aromatic heterocyclic ring of 2 to 30 carbon atoms for Ax, which will be described later.

In the above-described formula, $R^{h1}$ represents an organic group having one or more aromatic rings selected from the group consisting of an aromatic hydrocarbon ring of 6 to 30 carbon atoms and an aromatic heterocyclic ring of 2 to 30 carbon atoms. Specific examples of $R^{h1}$ may include the same examples as those listed as the specific examples of the organic group having one or more aromatic rings selected from the group consisting of an aromatic hydrocarbon ring of 6 to 30 carbon atoms and an aromatic heterocyclic ring of 2 to 30 carbon atoms for Az, which will be described later.

Examples of the aromatic hydrocarbon ring group in a case where D is (D-1) the aromatic hydrocarbon ring group optionally having a substituent may include a phenyl group, a naphthyl group, an anthracenyl group, a phenanthrenyl group, a pyrenyl group, and a fluorenyl group.

Among these, as the aromatic hydrocarbon ring group, a phenyl group and a naphthyl group are preferable, and a phenyl group is more preferable.

Examples of the aromatic heterocyclic ring group in a case where D is (D-2) the aromatic heterocyclic ring group optionally having a substituent may include a phthalimido group, a 1-benzofuranyl group, a 2-benzofuranyl group, an acridinyl group, an isoquinolinyl group, an imidazolyl group, an indolinyl group, a flazanyl group, an oxazolyl group, an oxazolopyrazinyl group, an oxazolopyridinyl group, an oxazolopyridazinyl group, an oxazolopyrimidinyl group, a quinazolinyl group, a quinoxalinyl group, a quinolyl group, a cinnolinyl group, a thiadiazolyl group, a thiazolyl group, a thiazolopyrazinyl group, a thiazolopyridyl group, a thiazolopyridazinyl group, a thiazolopyrimidinyl group, a thienyl group, a triazinyl group, a triazolyl group, a naphthyridinyl group, a pyrazinyl group, a pyrazolyl group, a pyranonyl group, a pyranyl group, a pyrizyl group, a pyridazinyl group, a pyrimidinyl group, a pyrrolyl group, a phenanthridinyl group, a phthalazinyl group, a furanyl group, a benzo[c]thienyl group, a benzo[b]thienyl group, a benzisoxazolyl group, a benzisothiazolyl group, a benzimidazolyl group, a benzoxadiazolyl group, a benzoxazolyl group, a benzothiadiazolyl group, a benzothiazolyl group, a benzotriazinyl group, a benzotriazolyl group, and a benzopyrazolyl group.

Among these, as the aromatic heterocyclic ring group, a monocyclic aromatic heterocyclic ring group such as a furanyl group, a pyranyl group, a thienyl group, an oxazolyl group, a flazanyl group, a thiazolyl group, and a thiadiazolyl group, and a condensed aromatic heterocyclic ring group such as a benzothiazolyl group, a benzoxazolyl group, a quinolyl group, a 1-benzofuranyl group, a 2-benzofuranyl group, a phthalimido group, a benzo[c]thienyl group, a benzo[b]thienyl group, a thiazolopyridyl group, a thiazolopyrazinyl group, a benzoisoxazolyl group, a benzoxadiazolyl group and a benzothiazolyl group are preferable.

Examples of the organic group having one or more aromatic rings selected from the group consisting of an aromatic hydrocarbon ring of 6 to 30 carbon atoms and an aromatic heterocyclic ring of 2 to 30 carbon atoms as the constituent element of (D-3) to (D-5) may include an indanyl group, an indenyl group, a 1, 2, 3,4-tetrahydronaphthyl group, a 1,4-dihydronaphthyl group, a 1,2-dihydronaphthyl group, a 1,3-benzodioxonyl group, a 1,4-benzodioxanyl group, a 2,3-dihydrobenzofuranyl group, a 1,3-dihydroisobenzofuranyl group, a 3,4-dihydro-1H-2-benzopyran group, a 3,4-dihydro-2H-1-benzopyranyl group, a 4H-1-benzopyranyl group, a 2H-1-benzopyranyl group, a 1H-2-benzopyranyl group, a 4-oxo-4H-1-benzopyranyl group, a 4-chromanone group, a dihydropyranyl group, a tetrahydropyranyl group, a dihydrofuranyl group, a tetrahydrofuranyl group, and a 1(3H)-isobenzofuranone group.

Among these, an indanyl group, an indenyl group, a 1,2,3,4-tetrahydronaphthyl group, a 1,4-dihydronaphthyl group, a 1,2-dihydronaphthyl group, a 1,3-benzodioxonyl group, a 1,4-benzodioxanyl group, 3,4-dihydro-1H-2-benzopyran, a 3,4-dihydro-2H-1-benzopyranyl group, a 4H-1-benzopyranyl group, a 2H-1-benzopyranyl group, a 1H-2-benzopyranyl group, a 4-oxo-4H-1-benzopyranyl group, a 4-chromanone group, a dihydropyranyl group, a tetrahydropyranyl group, a dihydrofuranyl group, and a tetrahydrofuranyl group are preferable.

The aromatic hydrocarbon ring and the aromatic heterocyclic ring constituting D (for example, the aromatic hydrocarbon ring constituting (D-1), the aromatic heterocyclic ring constituting (D-2), and the aromatic hydrocarbon ring and the aromatic heterocyclic ring constituting (D-3) to (D-5)), and the aromatic hydrocarbon ring group and the aromatic heterocyclic ring group, which are D, and the organic group having at least one aromatic ring selected from the group consisting of the aromatic hydrocarbon ring of 6 to 30 carbon atoms and the aromatic heterocyclic ring of 2 to 30 carbon atoms, which are D, may have a substituent. The number of the substituents may be one or plural per one ring. When a ring has a plurality of substituents, they may be the same as or different from one another.

Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group; an N, N-dialkylamino group of 1 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; —OCF$_3$; —C(=O)—R$^{b1}$; —O—C(=O)—R$^{b1}$; —C(=O)—O—R$^{b1}$; and —SO$_2$R$^a$.

Herein, R$^{b1}$ represents an alkyl group of 1 to 20 carbon atoms optionally having a substituent, an alkenyl group of 2 to 20 carbon atoms optionally having a substituent, a cycloalkyl group of 3 to 12 carbon atoms optionally having a substituent, or an aromatic hydrocarbon ring group of 5 to 12 carbon atoms optionally having a substituent.

R$^a$ represents an alkyl group of 1 to 12 carbon atoms such as a methyl group or an ethyl group; or an aromatic hydrocarbon ring group of 6 to 20 carbon atoms optionally having, as a substituent, an alkyl group of 1 to 6 carbon atoms or an alkoxy group of 1 to 6 carbon atoms, such as a phenyl group, a 4-methylphenyl group, or a 4-methoxyphenyl group.

Among these, as a substituent, a halogen atom, a cyano group, a nitro group, an alkyl group of 1 to 6 carbon atoms, an alkoxy group of 1 to 6 carbon atoms, and a halogenated alkyl group of 1 to 6 carbon atoms are preferable.

Specific examples of the alkyl group of 1 to 20 carbon atoms and the substituent thereof in a case where R$^{b1}$ is the alkyl group of 1 to 20 carbon atoms optionally having a substituent, specific examples of the alkenyl group of 2 to 20 carbon atoms and the substituent thereof in a case where R$^{b1}$ is the alkenyl group of 2 to 20 carbon atoms optionally having a substituent, specific examples of the cycloalkyl group of 3 to 12 carbon atoms and the substituent thereof in a case where R$^{b1}$ is the cycloalkyl group of 3 to 12 carbon atoms optionally having a substituent, and specific examples of the aromatic hydrocarbon ring group of 5 to 12 carbon atoms and the substituent thereof in a case where R$^{b1}$ is the aromatic hydrocarbon ring group of 5 to 12 carbon atoms optionally having a substituent may include the same examples as those listed as the specific examples of the alkyl group of 1 to 20 carbon atoms and the substituent thereof in a case where R$^b$ is the alkyl group of 1 to 20 carbon atoms optionally having a substituent, the specific examples of the alkenyl group of 2 to 20 carbon atoms and the substituent thereof in a case where R$^b$ is the alkenyl group of 2 to 20 carbon atoms optionally having a substituent, the specific examples of the cycloalkyl group of 3 to 12 carbon atoms and the substituent thereof in a case where R$^b$ is the cycloalkyl group of 3 to 12 carbon atoms optionally having a substituent, and the specific examples of the aromatic hydrocarbon ring group of 5 to 12 carbon atoms and the substituent thereof in a case where R$^b$ is the aromatic hydrocarbon ring group of 5 to 12 carbon atoms optionally having a substituent, respectively, which will be described later.

Examples of the above-mentioned Ar may include a phenylene group substituted with a group represented by a formula —C(R$^f$)=N—N(R$^g$)R$^h$, a phenylene group substituted with a group represented by a formula —C(R$^f$)=N—N=C(R$^{g1}$)R$^h$, a phenylene group substituted with a group represented by a formula —C(R$^f$)=N—N=R$^{h1}$, a naphthylene group substituted with a group represented by a formula —C(R$^f$)=N—N(R$^g$)R$^h$, a naphthylene group substituted with a group represented by a formula —C(R$^f$)=N—N=C(R$^{g1}$)R$^h$, a naphthylene group substituted with a group represented by a formula —C(R$^f$)=N—N=R$^{h1}$, a benzothiazole-4,7-diyl group substituted with a 1-benzofuran-2-yl group, a benzothiazole-4,7-diyl group substituted with a 5-(2-butyl)-1-benzofuran-2-yl group, a benzothiazole-4,7-diyl group substituted with a 4,6-dimethyl-1-benzofuran-2-yl group, a benzothiazole-4,7-diyl group substituted with a 6-methyl-1-benzofuran-2-yl group, a benzothiazole-4,7-diyl group substituted with a 4,6,7-trimethyl-1-benzofuran-2-yl group, a benzothiazole-4,7-diyl group substituted with a 4,5,6-trimethyl-1-benzofuran-2-yl group, a benzothiazole-4,7-diyl group substituted with a 5-methyl-1-benzofuran-2-yl group, a benzothiazole-4,7-diyl group substituted with a 5-propyl-1-benzofuran-2-yl group, a benzothiazole-4,7-diyl group substituted with a 7-propyl-1-benzofuran-2-yl group, a benzothiazole-4,7-diyl group substituted with a 5-fluoro-1-benzofuran-2-yl group, a benzothiazole-4,7-diyl group substituted with a phenyl group, a benzothiazole-4,7-diyl group substituted with a 4-fluorophenyl group, a benzothiazole-4,7-diyl group substituted with a 4-nitrophenyl group, a benzothiazole-4,7-diyl group substituted with a 4-trifluoromethylphenyl group, a benzothiazole-4,7-diyl group substituted with a 4-cyanophenyl group, a benzothiazole-4,7-diyl group substituted with a 4-methanesulfonylphenyl group, a benzothiazole-4,7-diyl group substituted with a thiophene-2-yl group, a benzothiazole-4,7-diyl group substituted with a thiophene-3-yl group, a benzothiazole-4,7-diyl group substituted with a 5-methylthiophene-2-yl group, a benzothiazole-4,7-diyl group substituted with a 5-chlorothiophene-2-yl group, a benzothiazole-4,7-diyl group substituted with a thieno[3,2-b]thiophene-2-yl group, a benzothiazole-4,7-diyl group substituted with a 2-benzothiazolyl group, a benzothiazole-4,7-diyl group substituted with a 4-biphenyl group, a benzothiazole-4,7-diyl group substituted with a 4-propylbiphenyl group, a benzothiazole-4,7-diyl group substituted with a 4-thiazolyl group, a benzothiazole-4,7-diyl group substituted with a 1-phenylethylene-2-yl group, a benzothiazole-4,7-diyl group substituted with a 4-pyridyl group, a benzothiazole-4,7-diyl group substituted with a 2-furyl group, a benzothiazole-4,7-diyl group substituted with a naphtho[1,2-b]furan-2-yl group, a 1H-isoindole-1,3(2H)-dione-4,7-diyl group substituted with a 5-methoxy-2-benzothiazolyl group, a 1H-isoindole-1,3(2H)-dione-4,7-diyl group substituted with a phenyl group, a 1H-isoindole-1,3(2H)-dione-4,7-diyl group substituted with a 4-nitrophenyl group, and a 1H-isoindole-1,3(2H)-dione-4,7-diyl group substituted with a 2-thiazolyl group. Herein, R$^f$, R$^g$, R$^{g1}$, R$^h$, and R$^{h1}$ represent the same meanings as described above.

Herein, as Ar, a group represented by any of the following formulae (IIa-1) to (IIa-7), formulae (IIb-1) to (IIb-7), and formulae (IIc-1) to (IIc-7) is preferable.

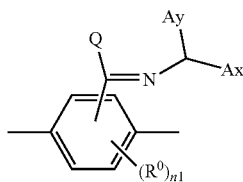

(IIa-1)

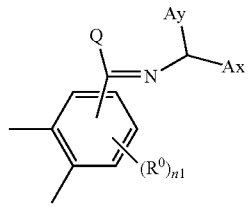

(IIa-2)

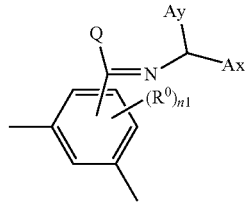

(IIa-3)

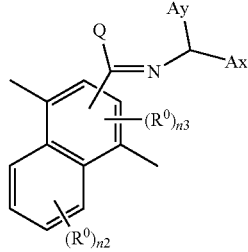

(IIa-4)

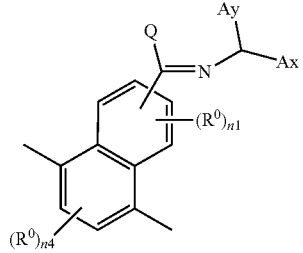

(IIa-5)

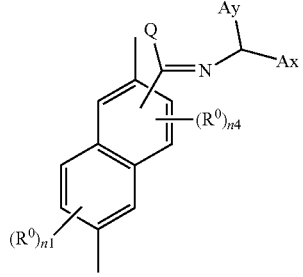

(IIa-6)

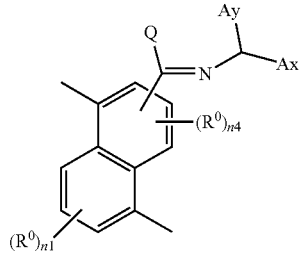

(IIa-7)

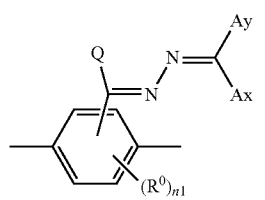
(IIb-1)
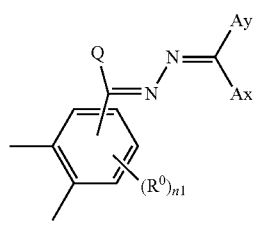
(IIb-2)
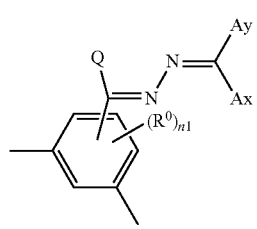
(IIb-3)
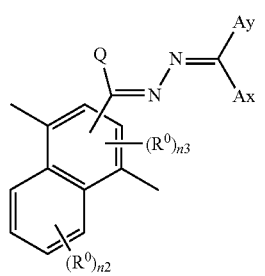
(IIb-4)
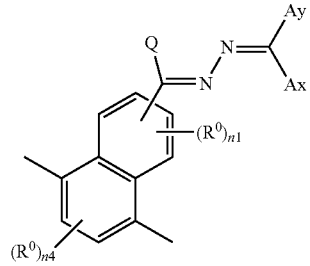
(IIb-5)
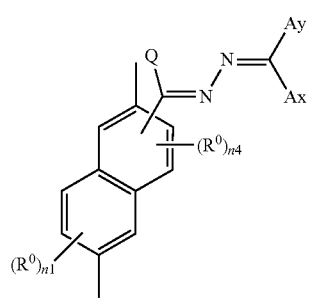
(IIb-6)
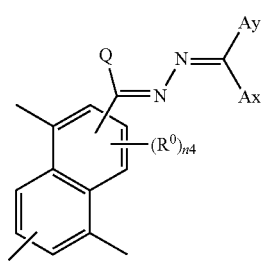
(IIb-7)
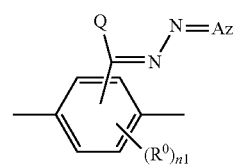
(IIc-1)
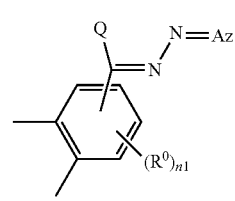
(IIc-2)
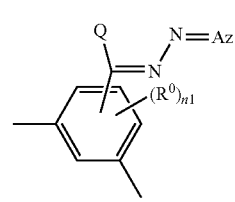
(IIc-3)
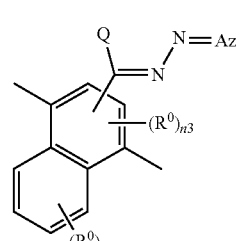
(IIc-4)
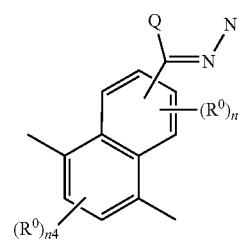
(IIc-5)
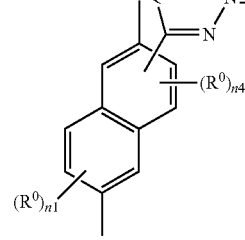
(IIc-6)

-continued

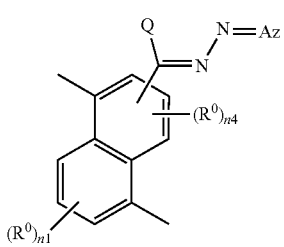
(IIc-7)

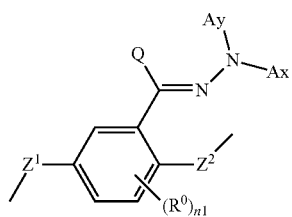
(iia-1)

In the above-described formulae (IIa-1) to (IIa-7), formulae (IIb-1) to (IIb-7), and formulae (IIc-1) to (IIc-7), Ax represents an organic group having one or more aromatic rings selected from the group consisting of an aromatic hydrocarbon ring of 6 to 30 carbon atoms and an aromatic heterocyclic ring of 2 to 30 carbon atoms, Ay represents a hydrogen atom or an organic group of 1 to 30 carbon atoms optionally having a substituent, Az represents an organic group having one or more aromatic rings selected from the group consisting of an aromatic hydrocarbon ring of 6 to 30 carbon atoms and an aromatic heterocyclic ring of 2 to 30 carbon atoms, the aromatic rings in Ax and Ax may have a substituent, and Q represents a hydrogen atom or an alkyl group of 1 to 6 carbon atoms. Herein, examples of the alkyl group of 1 to 6 carbon atoms in Q may include a methyl group, an ethyl group, an n-propyl group, and an isopropyl group.

$R^0$ represents a halogen atom; a cyano group; an alkyl group of 1 to 6 carbon atoms such as a methyl group, an ethyl group, a propyl group, an isopropyl group, a butyl group, a sec-butyl group, and a tertiary butyl group; an alkenyl group of 2 to 6 carbon atoms; a halogenated alkyl group of 1 to 6 carbon atoms; an N, N-dialkylamino group of 2 to 12 carbon atoms; an alkoxy group of 1 to 6 carbon atoms; a nitro group; —C(=O)—$R^{a1}$; —C(=O)—O—$R^{a1}$; or —$SO_2 R^{a1}$, and $R^{a1}$ represents an aliphatic hydrocarbon group of 1 to 12 carbon atoms. When a plurality of $R^0$'s are present, the plurality of $R^0$s may be the same as or different from one another. As the $R^0$, a halogen atom, a cyano group, an alkyl group of 1 to 6 carbon atoms, a halogenated alkyl group of 1 to 6 carbon atoms, an alkoxy group of 1 to 6 carbon atoms, and a nitro group are preferable from the viewpoint of improving solubility.

Further, n1 is 0 to 3, n2 is 0 to 4, n3 is 0 or 1, and n4 is 0 to 2. It is preferable that n1=0, n2=0, n3=0, and n4=0.

Specific examples of the aliphatic hydrocarbon group of 1 to 12 carbon atoms as examples of $R^{a1}$ may include an alkyl group of 1 to 12 carbon atoms such as a methyl group and an ethyl group, an alkenyl group of 1 to 12 carbon atoms such as a vinyl group, an aryl group, and a butenyl group, and an alkynyl group of 1 to 12 carbon atoms such as a propynyl group, a butynyl group, and a pentynyl group. An alkyl group of 1 to 12 carbon atoms is preferable.

As Ar, structures represented by the following formulae (iia-1) to (iia-21), formulae (iib-1) to (iib-21), and formulae (iic-1) to (iic-21) are more preferable. In the following formulae, $Z^1$ and $Z^2$ are described for the convenience of better clarification of the bonding states. In the following formulae, $Z^1$, $Z^2$, Ax, Ay, Az, Q, $R^0$, n1, n2, n3, and n4 represent the same meanings as described above. Among these, the formulae (iia-1), (iia-2), (iia-10), and (iia-12), formulae (iib-1), (iib-2), (iib-10), and (iib-12), and formulae (iic-1), (iic-2), (iic-10), and (iic-12) are particularly preferable.

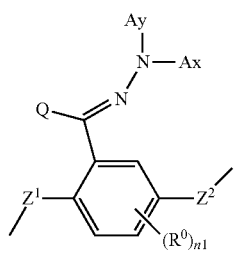
(iia-2)

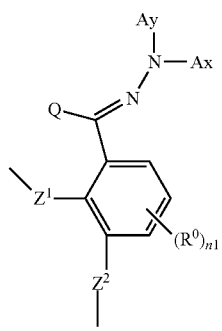
(iia-3)

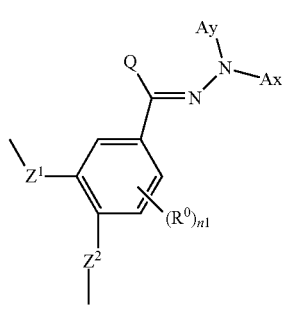
(iia-3)

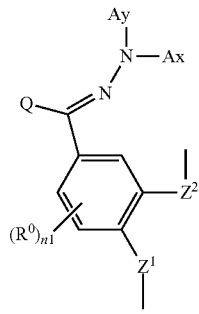
(iia-5)

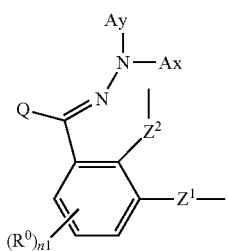
(iia-6)
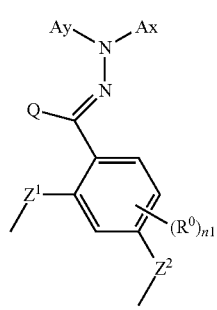
(iia-7)
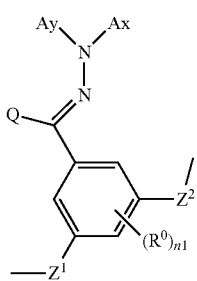
(iia-8)
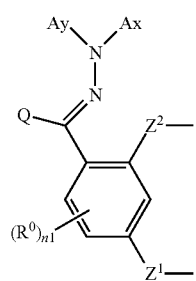
(iia-9)
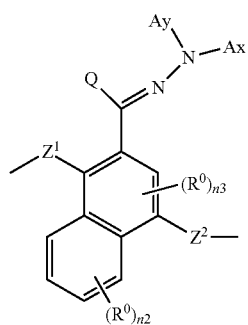
(iia-10)
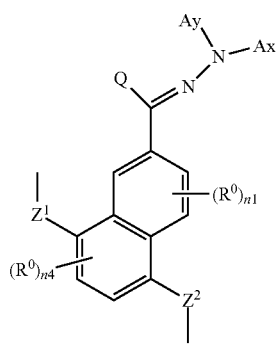
(iia-11)
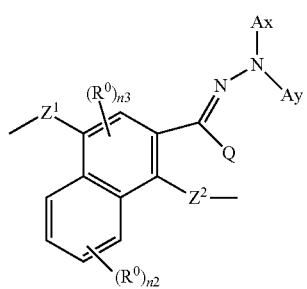
(iia-12)
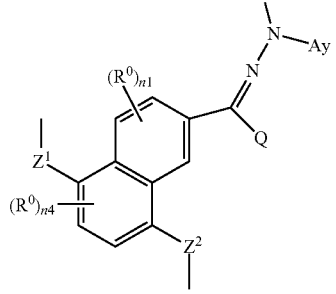
(iia-13)
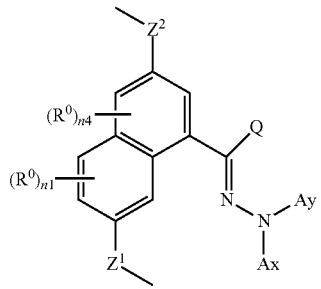
(iia-14)
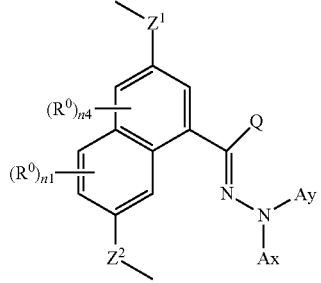
(iia-15)

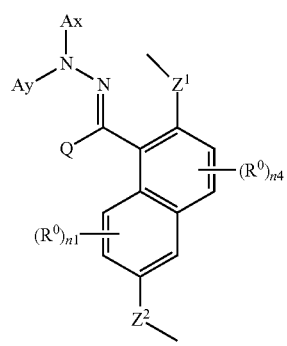
(iia-16)
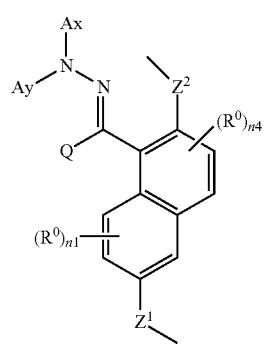
(iia-17)
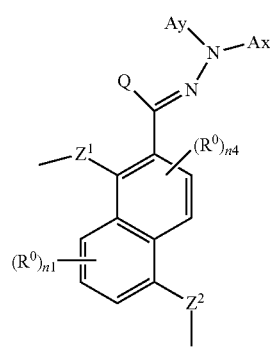
(iia-18)
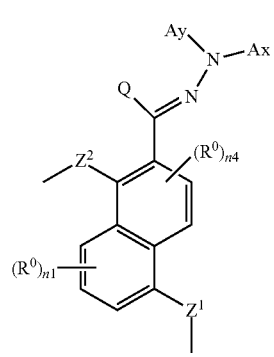
(iia-19)
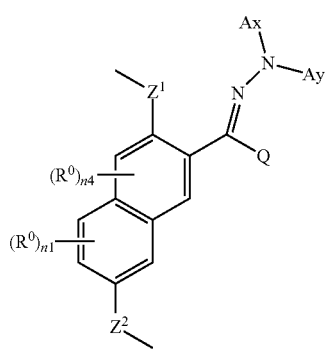
(iia-20)
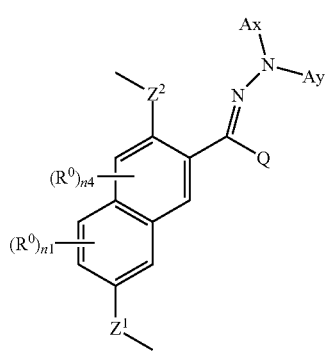
(iia-21)
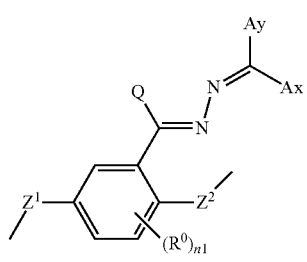
(iib-1)
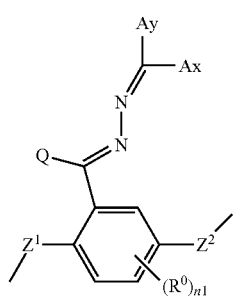
(iib-2)
(iib-3)

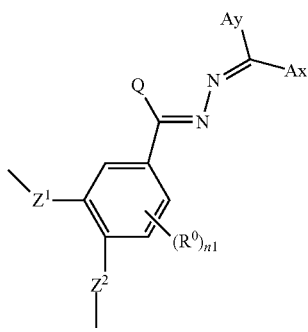 (iib-4)
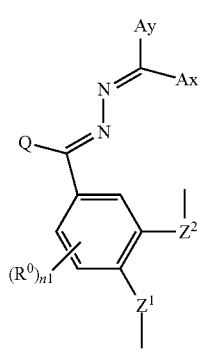 (iib-5)
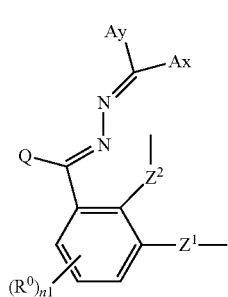 (iib-6)
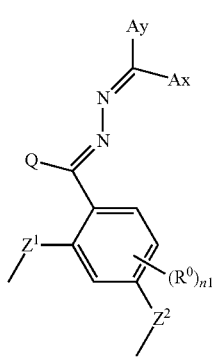 (iib-7)
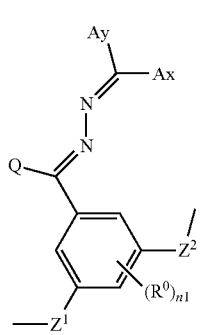 (iib-8)
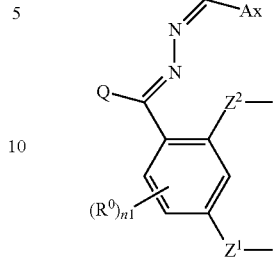 (iib-9)
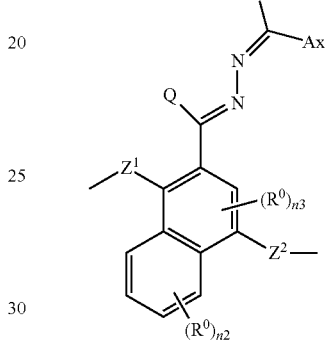 (iib-10)
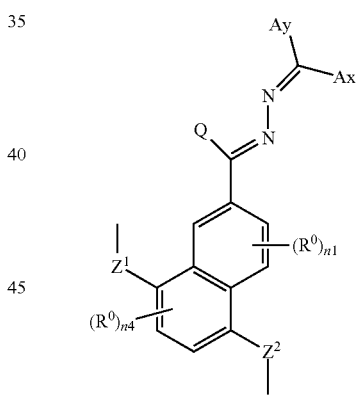 (iib-11)
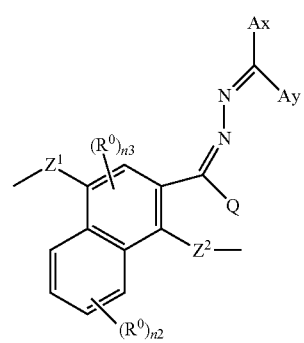 (iib-12)

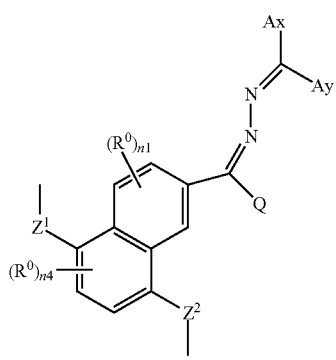
(iib-13)
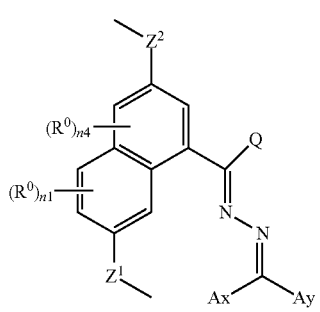
(iib-14)
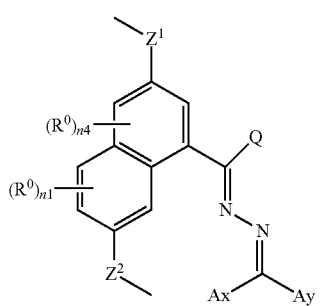
(iib-15)
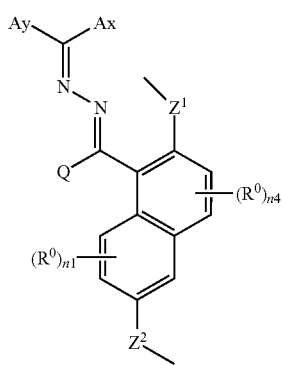
(iib-16)
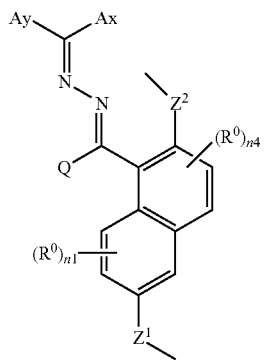
(iib-17)
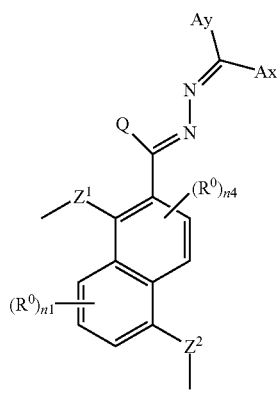
(iib-18)
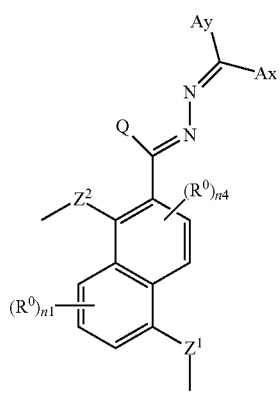
(iib-19)
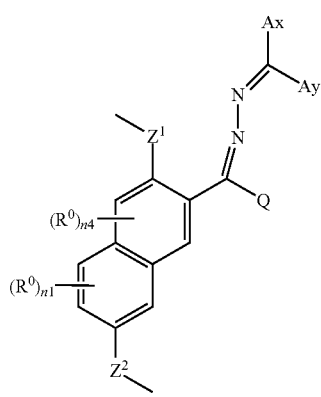
(iib-20)

(iib-21)
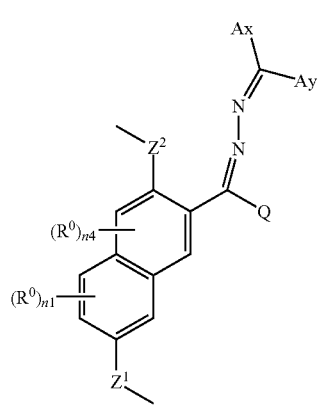
(iic-1)
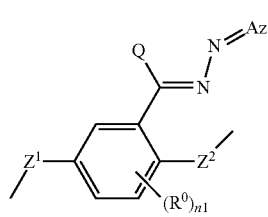
(iic-2)
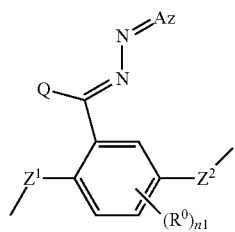
(iic-3)
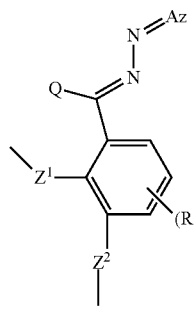
(iic-4)
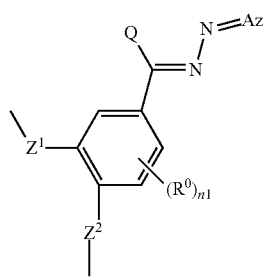
(iic-5)
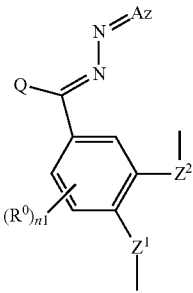
(iic-6)
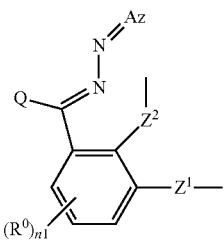
(iic-7)
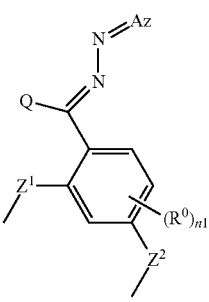
(iic-8)
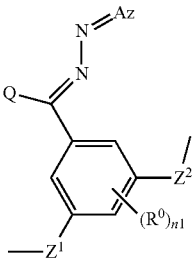
(iic-9)
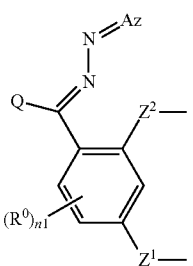

(iic-10)
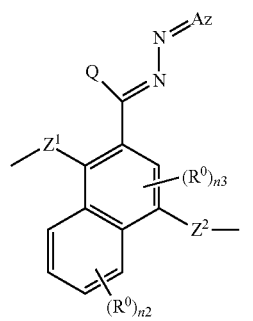
(iic-11)
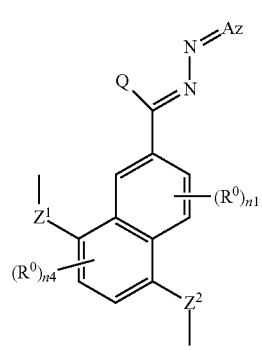
(iic-12)
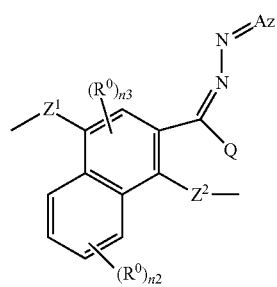
(iic-13)
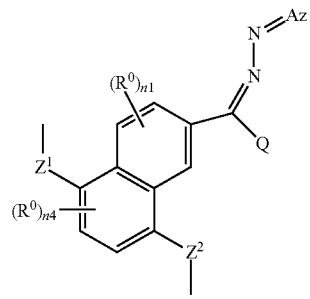
(iic-14)
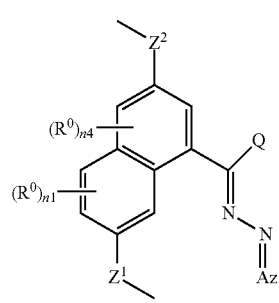
(iic-15)
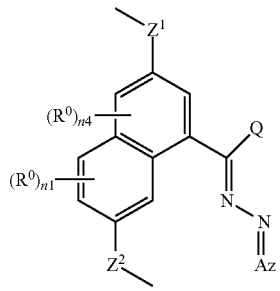
(iic-16)
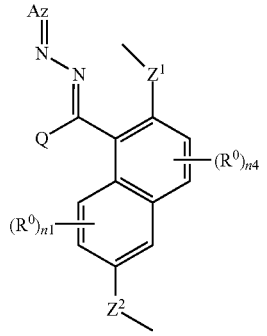
(iic-17)
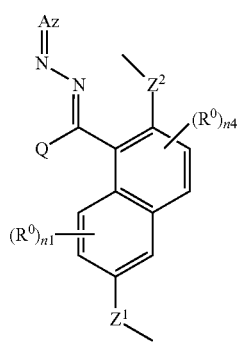
(iic-18)
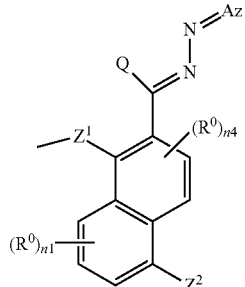
(iic-19)
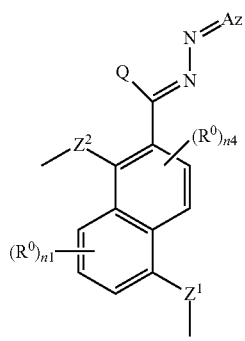

-continued

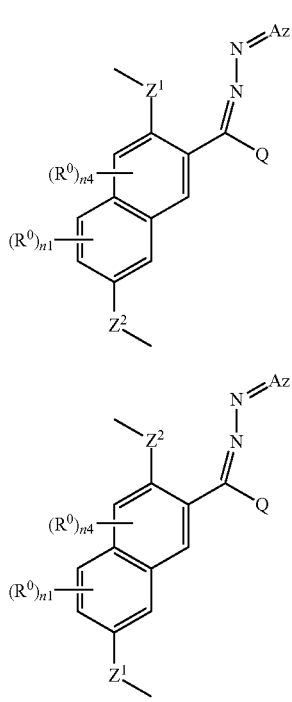

(iic-20)

(iic-21)

Ax may have a plurality of aromatic rings, and may have an aromatic hydrocarbon ring and an aromatic heterocyclic ring. When a plurality of aromatic hydrocarbon rings and aromatic heterocyclic ring are present, they may be the same as or different from one another.

Examples of the aromatic hydrocarbon ring in Ax may include a benzene ring, a naphthalene ring, an anthracene ring, a phenanthrene ring, a pyrene ring, and a fluorene ring. Among these, as the aromatic hydrocarbon ring, a benzene ring, a naphthalene ring, and an anthracene ring are preferable.

Examples of the aromatic heterocyclic ring in Ax may include a 1H-isoindole-1,3(2H)-dione ring, a 1-benzofuran ring, a 2-benzofuran ring, an acridine ring, an isoquinoline ring, an imidazole ring, an indole ring, an oxadiazole ring, an oxazole ring, an oxazolopyrazine ring, an oxazolopyridine ring, an oxazolopyridazyl ring, an oxazolopyrimidine ring, a quinazoline ring, a quinoxaline ring, a quinoline ring, a cinnoline ring, a thiadiazole ring, a thiazole ring, a thiazolopyrazine ring, a thiazolopyridine ring, a thiazolopyridazine ring, a thiazolopyrimidine ring, a thiophene ring, a triazine ring, a triazole ring, a naphthyridine ring, a pyrazine ring, a pyrazole ring, a pyranone ring, a pyran ring, a pyridine ring, a pyridazine ring, a pyrimidine ring, a pyrrole ring, a phenanthridine ring, a phthalazine ring, a furan ring, a benzo[c]thiophene ring, a benzo[b]thiophene ring, a benzoisoxazole ring, a benzoisothiazole ring, a benzoimidazole ring, a benzoxadiazole ring, a benzoxazole ring, a benzothiadiazole ring, a benzothiazole ring, a benzotriazine ring, a benzotriazole ring, and a benzopyrazole ring.

Among these, as the aromatic heterocyclic ring, a monocyclic aromatic heterocyclic ring such as a furan ring, a pyran ring, a thiophene ring, an oxazole ring, an oxadiazole ring, a thiazole ring, and a thiadiazole ring; and a condensed aromatic heterocyclic ring such as a benzothiazole ring, a benzoxazole ring, a quinoline ring, a 1-benzofuran ring, a 2-benzofuran ring, a 1H-isoindole-1,3(2H)-dione ring, a benzo[c]thiophene ring, a benzo[b]thiophene ring, a thiazo-lopyridine ring, a thiazolopyrazine ring, a benzoisoxazol ring, a benzoxadiazole ring, and a benzothiazole ring are preferable.

The aromatic ring in Ax may have a substituent. Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group; an N, N-dialkylamino group of 2 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; $-OCF_3$; $-C(=O)-R^b$; $-C(=O)-O-R^b$; and $-SO_2R^a$. Herein, $R^b$ represents an alkyl group of 1 to 20 carbon atoms optionally having a substituent, an alkenyl group of 2 to 20 carbon atoms optionally having a substituent, a cycloalkyl group of 3 to 12 carbon atoms optionally having a substituent, or an aromatic hydrocarbon ring group of 5 to 12 carbon atoms optionally having a substituent. In addition, $R^a$ represents the same meanings as described above. Among these, as the substituent of the aromatic ring in Ax, a halogen atom, a cyano group, an alkyl group of 1 to 6 carbon atoms, and an alkoxy group of 1 to 6 carbon atoms are preferable.

Ax may have a plurality of substituents selected from the substituents described above. When Ax has a plurality of substituents, the substituents may be the same as or different from one another.

Examples of the alkyl group of 1 to 20 carbon atoms in a case where $R^b$ is the alkyl group of 1 to 20 carbon atoms optionally having a substituent may include a methyl group, an ethyl group, an n-propyl group, an isopropyl group, an n-butyl group, an isobutyl group, a 1-methylpentyl group, a 1-ethylpentyl group, a sec-butyl group, a t-butyl group, an n-pentyl group, an isopentyl group, a neopentyl group, an n-hexyl group, an isohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group. The number of carbon atoms of the alkyl group of 1 to 20 carbon atoms optionally having a substituent is preferably 1 to 12, and more preferably 4 to 10.

Examples of the alkenyl group of 2 to 20 carbon atoms in a case where $R^b$ is the alkenyl group of 2 to 20 carbon atoms optionally having a substituent may include a vinyl group, a propenyl group, an isopropenyl group, a butenyl group, an isobutenyl group, a pentenyl group, a hexenyl group, a heptenyl group, an octenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadenyl group, and an icosenyl group. The number of carbon atoms of the alkenyl group of 2 to 20 carbon atoms optionally having a substituent is preferably 2 to 12.

The number of substituents in a case where $R^b$ is the alkyl group of 1 to 20 carbon atoms having a substituent and in a case where $R^b$ is the alkenyl group of 2 to 20 carbon atoms having a substituent may be one or plural. When a plurality of substituents are included, they may be the same as or different from one another. Examples of the substituent may include a halogen atom such as a fluorine atom and a chlorine atom; a cyano group; an N, N-dialkylamino group of 2 to 12 carbon atoms such as a dimethylamino group; an alkoxy group of 1 to 20 carbon atoms such as a methoxy group, an ethoxy group, an isopropoxy group, and a butoxy group; an alkoxy group of 1 to 12 carbon atoms substituted with an alkoxy group of 1 to 12 carbon atoms such as a methoxymethoxy group and a methoxyethoxy group; a nitro group; an aromatic hydrocarbon ring group of 6 to 20 carbon atoms such as a phenyl group and a naphthyl group; an aromatic heterocyclic ring group such as a triazolyl group, a pyrrolyl group, a furanyl group, a thiophenyl group, and a benzothiazole-2-yl thio group; a cycloalkyl group of 3 to 8 carbon atoms such as a cyclopropyl group, a cyclopentyl group, and a cyclohexyl group; a cycloalkyloxy group of 3 to 8 carbon atoms such as a cyclopentyloxy group and a cyclohexyloxy group; a cyclic ether group of 2 to 12 carbon atoms such as a tetrahydrofuranyl group, a tetrahydropyranyl group, a dioxoranyl group, and a dioxanyl group; an aryloxy group of 6 to 14 carbon atoms such as a phenoxy group and a naphthoxy group; a fluoroalkyl group of 1 to 12 carbon atoms, in which one or more hydrogen atoms are substituted by a fluorine atom, such as a trifluoromethyl group, a pentafluoroethyl group, and —$CH_2CF_3$; a benzofuryl group; a benzopyranyl group; a benzodioxolyl group; and a benzodioxanyl group. Among these, as the substituent in $R^b$, a halogen atom such as a fluorine atom and a chlorine atom; a cyano group; an alkoxy group of 1 to 20 carbon atoms such as a methoxy group, an ethoxy group, an isopropoxy group, and a butoxy group; a nitro group; an aromatic hydrocarbon ring group of 6 to 20 carbon atoms such as a phenyl group and a naphthyl group; an aromatic heterocyclic ring group of 2 to 20 carbon atoms such as a furanyl group and a thiophenyl group; a cycloalkyl group of 3 to 8 carbon atoms such as a cyclopropyl group, a cyclopentyl group, and a cyclohexyl group; and a fluoroalkyl group of 1 to 12 carbon atoms, in which one or more hydrogen atoms are substituted by a fluorine atom, such as a trifluoromethyl group, a pentafluoroethyl group, and —$CH_2CF_3$ are preferable.

Examples of the cycloalkyl group of 3 to 12 carbon atoms in a case where $R^b$ is the cycloalkyl group of 3 to 12 carbon atoms optionally having a substituent may include a cyclopropyl group, a cyclobutyl group, a cyclopentyl group, a cyclohexyl group, and a cyclooctyl group. Among these, a cyclopentyl group and a cyclohexyl group are preferable.

When $R^b$ is the cycloalkyl group of 3 to 12 carbon atoms having a substituent, the number of substituents may be one or plural. When a plurality of substituents are included, they may be the same as or different from one another. Examples of the substituent may include a halogen atom such as a fluorine atom and a chlorine atom; a cyano group; an N, N-dialkylamino group of 2 to 12 carbon atoms such as a dimethylamino group; an alkyl group of 1 to 6 carbon atoms such as a methyl group, an ethyl group, and a propyl group; an alkoxy group of 1 to 6 carbon atoms such as a methoxy group, an ethoxy group, and an isopropoxy group; a nitro group; and an aromatic hydrocarbon ring group of 6 to 20 carbon atoms such as a phenyl group and a naphthyl group. Among these, as a substituent of the cycloalkyl group of 3 to 12 carbon atoms of $R^b$, a halogen atom such as a fluorine atom and a chlorine atom; a cyano group; an alkyl group of 1 to 6 carbon atoms such as a methyl group, an ethyl group, and a propyl group; an alkoxy group of 1 to 6 carbon atoms such as a methoxy group, an ethoxy group, and an isopropoxy group; a nitro group; and an aromatic hydrocarbon ring group of 6 to 20 carbon atoms such as a phenyl group and a naphthyl group are preferable.

Examples of the aromatic hydrocarbon ring group of 5 to 12 carbon atoms in a case where $R^b$ is the aromatic hydrocarbon ring group of 5 to 12 carbon atoms optionally having a substituent may include a phenyl group, a 1-naphthyl group, and a 2-naphthyl group. Among these, a phenyl group is preferable.

The number of substituents in a case where $R^b$ has 5 to 12 carbon atoms having a substituent may be one or plural. When a plurality of substituents are included, they may be the same as or different from one another. Examples of the substituent may include a halogen atom such as a fluorine atom and a chlorine atom; a cyano group; an N, N-dialkylamino group of 2 to 12 carbon atoms such as a dimethylamino group; an alkoxy group of 1 to 20 carbon atoms such as a methoxy group, an ethoxy group, an isopropoxy group, and a butoxy group; an alkoxy group of 1 to 12 carbon atoms substituted with an alkoxy group of 1 to 12 carbon atoms such as a methoxymethoxy group and a methoxyethoxy group; a nitro group; an aromatic hydrocarbon ring group of 6 to 20 carbon atoms such as a phenyl group and a naphthyl group; an aromatic heterocyclic ring group such as a triazolyl group, a pyrrolyl group, a furanyl group, and a thiophenyl group; a cycloalkyl group of 3 to 8 carbon atoms such as a cyclopropyl group, a cyclopentyl group, and a cyclohexyl group; a cycloalkyloxy group of 3 to 8 carbon atoms such as a cyclopentyloxy group and a cyclohexyloxy group; a cyclic ether group of 2 to 12 carbon atoms such as a tetrahydrofuranyl group, a tetrahydropyranyl group, a dioxoranyl group, and a dioxanyl group; an aryloxy group of 6 to 14 carbon atoms such as a phenoxy group and a naphthoxy group; a fluoroalkyl group of 1 to 12 carbon atoms, in which one or more hydrogen atoms are substituted by a fluorine atom, such as a trifluoromethyl group, a pentafluoroethyl group, and —$CH_2CF_3$; —$OCF_3$; a benzofuryl group; a benzopyranyl group; a benzodioxolyl group; and a benzodioxanyl group. Among these, as the substituent of the aromatic hydrocarbon ring group of 5 to 12 carbon atoms, one or more substituents selected from a halogen atom such as a fluorine atom and a chlorine atom; a cyano group; an alkoxy group of 1 to 20 carbon atoms such as a methoxy group, an ethoxy group, an isopropoxy group, and a butoxy group; a nitro group; an aromatic hydrocarbon ring group of 6 to 20 carbon atoms such as a phenyl group and a naphthyl group; an aromatic heterocyclic ring group of 2 to 20 carbon atoms such as a furanyl group and a thiophenyl group; a cycloalkyl group of 3 to 8 carbon atoms such as a cyclopropyl group, a cyclopentyl group, and a cyclohexyl group; a fluoroalkyl group of 1 to 12 carbon atoms, in which one or more hydrogen atoms are substituted by a fluorine atom, such as a trifluoromethyl group, a pentafluoroethyl group, and —$CH_2CF_3$; and —$OCF_3$ are preferable.

Herein, the aromatic ring in Ax may have a plurality of the same or different substituents, and two adjacent substituents may be bonded together to form a ring. The ring formed may be a single ring or a fused polycycle ring, and may be an unsaturated ring or a saturated ring.

The "number of carbon atoms" of the aromatic hydrocarbon ring having 6 to 30 carbon atoms and the aromatic heterocyclic ring of 2 to 30 carbon atoms included in Ax means the number of carbon atoms of the ring itself, which does not include the carbon atoms of the substituent bonded to the ring.

Specific examples of Ax may include the following (Ax-1) to (Ax-5).

(Ax-1) a hydrocarbon ring group of 6 to 40 carbon atoms having one or more aromatic hydrocarbon rings each having 6 to 30 carbon atoms, (Ax-2) a heterocyclic ring group of 2 to 40 carbon atoms having one or more aromatic rings selected from the group consisting of an aromatic hydrocarbon ring of 6 to 30 carbon atoms and an aromatic heterocyclic ring of 2 to 30 carbon atoms, (Ax-3) an alkyl group of 1 to 12 carbon atoms substituted with one or more of an aromatic hydrocarbon ring group of 6 to 30 carbon atoms and an aromatic heterocyclic ring group of 2 to 30 carbon atoms, (Ax-4) an alkenyl group of 2 to 12 carbon atoms substituted with one or more of an aromatic hydrocarbon ring group of 6 to 30 carbon atoms and an aromatic heterocyclic ring group of 2 to 30 carbon atoms, and (Ax-5) An alkynyl group of 2 to 12 carbon atoms substituted with one or more of an aromatic hydrocarbon ring group of 6 to 30 carbon atoms and an aromatic heterocyclic ring group of 2 to 30 carbon atoms.

Specific examples of the aromatic hydrocarbon ring in (Ax-1) may include the same examples as those listed as the specific examples of the aromatic hydrocarbon ring in Ax. Specific examples of the hydrocarbon ring group in (Ax-1) may include an aromatic hydrocarbon ring group of 6 to 30 carbon atoms (such as a phenyl group, a naphthyl group, an anthracenyl group, a phenanthrenyl group, a pyrenyl group, and a fluorenyl group), an indanyl group, an indenyl group, a 1,2,3,4-tetrahydronaphtyl group, a 1,4-dihydronaphthyl group, and a 1,2-dihydronaphthyl group.

Specific examples of the aromatic hydrocarbon ring and the aromatic heterocyclic ring in (Ax-2) may include the same examples as those listed as the specific examples of the aromatic hydrocarbon ring and the aromatic heterocyclic ring in Ax. Specific examples of the heterocyclic ring group in (Ax-2) may include an aromatic heterocyclic ring group of 2 to 30 carbon atoms (such as a phthalimido group, a 1-benzofuranyl group, a 2-benzofuranyl group, an acridinyl group, an isoquinolinyl group, an imidazolyl group, an indolinyl group, a flazanyl group, an oxazolyl group, an oxazolopyrazinyl group, an oxazolopyridinyl group, an oxazolopyridazinyl group, an oxazolopyrimidinyl group, a quinazolinyl group, a quinoxalinyl group, a quinolyl group, a cinnolinyl group, a thiadiazolyl group, a thiazolyl group, a thiazolopyrazinyl group, a thiazolopyridinyl group, a thiazolopyridazinyl group, a thiazolopyrimidinyl group, a thienyl group, a triazinyl group, a triazolyl group, a naphthyridinyl group, a pyrazinyl group, a pyrazolyl group, a pyranonyl group, a pyranyl group, a pyrizyl group, a pyridazinyl group, a pyrimidinyl group, a pyrrolyl group, a phenanthridinyl group, a phthalazinyl group, a furanyl group, a benzo[c]thienyl group, a benzo[b]thienyl group, a benzisoxazolyl group, a benzisothiazolyl group, a benzimidazolyl group, a benzoxazolyl group, a benzothiadiazolyl group, a benzothiazolyl group, a benzotriazinyl group, a benzotriazolyl group, a benzopyrazolyl group, a dihydropyranyl group, a tetrahydropyranyl group, a dihydrofuranyl group, a tetrahydrofuranyl group), a 2,3-dihydroindolyl group, a 9,10-dihydroacridinyl group, a 1,2,3,4-tetrahydroquinolyl group, a 1,4-benzodioxanyl group, a 2,3-dihydrobenzofuranyl group, a 1,3-dihydroisobenzofuranyl group, 3,4-dihydro-1H-2-benzopyran, a 3,4-dihydro-2H-1-benzopyranyl group, a 4H-1-benzopyranyl group, a 2H-1-benzopyranyl group, and a 1H-2-benzopyranyl group.

Specific examples of the alkyl group of 1 to 12 carbon atoms in (Ax-3) may include a methyl group, an ethyl group, a propyl group, and an isopropyl group. Specific examples of the aromatic hydrocarbon ring group of 6 to 30 carbon atoms and the aromatic heterocyclic ring group of 2 to 30 carbon atoms in (Ax-3) may include the same examples as those listed as the specific examples of them in (Ax-1) and (Ax-2).

Specific examples of the alkenyl group of 2 to 12 carbon atoms in (Ax-4) may include a vinyl group and an allyl group. Specific examples of the aromatic hydrocarbon ring group of 6 to 30 carbon atoms and the aromatic heterocyclic ring group of 2 to 30 carbon atoms in (Ax-4) may include the same examples as those listed as the specific examples of them in (Ax-1) and (Ax-2).

Specific examples of the alkynyl group of 2 to 12 carbon atoms in (Ax-5) may include an ethynyl group and a propynyl group. Specific examples of the aromatic hydrocarbon ring group of 6 to 30 carbon atoms and the aromatic heterocyclic ring group of 2 to 30 carbon atoms in (Ax-5) may include the same examples as those listed as the specific examples of them in (Ax-1) and (Ax-2).

Also included in the examples of (Ax-1) to (Ax-5) are those in which the organic groups as those listed above additionally have one or a plurality of substituents. When a plurality of substituents are included, they may be the same as or different from one another.

Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group; an N,N-dialkylamino group of 2 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; $-OCF_3$; $-C(=O)-R^b$; $-C(=O)-O-R^b$; and $-SO_2R^a$. Herein, $R^b$ and $R^a$ have the same meanings as described above.

Among these, as the substituent in (Ax-1) to (Ax-5), one or more substituents selected from a halogen atom, a cyano group, an alkyl group of 1 to 6 carbon atoms, and an alkoxy group of 1 to 6 carbon atoms are preferable.

Preferable specific examples of Ax are shown below. However, the present invention is not limited to the following. In the formulae below, "—" represents a bond with an N atom (i.e., the N atom bonded to Ax in the formulae (IIa-1) to (IIa-7) and formulae (IIb-1) to (IIb-7)) extending from any optional position in the ring.

Specific examples of the hydrocarbon ring group in (Ax-1) may include groups represented by the following formulae (1-1) to (1-20), and aromatic hydrocarbon ring groups of 6 to 30 carbon atoms represented by the formulae (1-9) to (1-20) and the like are preferable.

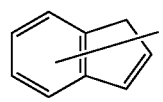

(1-1)

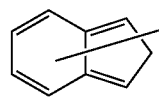

(1-2)

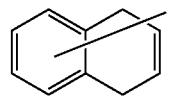

(1-3)

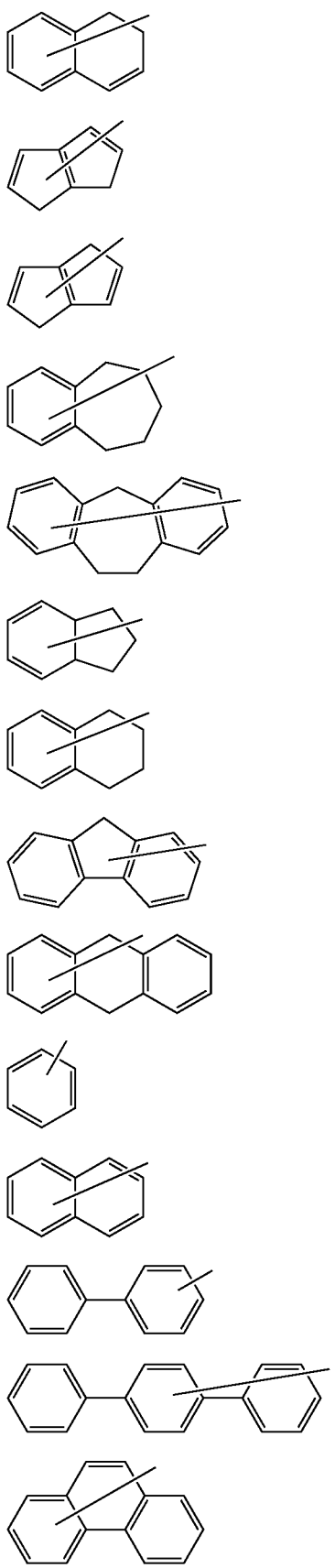
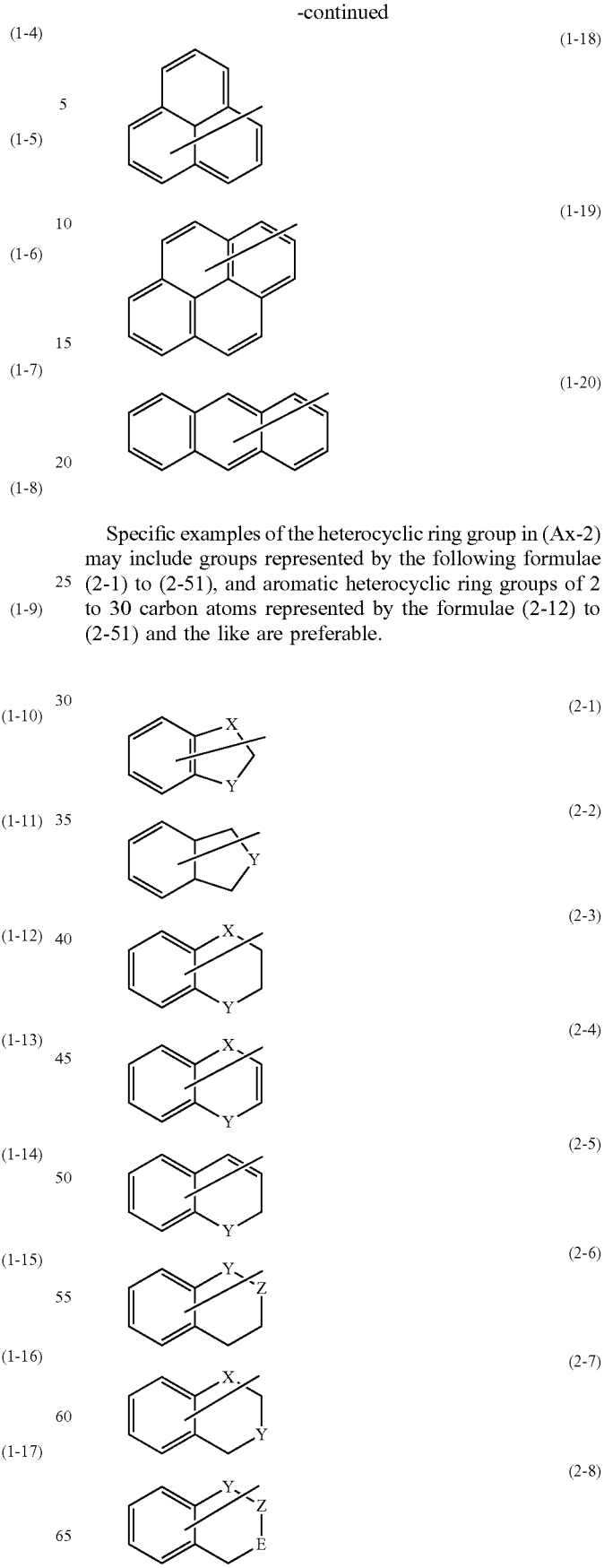
Specific examples of the heterocyclic ring group in (Ax-2) may include groups represented by the following formulae (2-1) to (2-51), and aromatic heterocyclic ring groups of 2 to 30 carbon atoms represented by the formulae (2-12) to (2-51) and the like are preferable.

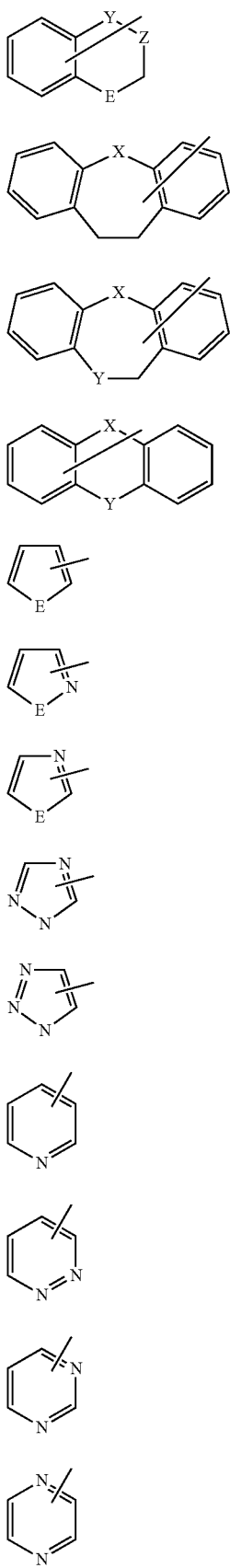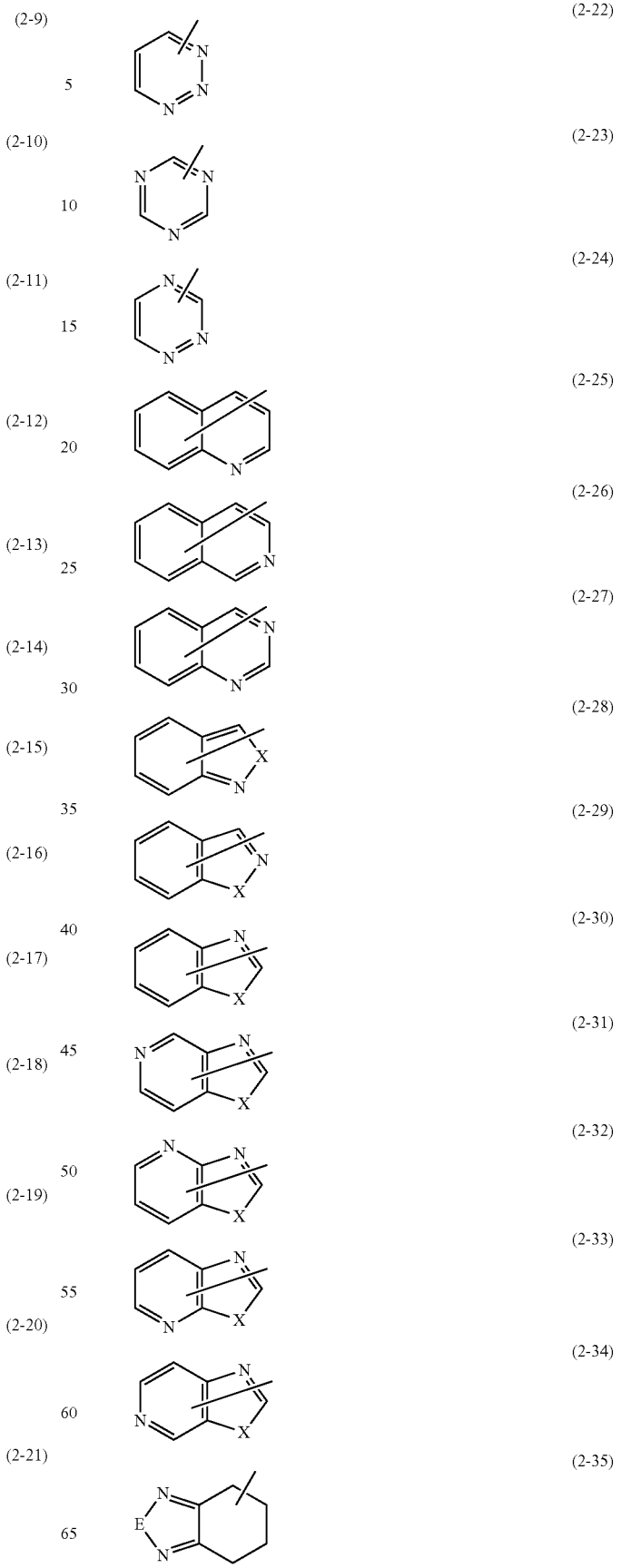

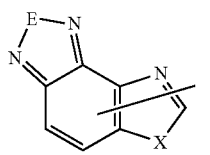 (2-36)

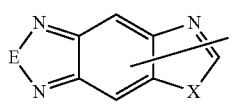 (2-37)

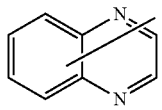 (2-38)

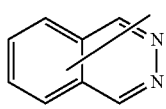 (2-39)

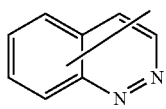 (2-40)

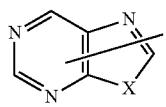 (2-41)

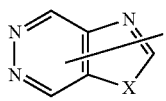 (2-42)

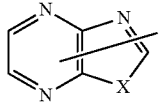 (2-43)

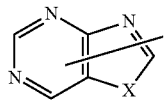 (2-44)

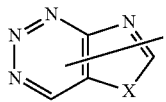 (2-45)

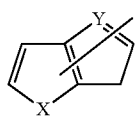 (2-46)

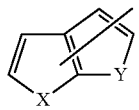 (2-47)

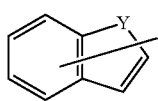 (2-48)

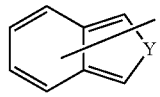 (2-49)

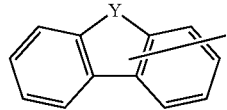 (2-50)

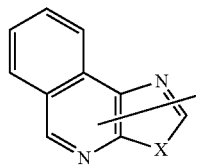 (2-51)

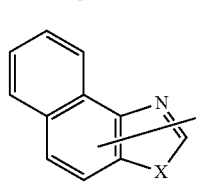 (2-52)

[In each of the formulae, X represents —CH$_2$—, —NR$^c$—, an oxygen atom, a sulfur atom, —SO—, or —SO$_2$—, Y and Z each independently represent —NR$^c$—, an oxygen atom, a sulfur atom, —SO—, or —SO$_2$—, and E represents —NR$^c$—, an oxygen atom, or a sulfur atom.

Herein, R$^c$ represents a hydrogen atom or an alkyl group of 1 to 6 carbon atoms such as a methyl group, an ethyl group, or a propyl group. (However, in each of the formulae, the oxygen atom, sulfur atom, —SO—, and —SO$_2$— each are not adjacent to each other.)]

Specific examples of the alkyl group in (Ax-3) may include groups represented by the following formulae (3-1) to (3-8).

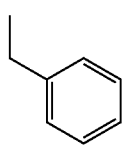 (3-1)

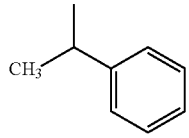 (3-2)

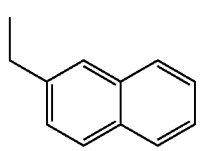 (3-3)

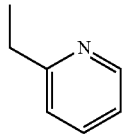 (3-4)

(3-5)

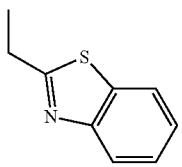

(3-6)

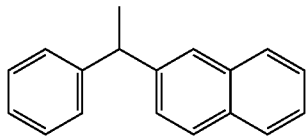

(3-7)

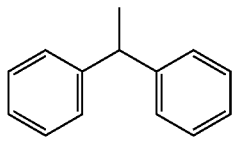

(3-8)

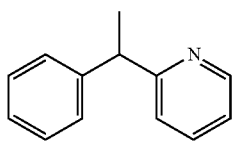

Specific examples of the alkenyl group in (Ax-4) may include groups represented by the following formulae (4-1) to (4-5).

(4-1)

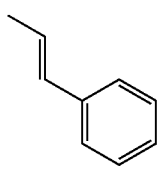

(4-2)

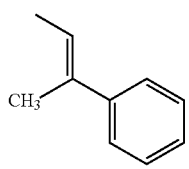

(4-3)

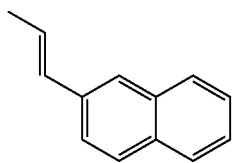

(4-4)

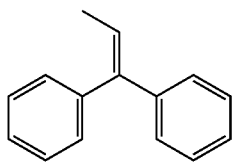

(4-5)

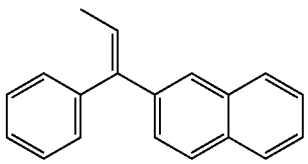

Specific examples of the alkynyl group in (Ax-5) may include groups represented by the following formulae (5-1) to (5-2).

(5-1)

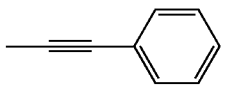

(5-2)

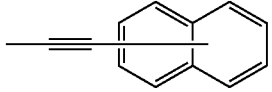

Those in which the preferable specific examples of the above-mentioned Ax further include one or a plurality of substituents on the ring may also be included in the example of Ax. When a plurality of substituents are included, the plurality of substituents may be the same as or different from one another. Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group and a pentafluoroethyl group; an N, N-dialkylamino group of 2 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; —OCF$_3$; —C(=O)—R$^b$; —C(=O)—O—R$^b$; and —SO$_2$R$^a$.

Herein, R$^b$ and R$^a$ have the same meanings as described above. Among these, as a substituent in Ax, a halogen atom, a cyano group, an alkyl group of 1 to 6 carbon atoms, and an alkoxy group of 1 to 6 carbon atoms are preferable.

Among those described above, Ax is preferably an aromatic hydrocarbon ring group of 6 to 30 carbon atoms or an aromatic heterocyclic ring group of 2 to 30 carbon atoms.

It is more preferable that Ax is an aromatic hydrocarbon ring group of 6 to 20 carbon atoms or an aromatic heterocyclic ring group of 4 to 20 carbon atoms, and it is further more preferable that Ax is any of the groups represented by the above-described formula (2-3), and formula (2-13), formula (2-15), and formula (2-30).

As mentioned above, the aforementioned ring may have one or a plurality of substituents. When a plurality of substituents are included, the plurality of substituents may be the same as or different from one another. Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group and a pentafluoroethyl group; an N, N-dialkylamino group of 1 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; —C(=O)—$R^b$; —C(=O)—O—$R^b$; and —$SO_2R^a$.

Herein, $R^b$ and $R^a$ have the same meanings as described above.

Among these, as a substituent in the aforementioned ring, a halogen atom, a cyano group, an alkyl group of 1 to 6 carbon atoms, and an alkoxy group of 1 to 6 carbon atoms are preferable.

Groups represented by the following formulae (III-1) to (III-7) are more preferable as Ax.

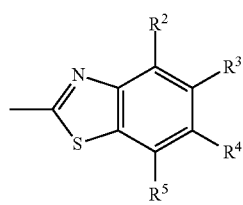
(III-1)

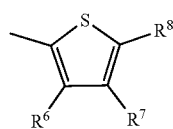
(III-2)

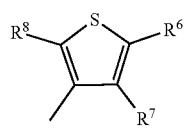
(III-3)

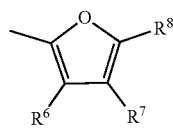
(III-4)

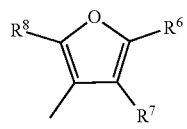
(III-5)

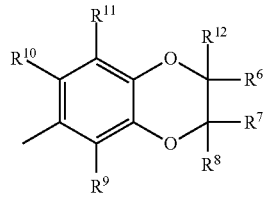
(III-6)

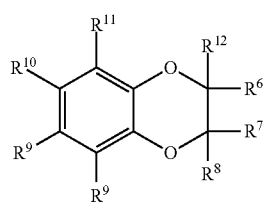
(III-7)

In the formulae (III-1) to (III-7), $R^2$ to $R^{12}$ each independently represent a hydrogen atom, a halogen atom, an alkyl group of 1 to 6 carbon atoms, a cyano group, a nitro group, a fluoroalkyl group of 1 to 6 carbon atoms, an alkoxy group of 1 to 6 carbon atoms, —$OCF_3$, or —C(=O)—O—$R^b$, and $R^b$ represents an alkyl group of 1 to 20 carbon atoms optionally having a substituent, an alkenyl group of 2 to 20 carbon atoms optionally having a substituent, a cycloalkyl group of 3 to 12 carbon atoms optionally having a substituent, or an aromatic hydrocarbon ring group of 5 to 12 carbon atoms optionally having a substituent. Among these, it is preferable that all of $R^2$ to $R^{12}$ are a hydrogen atom, or one or more of $R^2$ to $R^{12}$ are an alkoxy group of 1 to 6 carbon atoms optionally having a substituent and the remainder is a hydrogen atom.

C—$R^2$ to C—$R^5$ may be the same as or different from one another, and one or more of C—$R^2$ to C—$R^5$ constituting the ring may be replaced with a nitrogen atom.

Specific examples of the group in which one or more of C—$R^2$ to C—$R^5$ of the group represented by the aforementioned formula (III) are replaced with a nitrogen atom may include structures represented by the following formulae (III-1-1) to (III-1-8). However, the group in which one or more of C—$R^2$ to C—$R^5$ are replaced with a nitrogen atom is not limited thereto.

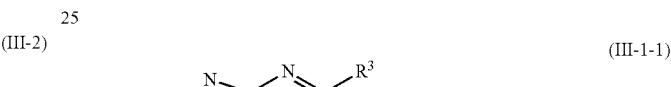
(III-1-1)

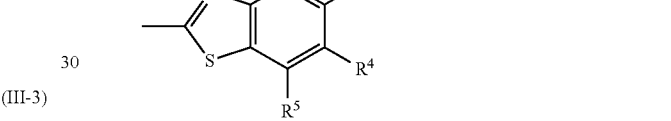
(III-1-2)

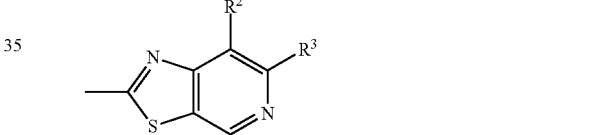
(III-1-3)

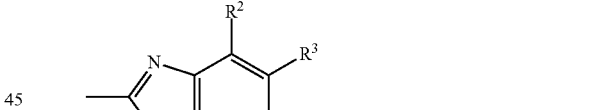
(III-1-4)

(III-1-5)

(III-1-6)

-continued

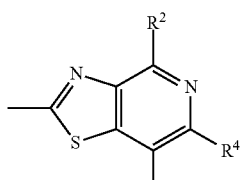
(III-1-7)

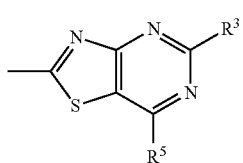
(III-1-8)

[In each of the formulae, $R^2$ to $R^5$ represent the same meanings as described above.]

When Ay is an organic group of 1 to 30 carbon atoms optionally having a substituent, examples of such an organic group may include, but are not limited to, an alkyl group of 1 to 20 carbon atoms optionally having a substituent, an alkenyl group of 2 to 20 carbon atoms optionally having a substituent, an alkynyl group of 2 to 20 carbon atoms optionally having a substituent, a cycloalkyl group of 3 to 12 carbon atoms optionally having a substituent, —SO$_2$R$^a$, —C(=O)—R$^b$, —CS—NH—R$^b$, an aromatic hydrocarbon ring group of 6 to 30 carbon atoms optionally having a substituent, and an aromatic heterocyclic ring group of 2 to 30 carbon atoms optionally having a substituent.

Herein, R$^a$ and R$^b$ have the same meanings as described above.

Specific examples of the alkyl group of 1 to 20 carbon atoms in a case where Ay is the alkyl group of 1 to 20 carbon atoms optionally having a substituent, specific examples of the alkenyl group of 2 to 20 carbon atoms in a case where Ay is the alkenyl group of 2 to 20 carbon atoms optionally having a substituent, and specific examples of the cycloalkyl group of 3 to 12 carbon atoms in a case where Ay is the cycloalkyl group of 3 to 12 carbon atoms optionally having a substituent may include the same examples as those listed as the specific examples of the alkyl group of 1 to 20 carbon atoms in a case where R$^b$ is the alkyl group of 1 to 20 carbon atoms optionally having a substituent, the specific examples of the alkenyl group of 2 to 20 carbon atoms in a case where R$^b$ is the alkenyl group of 2 to 20 carbon atoms optionally having a substituent, and the specific examples of the cycloalkyl group of 3 to 12 carbon atoms in a case where R$^b$ is the cycloalkyl group of 3 to 12 carbon atoms optionally having a substituent, as described above. Further, the number of carbon atoms of the alkyl group of 1 to 20 carbon atoms in the alkyl group of 1 to 20 carbon atoms optionally having a substituent is preferably 1 to 12, the number of carbon atoms of the alkenyl group of 2 to 20 carbon atoms in the alkenyl group of 2 to 20 carbon atoms optionally having a substituent is preferably 2 to 12, and the number of carbon atoms of the cycloalkyl group of 3 to 12 carbon atoms in the cycloalkyl group of 3 to 12 carbon atoms optionally having a substituent is preferably 3 to 10.

Specific examples of the alkynyl group of 2 to 20 carbon atoms in a case where Ay is the alkynyl group of 2 to 20 carbon atoms optionally having a substituent may include an ethynyl group, a propynyl group, a 2-propynyl group (propargyl group), a butynyl group, a 2-butynyl group, a 3-butynyl group, a pentinyl group, a 2-pentinyl group, a hexynyl group, a 5-hexynyl group, a heptynyl group, an octynyl group, a 2-octinyl group, a nonanyl group, a decanyl group, and a 7-decanyl group.

When Ay is the alkyl group of 1 to 20 carbon atoms optionally having a substituent, when Ay is the alkenyl group of 2 to 20 carbon atoms optionally having a substituent, when Ay is the cycloalkyl group of 3 to 12 carbon atoms optionally having a substituent, and when Ay is the alkynyl group of 2 to 20 carbon atoms optionally having a substituent, the number of the substituents may be one or plural. When a plurality of substituents are included, they may be the same as or different from one another. Examples of the substituent may include a halogen atom such as a fluorine atom and a chlorine atom; a cyano group; an N, N-dialkylamino group of 2 to 12 carbon atoms such as a dimethylamino group; an alkoxy group of 1 to 20 carbon atoms such as a methoxy group, an ethoxy group, an isopropoxy group, and a butoxy group; an alkoxy group of 1 to 12 carbon atoms substituted with an alkoxy group of 1 to 12 carbon atoms such as a methoxymethoxy group and a methoxyethoxy group; a nitro group; an aromatic hydrocarbon ring group of 6 to 20 carbon atoms such as a phenyl group and a naphthyl group; an aromatic heterocyclic ring group of 2 to 20 carbon atoms such as a triazoryl group, a pyrrolyl group, a furanyl group, and a thiophenyl group; a cycloalkyl group of 3 to 8 carbon atoms such as cyclopropyl group, a cyclopentyl group, and a cyclohexyl group; a cycloalkyloxy group of 3 to 8 carbon atoms such as a cyclopenthyloxy group and a cyclohexyloxy group; a cyclic ether group of 2 to 12 carbon atoms such as a tetrahydrofuranyl group, a tetrahydropyranyl group, a dioxolanyl group, and a dioxanyl group; an aryloxy group of 6 to 14 carbon atoms such as a phenoxy group and a naphthoxy group; a fluoroalkyl group of 1 to 12 carbon atoms, in which one or more hydrogen atoms are substituted by a fluorine atom, such as a trifluoromethyl group, a pentafluoroethyl group, and —CH$_2$CF$_3$; a benzofuryl group; a benzopyranyl group; a benzodioxolyl group; a benzodioxanyl group; —O—C(=O)—R$^b$; —C(=O)—R$^b$; —C(=O)—O—R$^b$; —SO$_2$R$^a$; —SR$^b$; an alkoxy group of 1 to 12 carbon atoms substituted with —SR$^b$; and a hydroxyl group. Herein, R$^a$ and R$^b$ have the same meanings as described above.

Examples of the aromatic hydrocarbon ring group, the aromatic heterocyclic ring group, and the substituent in a case where Ay is the aromatic hydrocarbon ring group of 6 to 30 carbon atoms optionally having a substituent and in a case where Ay is the aromatic heterocyclic ring group of 2 to 30 carbon atoms optionally having a substituent may include the same examples as those listed as the specific examples of them included in Ax. Among these examples, when Ay has a substituent, the number of substituents may be one or plural. When a plurality of substituents are included, they may be the same as or different from one another. The number of carbon atoms of the aromatic hydrocarbon ring group in these examples is preferably 6 to 20, more preferably 6 to 18, and still more preferably 6 to 12. The number of carbon atoms of the aromatic heterocyclic ring group in these examples is preferably 2 to 20, and more preferably 2 to 18.

Among those described above, Ay is preferably a hydrogen atom, an alkyl group of 1 to 20 carbon atoms optionally having a substituent, an alkenyl group of 2 to 20 carbon atoms optionally having a substituent, an alkynyl group of 2 to 20 carbon atoms optionally having a substituent, a cycloalkyl group of 3 to 12 carbon atoms optionally having a substituent, an aromatic hydrocarbon ring group of 6 to 18 carbon atoms optionally having a substituent, or an aromatic heterocyclic ring group of 2 to 18 carbon atoms optionally having a substituent. Further, Ay is more preferably a hydrogen atom, an alkyl group of 1 to 18 carbon atoms optionally having a substituent, an alkenyl group of 2 to 18 carbon atoms optionally having a substituent, an alkynyl group of 2 to 18 carbon atoms optionally having a substituent, a cycloalkyl group of 3 to 10 carbon atoms optionally having a substituent, an aromatic hydrocarbon ring group of 6 to 12 carbon atoms optionally having a substituent, or an aromatic heterocyclic ring group of 2 to 18 carbon atoms optionally having a substituent. Among these, an alkyl group of 1 to 18 carbon atoms optionally having a substituent is particularly preferable as Ay, and an alkyl group of 2 to 12 carbon atoms optionally having a substituent is particularly more preferable.

Examples of Az may include the following (Az-6) to (Az-7):
- (Az-6) a hydrocarbon ring group of 6 to 40 carbon atoms having one or more aromatic hydrocarbon rings having 6 to 30 carbon atoms; and
- (Az-7) a heterocyclic ring group of 2 to 40 carbon atoms having one or more aromatic rings selected from the group consisting of an aromatic hydrocarbon ring of 6 to 30 carbon atoms and an aromatic heterocyclic ring of 2 to 30 carbon atoms.

Preferable specific examples of Az will be shown below. However, the present invention is not limited to the following. In the formula below, "=" represents a bond with an N atom (i.e., an N atom bonded to Az in the formulae (IIc-1) to (IIc-7)) extending from any optional position of the ring.

Specific examples of the hydrocarbon ring group in (Az-6) may include structures represented by the following formulae (6-1) to (6-12), and aromatic hydrocarbon ring groups of 6 to 30 carbon atoms represented by the formulae (6-1), (6-3) to (6-4), and (6-7) to (6-12) are preferable.

(6-1)

(6-2)

(6-3)

(6-4)

(6-5)

(6-6)

(6-7)
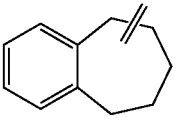

(6-8)
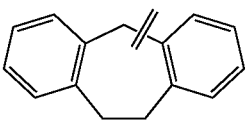

(6-9)
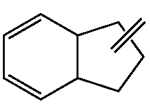

(6-10)
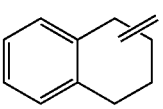

(6-11)
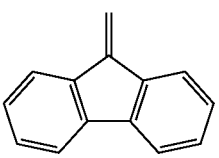

(6-12)
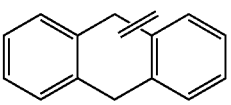

Specific examples of the heterocyclic ring group in (Az-7) may include structures represented by the following formulae (7-1) to (7-30), and aromatic heterocyclic ring groups of 2 to 30 carbon atoms represented by the formulae (7-1) to (7-11) are preferable.

(7-1)
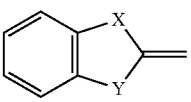

(7-2)
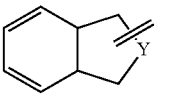

(7-3)
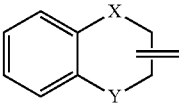

(7-4)
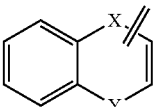

(7-5)
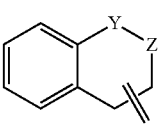

-continued
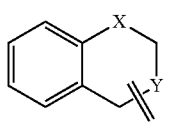 (7-6)
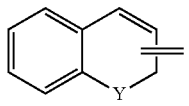 (7-7)
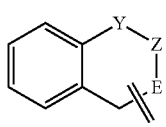 (7-8)
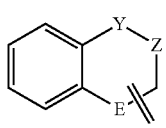 (7-9)
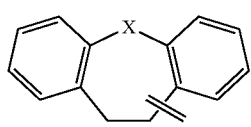 (7-10)
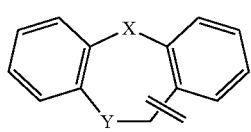 (7-11)
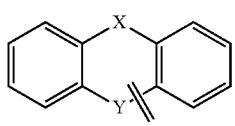 (7-12)
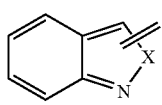 (7-13)
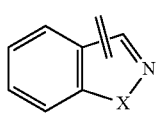 (7-14)
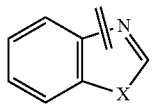 (7-15)
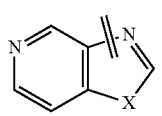 (7-16)
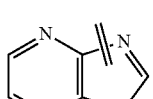 (7-17)
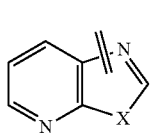 (7-18)
-continued
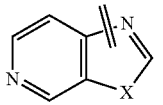 (7-19)
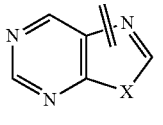 (7-20)
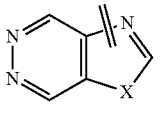 (7-21)
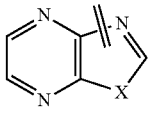 (7-22)
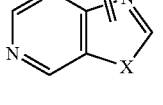 (7-23)
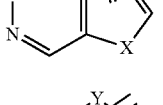 (7-24)
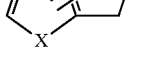 (7-25)
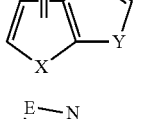 (7-26)
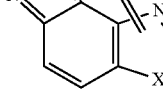 (7-27)
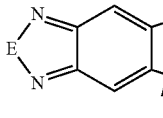 (7-28)
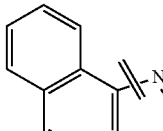 (7-29)
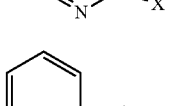 (7-30)
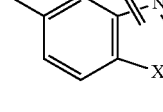

[In each of the formulae, X represents —CH₂—, —NR^c—, an oxygen atom, a sulfur atom, —SO—, or —SO₂—, Y and Z each independently represent —NR^c—, an oxygen atom, a sulfur atom, —SO—, or —SO₂—, and E represents —NR^c—, an oxygen atom, or a sulfur atom. Herein, R^c represents a hydrogen atom or an alkyl group of 1 to 6 carbon atoms such as a methyl group, an ethyl group, or a propyl group. (However, in each of the formulae, the oxygen atom, sulfur atom, —SO—, and —SO₂— each are not adjacent to each other.)]

Those in which the preferable examples of the abovementioned Az further include one or a plurality of substituents on the ring may also be included in the example of Az. When a plurality of substituents are included, the plurality of substituents may be the same as or different from one another. Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group; an N, N-dialkylamino group of 1 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; —OCF₃; —C(=O)—R^b; —C(=O)—O—R^b; and —SO₂R^a. Herein, R^b and R^a have the same meanings as described above. Among these, as a substituent in the aforementioned ring in Az, a halogen atom, a cyano group, an alkyl group of 1 to 6 carbon atoms, and an alkoxy group of 1 to 6 carbon atoms are preferable.

Among those described above, Az is preferably a hydrocarbon ring group of 6 to 40 carbon atoms having one or more aromatic hydrocarbon ring group of 6 to 30 carbon atoms or a hydrocarbon ring group heterocyclic ring group of 2 to 40 carbon atoms having one or more aromatic heterocyclic rings of 2 to 30 carbon atoms.

Further, Az is more preferably a hydrocarbon ring group of 6 to 40 carbon atoms having one or more aromatic hydrocarbon rings of 6 to 30 carbon atoms, and more preferably any of the groups represented by the above-described formula (6-1), formula (6-3), formula (6-4), formula (6-10), and formula (7-1) to formula (7-9).

As mentioned above, the aforementioned ring may have one or a plurality of substituents. When a plurality of substituents are included, the plurality of substituents may be the same as or different from one another. Examples of such a substituent may include a halogen atom such as a fluorine atom and a chlorine atom; a cyano group; an alkyl group of 1 to 6 carbon atoms such as a methyl group, an ethyl group, and a propyl group; an alkenyl group of 2 to 6 carbon atoms such as a vinyl group and an allyl group; a halogenated alkyl group of 1 to 6 carbon atoms such as a trifluoromethyl group and a pentafluoroethyl group; an N, N-dialkylamino group of 1 to 12 carbon atoms such as a dimethylamino group; an alkoxy group of 1 to 6 carbon atoms such as a methoxy group, an ethoxy group, and an isopropoxy group; a nitro group; an aromatic hydrocarbon ring group of 6 to 20 carbon atoms such as a phenyl group and a naphthyl group; —C(=O)—R^b; —C(=O)—O—R^b; and —SO₂R^a.

Herein, R^b and R^a have the same meanings as described above.

Among these, as a substituent in the aforementioned ring, a halogen atom, a cyano group, an alkyl group of 1 to 6 carbon atoms, and an alkoxy group of 1 to 6 carbon atoms are preferable.

Groups represented by the following formulae (V-1) to (V-4) are more preferable as Az.

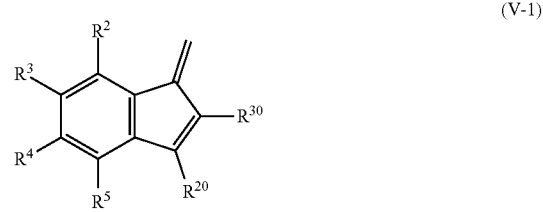

(V-1)

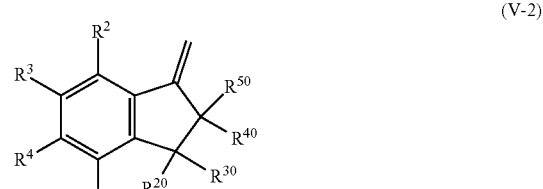

(V-2)

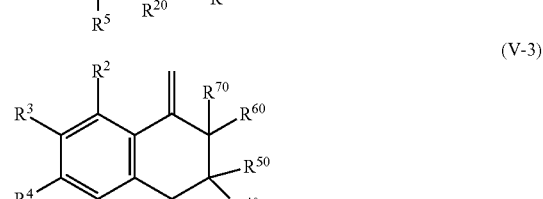

(V-3)

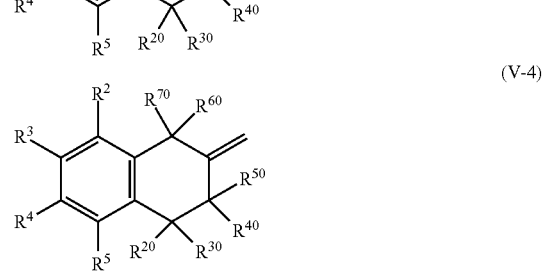

(V-4)

In the formulae (V-1) to (V-4), $R^2$ to $R^5$ and $R^{20}$, $R^{30}$, $R^{40}$, $R^{50}$, $R^{60}$, and $R^{70}$ each independently represent a hydrogen atom, a halogen atom, an alkyl group of 1 to 6 carbon atoms, a cyano group, a nitro group, a fluoroalkyl group of 1 to 6 carbon atoms, an alkoxy group of 1 to 6 carbon atoms, —OCF₃, or —C(=O)—O—R^b, and R^b represents an alkyl group of 1 to 20 carbon atoms optionally having a substituent, an alkenyl group of 2 to 20 carbon atoms optionally having a substituent, a cycloalkyl group of 3 to 12 carbon atoms optionally having a substituent, or an aromatic hydrocarbon ring group of 5 to 12 carbon atoms optionally having a substituent. Among these, it is preferable that all of $R^2$ to $R^{11}$ are a hydrogen atom, or one or more of $R^2$ to $R^{11}$ are an alkoxy group of 1 to 6 carbon atoms optionally having a substituent and the remainder is a hydrogen atom.

In the aforementioned formula (I), $Z^1$ and $Z^2$ are each independently a single bond, —O—, —O—CH₂—, —CH₂—O—, —O—CH₂—CH₂, —CH₂—CH₂—O—, —C(=O)—O—, —O—C(=O)—, —C(=O)—S—, —S—C(=O)—, —NR²¹—C(=O)—, —C(=O)—NR²¹—, —CF₂—O—, —O—CF₂—, —CH₂—CH₂—, —CF₂—CF₂—, —O—CH₂—CH₂—O—, —CH=CH—C(=O)—O—, —O—C(=O)—CH=CH—, —CH₂—C(=O)—O—, —O—C(=O)—CH₂—, —CH₂—O—C (=O)—, —C(=O)—O—CH$_2$—, —CH$_2$—CH$_2$—C(=O)—O—, —O—C(=O)—CH$_2$—CH$_2$—, —CH$_2$—CH$_2$—O—C(=O)—, —C(=O)—O—CH$_2$—CH$_2$—, —CH=CH—, —N=CH—, —CH=N—, —N=C(CH$_3$)—, —C(CH$_3$)=N—, —N=N—, or —C≡C—, and R$^{21}$ independently represents a hydrogen atom or an alkyl group of 1 to 6 carbon atoms.

Among these, it is preferable that Z$^1$ and Z$^2$ are each independently —C(=O)—O— or —O—C(=O)—.

In the aforementioned formula (I), G$^1$ and G$^2$ are each independently any of organic groups that are an aliphatic hydrocarbon group of 1 to 20 carbon atoms and a group in which one or more methylene groups (—CH$_2$—) contained in an aliphatic hydrocarbon group of 3 to 20 carbon atoms are substituted by —O— or —C(=O)—, and hydrogen atoms in the organic groups of G$^1$ and G$^2$ may be substituted with one or more substituents selected from the group consisting of an alkyl group of 1 to 5 carbon atoms, an alkoxy group of 1 to 5 carbon atoms, and a halogen atom. The substitution of the methylene group by —O— or —C(=O)— is preferably substitution of a methylene group other than the methylene group directly connected to any of P1, P2, Y3, and Y4. For example, a group in which one of methylene groups (—CH$_2$—) in an aliphatic hydrocarbon group of three carbon atoms is substituted by —O— is preferably —CH$_2$—O—CH$_2$—. In "a group in which one or more methylene groups (—CH$_2$—) contained in an aliphatic hydrocarbon group of 1 to 20 carbon atoms are substituted by —O— or —C(=O)—", —O— preferably does not substitute for the continuous methylene groups in the aliphatic hydrocarbon group (i.e., does not form the structure of —O—O—), and —C(=O)— preferably does not substitute for the continuous methylene groups in the aliphatic hydrocarbon group (i.e., does not form the structure of —C(=O)—C(=O)—).

When G$^1$ and G$^2$ are an aliphatic hydrocarbon group of 1 to 20 carbon atoms, specific examples thereof are not particularly limited but may include a chain aliphatic hydrocarbon group such as an alkylene group of 1 to 20 carbon atoms, an alkenylene group of 1 to 20 carbon atoms, and an alkynylene group of 1 to 20 carbon atoms. The number of carbon atoms of the aliphatic hydrocarbon group described above is preferably 3 to 12, and more preferably 4 to 10.

Herein, as the organic group which is the example of G$^1$ and G$^2$, an alkylene group of 1 to 20 carbon atoms optionally being substituted with a fluorine atom, or a group represented by —(CH$_2$)$_j$—C(=O)—O—(CH$_2$)$_k$— optionally being substituted with a fluorine atom (in which j and k each represent an integer of 2 to 12 and preferably represent an integer of 2 to 8) is preferable. As the organic group, an alkylene group of 2 to 12 carbon atoms optionally being substituted with a fluorine atom is more preferable, an unsubstituted alkylene group of 2 to 12 carbon atoms is more preferable, and a group represented by —(CH$_2$)$_l$— (in the formula, l represents an integer of 2 to 12 and preferably represents an integer of 2 to 8) is particularly preferable.

In the aforementioned formula (I), A$^1$, A$^2$, B$^1$, and B$^2$ each independently represent a cyclic aliphatic group optionally having a substituent or an aromatic group optionally having a substituent, and a cyclic aliphatic group of 5 to 20 carbon atoms optionally having a substituent or an aromatic group of 2 to 20 carbon atoms optionally having a substituent is preferable.

Specific examples of the cyclic aliphatic group may include a cycloalkanediyl group of 5 to 20 carbon atoms such as a cyclopentane-1,3-diyl group, a cyclohexane-1,4-diyl group, a cycloheptane-1,4-diyl group, and a cyclooctane-1,5-diyl group; and a bicycloalkanediyl group of 5 to 20 carbon atoms such as a decahydronaphthalene-1,5-diyl group, and a decahydronaphthalene-2,6-diyl group. Among these, as the cyclic aliphatic group, a cycloalkanediyl group of 5 to 20 carbon atoms optionally being substituted is preferable, a cyclohexanediyl group is more preferable, and a cyclohexane-1,4-diyl group represented by the following formula (a) is particularly preferable. The cyclic aliphatic group may be a trans isomer represented by the formula (a1), a cis isomer represented by the formula (a2), or a mixture of a cis isomer and a trans isomer, and a trans isomer represented by the formula (a1) is more preferable.

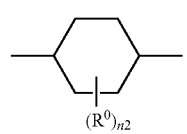

(a)

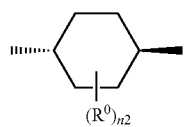

(a1)

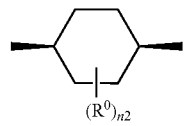

(a2)

(In the formula, R$^0$ and n2 represent the same meanings as described above.)

Specific examples of the aromatic group may include an aromatic hydrocarbon ring group of 6 to 20 carbon atoms such as a 1,2-phenylene group, a 1,3-phenylene group, a 1,4-phenylene group, a 1,4-naphthylene group, a 1,5-naphthylene group, a 2,6-naphthylene group, and a 4,4'-biphenylene group; and an aromatic heterocyclic ring group of 2 to 20 carbon atoms such as a furan-2,5-diyl group, a thiophene-2,5-diyl group, a pyridine-2,5-diyl group, and a pyrazine-2,5-diyl group. Among these, as the aromatic group, an aromatic hydrocarbon ring group of 6 to 20 carbon atoms is preferable, a phenylene group is more preferable, and a 1,4-phenylene group represented by the following formula (b) is particularly preferable.

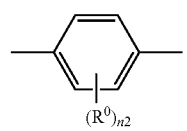

(b)

(In the formula, R$^0$ and n2 represent the same meanings as described above.)

Examples of the substituents of the cyclic aliphatic group and the aromatic group may include a halogen atom such as a fluorine atom, a chlorine atom, and a bromine atom: an alkyl group of 1 to 6 carbon atoms such as a methyl group and an ethyl group; an alkoxy group of 1 to 5 carbon atoms such as a methoxy group and an isopropoxy group; a nitro group; and a cyano group. The cyclic aliphatic group, the cyclic aliphatic group of 5 to 20 carbon atoms, the aromatic group, and the aromatic group of 2 to 20 carbon atoms may have one or more substituents selected from the substituents described above. When a plurality of substituents are included, the respective substituents may be the same as or different from one another.

In the aforementioned formula (I), $Y^1$ to $Y^4$ each independently represent a single bond, —O—, —C(=O)—, —C(=O)—O—, —O—C(=O)—, —NR$^{22}$—C(=O)—, —C(=O)—NR$^{22}$—, —O—C(=O)—O—, —NR$^{22}$—C(=O)—O—, —O—C(=O)—NR$^{22}$—, or —NR$^{22}$—C(=O)—NR$^{23}$—. Herein, $R^{22}$ and $R^{23}$ each independently represent a hydrogen atom or an alkyl group of 1 to 6 carbon atoms.

Among these, it is preferable that $Y^1$ to $Y^4$ are each independently —O—, —C(=O)—, —C(=O)—O—, —O—C(=O)—O—, or —O— C(=O)—.

When a plurality of $Y^1$ and $Y^2$ are present, they may be the same as or different from one another.

In the aforementioned formula (I), one of $P^1$ and $P^2$ represents a hydrogen atom or a polymerizable group, and the other of $P^1$ and $P^2$ represents a polymerizable group. Herein, it is preferable that $P^1$ and $P^2$ each independently represent a polymerizable group.

Herein, examples of the polymerizable group in a case where $P^1$ and $P^2$ are a polymerizable group may include a group represented by $CH_2$=$CR^1$—C(=O)—O— ($R^1$ represents a hydrogen atom, a methyl group, or a chlorine atom) such as an acryloyloxy group or a methacryloyloxy group, a vinyl group, a vinyl ether group, a p-stilbene group, an acryloyl group, a methacryloyl group, a carboxyl group, a methylcarbonyl group, a hydroxyl group, an amido group, an alkylamino group of 1 to 4 carbon atoms, an amino group, an epoxy group, an oxetanyl group, an aldehyde group, an isocyanate group, and a thioisocyanate group. Among these, a group represented by $CH_2$=$CR^1$—C(=O)—O— as shown in the following formula (IV) is preferable, $CH_2$=CH—C(=O)—O— (acryloyloxy group) and $CH_2$=C($CH_3$)—C(=O)—O— (methacryloyloxy group) are more preferable, and acryloyloxy group is further more preferable. When two $R^1$'s are present in the polymerizable compound (I), they may be the same as or different from each other. In addition, $P^1$ and $P^2$ may be different from each other, and are preferably the same polymerizable group.

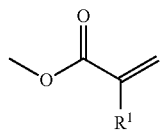

(IV)

[In the formula (IV), $R^1$ represents a hydrogen atom, a methyl group, or a chlorine atom.]

In the formula (I), p and q are each independently 0 to 2, and are each independently preferably 0 or 1.

Preferable examples of the liquid crystal compound represented by the formula (I) may include compounds represented by the formulae LC1 to LC3 below.

LC1

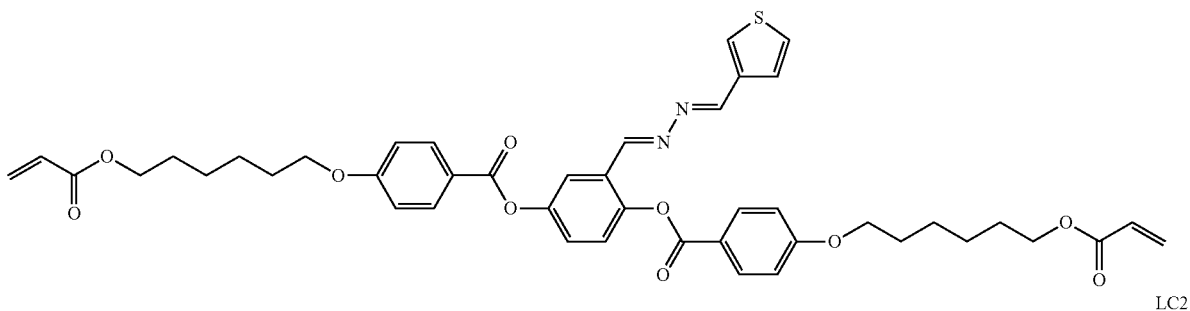

LC2

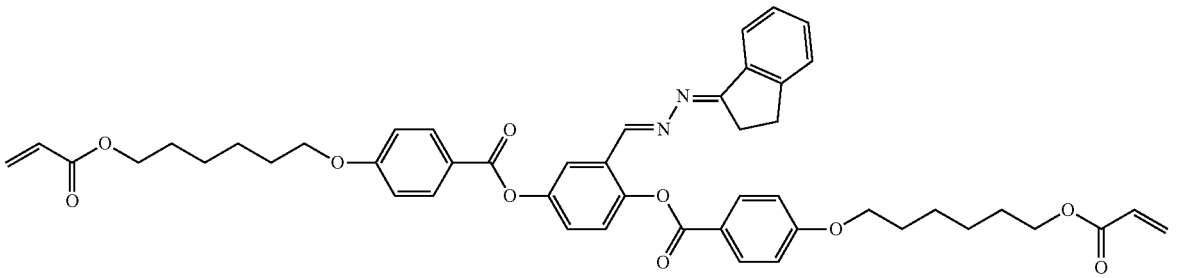

LC3

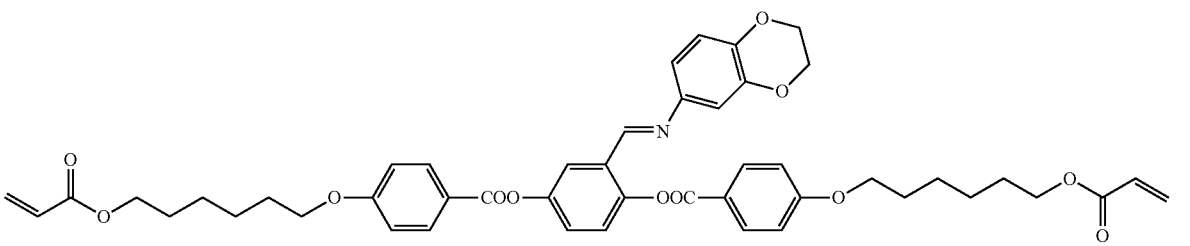

The liquid crystal compound represented by the formula (I) may be prepared by combining synthetic techniques described in literatures such as, for example, International Publication Nos. 2012/141245, 2012/147904, 2014/010325, and 2014/126113, and other known synthetic techniques.

The liquid crystal composition used for producing the phase difference plate of the present invention may be produced by mixing a liquid crystal compound such as those described above, a photopolymerization initiator, a surfactant, an organic solvent, and other optional components.

The photopolymerization initiator may be appropriately selected in accordance with the type of the polymerizable group of the polymerizable compound in the liquid crystal composition. For example, a radical polymerization initiator may be used if the polymerizable group is a radical polymerizable group, an anionic polymerization initiator may be used if the polymerizable group is an anionic polymerizable group, and a cationic polymerization initiator may be used if the polymerizable group is a cationic polymerizable group.

Examples of the radical polymerization initiator may include a photo-radical generator which is a compound that generates an active species capable of initiating polymerization of a polymerizable compound by light irradiation.

Examples of the photo-radical generator may include an acetophenone-based compound, a biimidazole-based compound, a triazine-based compound, an O-acyloxime-based compound, an onium salt-based compound, a benzoin-based compound, a benzophenone-based compound, an α-diketone-based compound, a polynuclear quinone-based compound, a xanthone-based compound, a diazo-based compound, and an imidosulfonate-based compound, which are described in International Publication No. 2012/147904.

Examples of the anionic polymerization initiator may include an alkyllithium compound; a monolithium salt or a monosodium salt of biphenyl, naphthalene, pyrene and the like; and a multifunctional initiator such as a dilithium salt and a tri-lithium salt.

Examples of the cationic polymerization initiator may include a protonic acid such as sulfuric acid, phosphoric acid, perchloric acid, and trifluoromethanesulfonic acid; a Lewis acid such as boron trifluoride, aluminum chloride, titanium tetrachloride, and tin tetrachloride; and an aromatic onium salt or a combination system of an aromatic onium salt and a reducing agent.

Specific examples of commercially available photopolymerization initiators may include product name: Irgacure 907, product name: Irgacure 184, product name: Irgacure 369, product name: Irgacure 651, product name: Irgacure 819, product name: Irgacure 907, product name: Irgacure 379, product name: Irgacure 379EG, and product name: Irgacure OXE02, which are manufactured by BASF; and product name: Adeca Optomer N1919 manufactured by ADEKA Corporation.

As the photopolymerization initiators, one type thereof may be solely used, and two or more types thereof may also be used in combination at any ratio.

The ratio of the photopolymerization initiator is preferably 0.1 part by weight to 10 parts by weight, and more preferably 1.0 part by weight to 7.0 parts by weight, relative to 100 parts by weight of the polymerizable compound. When two or more types of the photopolymerization initiators are used, use thereof may be practiced with the total weight thereof falling within the above-described range.

The surfactant is not particularly limited, and is preferably a nonionic surfactant. Commercially available products may be used as the nonionic surfactant. For example, a nonionic surfactant which is an oligomer with a molecular weight of several thousands may be used. Specific examples of these surfactants may include PolyFox "PF-151N", "PF-636", "PF-6320", "PF-656", "PF-6520", "PF-3320", "PF-651", and "PF-652" available from OMNOVA; Ftergent "FTX-209F", "FTX-208G", "FTX-204D", and "601AD" available from NEOS; Surflon "KH-40" and "S-420" available from AGC Seimi Chemical Co., Ltd.; and "MEGAFACE F-562" available from DIC Corporation. As the surfactant, one type thereof may be solely used, and two or more types thereof may also be used in combination at any ratio. The ratio of the surfactant is preferably 0.001 part by weight to 10 parts by weight, and more preferably 0.001 part by weight to 0.1 part by weight, relative to 100 parts by weight of the polymerizable compound.

Examples of the organic solvent may include a hydrocarbon solvent such as cyclopentane and cyclohexane; a ketone solvent such as cyclopentanone, cyclohexanone, methyl ethyl ketone, acetone, and methyl isobutyl ketone; an acetic acid ester solvent such as butyl acetate and amyl acetate; a halogenated hydrocarbon solvent such as chloroform, dichloromethane, and dichloroethane; an ether solvent such as 1,4-dioxane, cyclopentylmethyl ether, tetrahydrofuran, tetrahydropyran, 1,3-dioxolane, and 1,2-dimethoxyethane; an aromatic hydrocarbon solvent such as toluene, xylene, and mesitylene; and a mixture thereof. The boiling point of the solvent is preferably 60° C. to 250° C., and more preferably 60° ° C. to 150° C., from the viewpoint of excellent handling properties. The amount of the solvent used is preferably 100 parts by weight to 1000 parts by weight relative to 100 parts by weight of the polymerizable compound.

The liquid crystal composition may further contain optional components such as metal, a metal complex, a dye, a pigment, a fluorescent material, a phosphorescent material, a leveling agent, a thixotropic agent, a gelling agent, polysaccharides, an ultraviolet absorber, an infrared absorber, an antioxidant, an ion exchange resin, a metal oxide such as titanium oxide, and the like. The ratio of each of such optional additives is preferably 0.1 part by weight to 20 parts by weight relative to 100 parts by weight of the polymerizable compound.

The layer of the liquid crystal composition may be formed by applying the liquid crystal composition onto the surface of the support body. As the support body, a support body having a surface capable of expressing an orientation regulating force to the liquid crystal compound may be appropriately selected. For example, a variety of support bodies such as a substrate of a resin film, a glass plate, or the like, to the surface of which an orientation regulating force is imparted by rubbing treatment, those to the surface of which an orientation regulating force is imparted by stretching treatment, and those on the surface of which a layer having an orientation regulating force is provided may be used. As the support body, a phase difference plate P1 (to be described later) having a surface with an orientation regulating force may also be used. The application operation may be performed by, for example, a bar coating using a wire bar, a gravure coating using a gravure roller, a die coating using a coating dies, and other methods such as a curtain coating method, an extrusion coating method, a roll coating method, a spin coating method, a dip coating method, a spray coating method, a slide coating method, a print coating method, a gap coating method, and a dipping method. The thickness of the layer of the liquid crystal composition may be appropriately adjusted to obtain a phase difference plate having desired thickness and optical characteristics.

The orientation of the liquid crystal compound in the liquid crystal composition may be performed by leaving the layer of the liquid crystal composition in an environment controlled to an appropriate temperature. For example, an orientation treatment may be achieved by placing a layer of a liquid crystal composition in a 65-110° C. environment for 5 seconds to 2 minutes and then further leaving it for 5 seconds to 2 hours at a room temperature to 45° C.

The method for curing the liquid crystal composition is not particularly limited, and a method suitable for the liquid crystal composition to be treated may be appropriately selected. For example, when the liquid crystal compound and/or a polymerization initiator include a compound capable of initiating polymerization by irradiation with ultraviolet rays, the liquid crystal compound can be polymerized by irradiation with ultraviolet rays to achieve curing.

[3. Multilayer Phase Difference Plate]

The multilayer phase difference plate of the present invention includes a phase difference plate $P^1$ and a phase difference plate $P^2$, and, of these, the phase difference plate $P^2$ is the aforementioned phase difference plate of the present invention.

In the multilayer phase difference plate of the present invention, an in-plane slow axis of the phase difference plate $P^1$ is orthogonal to an in-plane slow axis of the phase difference plate $P^2$. In this configuration, the in-plane retardation of the multilayer phase difference plate is composed as a difference between the phase difference of the phase difference plate $P^1$ and the phase difference of the phase difference plate $P^2$. That is, when a slow axis direction of a multilayer phase difference plate Ps is set to the same direction as that of the phase difference plate $P^1$, an in-plane retardation RePs($\lambda$) of the multilayer phase difference plate Ps, an in-plane retardation ReP2($\lambda$) of the phase difference plate $P^2$, and an in-plane retardation ReP1($\lambda$) of the phase difference plate $P^1$ at a wavelength $\lambda$ have a relationship of RePs($\lambda$)=ReP1($\lambda$)−ReP2($\lambda$).

Regarding the multilayer phase difference plate of the present invention, ReP1($\lambda$) and ReP2($\lambda$) satisfy the following formulae (e4) and (e5).

$$ReP1(550)>ReP2(550) \quad (e4)$$

$$ReP1(400)/ReP1(700)<ReP2(400)/ReP2(700) \quad (e5)$$

When the in-plane slow axis of the phase difference plate P1 is orthogonal to the in-plane slow axis of the phase difference plate P2 and ReP1($\lambda$) and ReP2($\lambda$) satisfy the formulae (e4) and (e5), the multilayer phase difference plate can function as a wavelength plate such as a ¼ wavelength plate having a slow axis in the same direction as that of the in-plane slow axis of the phase difference plate P1. Further, by adopting the aforementioned phase difference plate of the present invention as the phase difference plate P2, a wavelength plate having a wavelength distribution with little deviation from an ideal distribution can be easily constituted.

Regarding the multilayer phase difference plate of the present invention, it is preferable that ReP1($\lambda$) satisfies the following formula (e6).

$$ReP1(400)/ReP1(700)<1.10 \quad (e6)$$

That is, the value of ReP1(400)/ReP1(700) is less than 1.10. The value of ReP1(400)/ReP1(700) is preferably 1.08 or less, and more preferably 1.06 or less, and is preferably 0.95 or more, and more preferably 1.00 or more.

When ReP1($\lambda$) satisfies the formula (e6), a wavelength plate having a wavelength distribution with little deviation from an ideal distribution can be easily constituted. In particular, when the phase difference plate P2 satisfying the aforementioned formula (e2) is adopted and this is combined with the phase difference plate P1 satisfying the formula (e6), a wavelength plate having a wavelength distribution with little deviation from an ideal distribution can be easily constituted. Further, the phase difference plate P1 satisfying the formula (e6) can be easily constituted using a known material such as a stretched product of a film made of a resin containing an alicyclic structure-containing polymer.

Regarding the multilayer phase difference plate of the present invention, it is preferable that ReP1($\lambda$) and ReP2($\lambda$) satisfy the following formula (e7).

$$90 \text{ nm}<ReP1(550)-ReP2(550)<160 \text{ nm} \quad (e7)$$

When the formula (e7) is satisfied, the multilayer phase difference plate of the present invention may be preferably constituted as a ¼ wavelength plate. More specifically, the multilayer phase difference plate may be constituted as a ¼ wavelength plate which has a slow axis in the same direction as the slow axis direction of the phase difference plate P1 and a wavelength distribution with little deviation from an ideal distribution. The value of ReP1(550)−ReP2(550) is preferably more than 90 nm, and more preferably 120 nm or more, and is preferably less than 160 nm, and more preferably 150 nm or less.

In the multilayer phase difference plate satisfying the formula (e7), each of ReP1($\lambda$) and ReP2($\lambda$) may be adjusted to a desired phase difference by adjusting a film formation method such as a material, thickness, and stretching ratio of the phase difference plate P1 and the phase difference plate P2. Further, it is preferable that ReP1($\lambda$) and ReP2($\lambda$) of the multilayer phase difference plate satisfy the following formulae (e8) and (e9).

$$180 \text{ nm}\leq ReP1(550)\leq 350 \text{ nm} \quad (e8)$$

$$90 \text{ nm}\leq ReP2(550)\leq 160 \text{ nm} \quad (e9)$$

When ReP1(550) and ReP2(550) satisfy the formulae (e8) and (e9), the phase difference plate $P^1$ can function as a ½ wavelength plate and the phase difference plate $P^2$ can function as a ¼ wavelength plate. Further, the multilayer phase difference plate formed by combining them can function as a ¼ wavelength plate having a wavelength distribution with little deviation from an ideal distribution. The value of ReP1(550) is preferably 180 nm or more, and more preferably 220 nm or more, and is preferably 350 nm or less, and more preferably 300 nm or less. The value of ReP2(550) is preferably 90 nm or more, and more preferably 120 nm or more, and is preferably 160 nm or less, and more preferably 150 nm or less.

[4. Material for Phase Difference Plate $P^1$]

The material constituting the phase difference plate $P^1$ is not particularly limited, and any material that can be used for optical applications and satisfies the above-described requirements may be used. In a preferable example, the phase difference plate P1 is a stretched product of a film of a resin containing an alicyclic structure-containing polymer. By stretching the film of the resin containing an alicyclic structure-containing polymer, the phase difference plate P1 described above can be easily obtained, and as a result, the multilayer phase difference plate of the present invention can be easily produced. The film of the resin containing an alicyclic structure-containing polymer may be a film composed of a resin containing an alicyclic structure-containing polymer.

The alicyclic structure-containing polymer is a polymer having an alicyclic structure in a repeating unit, and is usually an amorphous polymer. As the alicyclic structure-containing polymer, any of a polymer containing an alicyclic structure in a main chain and a polymer containing an alicyclic structure in a side chain may be used.

Examples of the alicyclic structure may include a cycloalkane structure and a cycloalkene structure, and a cycloalkane structure is preferable from the viewpoint of thermal stability and the like.

The number of carbon atoms constituting the repeating unit of one alicyclic structure is not particularly limited, and is preferably 4 or more, more preferably 5 or more, and particularly preferably 6 or more, and is preferably 30 or less, more preferably 20 or less, and particularly preferably 15 or less.

The ratio of the repeating units having an alicyclic structure in the alicyclic structure-containing polymer may be appropriately selected depending on the purpose of use, and is preferably 50% by weight or more, more preferably 70% by weight or more, and particularly preferably 90% by weight or more. By increasing the number of repeating units having an alicyclic structure as described above, heat resistance of the film can be increased.

Examples of the alicyclic structure-containing polymer may include (1) a norbornene polymer, (2) a monocyclic olefin polymer, (3) a cyclic conjugated diene polymer, (4) a vinyl alicyclic hydrocarbon polymer, and hydrogenated products thereof. Among these, a norbornene polymer is more preferable from the viewpoint of transparency and moldability.

Examples of the norbornene polymer may include a ring-opening polymer of a norbornene monomer, a ring-opening copolymer of a norbornene monomer and another monomer capable of ring-opening copolymerization therewith, and hydrogenated products thereof; an addition polymer of a norbornene monomer, and an addition copolymer of a norbornene monomer and another monomer capable of copolymerization therewith. Among these, from the viewpoint of transparency, a hydrogenated product of a ring-opening polymer of a norbornene monomer is particularly preferable.

The alicyclic structure-containing polymers described above are selected from publicly known polymers disclosed, for example, in Japanese Patent Application Laid-Open No. 2002-321302 A.

The weight-average molecular weight (Mw) of the alicyclic structure-containing polymer is preferably 10,000 to 100,000, more preferably 25,000 to 80,000, and even more preferably 25,000 to 50,000. When the weight-average molecular weight falls within such a range, mechanical strength and moldability of the film are highly balanced and suitable. The weight-average molecular weight may be measured as a polyisoprene-equivalent value (or a polystyrene-equivalent value when the solvent is toluene) by gel permeation chromatography (hereinafter abbreviated as "GPC") using cyclohexane (or toluene when the resin is not dissolved in cyclohexane) as a solvent.

The molecular weight distribution (weight-average molecular weight (Mw)/number-average molecular weight (Mn)) of the alicyclic structure-containing polymer is preferably 1 or more, and more preferably 1.2 or more, and is preferably 10 or less, more preferably 4 or less, and particularly preferably 3.5 or less.

The resin containing the alicyclic structure-containing polymer may be composed only of the alicyclic structure-containing polymer. Alternatively, the resin may contain any blending agent as long as the advantageous effects of the present invention are not significantly impaired. Examples of optional components may include blending agents such as an ultraviolet absorber; an inorganic particulate; a stabilizer such as an antioxidant, a thermal stabilizer, and a near infrared absorber; a resin modifier such as a lubricant, and a plasticizer; a colorant such as a dye and a pigment; and an aging inhibitor. As the optional components, one type thereof may be solely used, and two or more types thereof may also be used in combination at any ratio. The ratio of the alicyclic structure-containing polymer in the resin containing the alicyclic structure-containing polymer is preferably 70% by weight or more, and more preferably 80% by weight or more.

Suitable specific examples of the resin containing an alicyclic structure-containing polymer may be "ZEONOR" manufactured by ZEON Corporation.

The substrate film may be a single layer film including only one layer, or may be a multilayer film including two or more layers. Among these, it is preferable that the substrate film is a multilayer film including a first surface layer, an intermediate layer containing an ultraviolet absorber, and a second surface layer in this order in the thickness direction thereof. That is, it is preferable that the substrate film includes a first surface layer formed of a thermoplastic resin containing a polymer having an alicyclic structure, an intermediate layer formed of a thermoplastic resin containing a polymer having an alicyclic structure and an ultraviolet absorber, and a second surface layer formed of a thermoplastic resin containing a polymer having an alicyclic structure in this order in the thickness direction. With such a multilayer film, the first surface layer and the second surface layer can suppress bleed-out of the ultraviolet absorber contained in the intermediate layer. In the case of using such a multilayer film, when the multilayer phase difference plate of the present invention is incorporated into a polarizing plate and an image display device, it is possible to suppress deterioration of the phase difference plate $P^2$ and the image display device due to ultraviolet rays.

In order to effectively suppress bleed-out, it is preferable that the first surface layer and the second surface layer do not include an ultraviolet absorber. The polymer contained in the first surface layer, the polymer contained in the intermediate layer, and the polymer contained in the second surface layer may be the same as or different from one another. Therefore, the thermoplastic resin contained in the first surface layer and the thermoplastic resin contained in the second surface layer may be different from one another, but are preferably the same because therewith the layers can be easily formed. Usually, the first surface layer and the second surface layer are formed of the same thermoplastic resin as the thermoplastic resin contained in the intermediate layer except that they do not contain an ultraviolet absorber.

Examples of the ultraviolet absorber may include an organic ultraviolet absorber such as a triazine-based ultraviolet absorber, a benzophenone-based ultraviolet absorber, a benzotriazole-based ultraviolet absorber, and an acrylonitrile-based ultraviolet absorber. Among these, a triazine-based ultraviolet absorber is preferable from the viewpoint of excellent ultraviolet absorption performance in the vicinity of a wavelength of 380 nm. The ultraviolet absorber preferably has a molecular weight of 400 or more.

As an example of the triazine-based ultraviolet absorber, a compound having a 1,3,5-triazine ring may preferably be used. Specific examples of the triazine-based ultraviolet absorber may include 2-(4,6-diphenyl-1,3,5-triazine-2-yl)-5-[(hexyl)oxy]-phenol, and 2,4-bis(2-hydroxy-4-butoxyphenyl)-6-(2,4-dibutoxyphenyl)-1,3,5-triazine. Commercially available products of the triazine-based ultraviolet absorber may include, for example, "Tinuvin 1577" (manufactured by Chiba Specialty Chemicals, Inc.).

Examples of the benzotriazole-based ultraviolet absorber may include 2,2'-methylenebis[4-(1,1,3,3-tetramethylbutyl)-6-(2H-benzotriazol-2-yl) phenol], 2-(3,5-di-tert-butyl-2-hydroxyphenyl)-5-chlorobenzotriazole, 2-(2H-benzotriazol-2-yl)-p-crezole, 2-(2H-benzotriazol-2-yl)-4,6-bis (1-methyl-1-phenylethyl) phenol, 2-benzotriazole-2-yl-4,6-di-tert-butylphenol, 2-[5-chloro(2H)-benzotriazol-2-yl]-4-methyl-6-(tert-butyl) phenol, 2-(2H-benzotriazol-2-yl)-4,6-di-tert-butylphenol, 2-(2H-benzotriazol-2-yl)-4-(1,1,3,3-tetramethylbutyl) phenol, 2-(2H-benzotriazol-2-yl)-4-methyl-6-(3,4,5,6-tetrahydrophthalimidylmethyl) phenol, a reaction product of methyl 3-(3-(2H-benzotriazol-2-yl)-5-tert-butyl-4-hydroxyphenyl) propionate/polyethylene glycol 300, and 2-(2H-benzotriazol-2-yl)-6-(linear and side chain dodecyl)-4-methylphenol. Examples of commercially available products of triazole-based ultraviolet absorbers may include "Adeka Stab LA-31" (manufactured by Asahi Denka Kogyo Co., Ltd.).

As the ultraviolet absorbers, one type thereof may be solely used, and two or more types thereof may also be used in combination at any ratio.

In the thermoplastic resin included in the intermediate layer, the amount of the ultraviolet absorber is preferably 1% by weight or more, and more preferably 3% by weight or more, and is preferably 8% by weight or less, and more preferably 6% by weight or less. Herein, when two or more types of ultraviolet absorbers are used, the amount of the ultraviolet absorber refers to the total amount of these ultraviolet absorbers. By setting the amount of the ultraviolet absorber to be equal to or more than the lower limit of the aforementioned range, transmission of ultraviolet rays having a wavelength of 200 nm to 370 nm can be effectively suppressed, and by setting the amount to be equal to or less than the upper limit, the yellow tint of the film can be suppressed, so that deterioration of the color tone can be suppressed. Further, when the amount of the ultraviolet absorber is confined within the aforementioned range, the resin does not contain a large amount of the ultraviolet absorber, and it is thereby possible to suppress deterioration of the heat resistance of the thermoplastic resin.

Examples of the method for producing a thermoplastic resin containing an ultraviolet absorber and a polymer having an alicyclic structure may include a method for blending an ultraviolet absorber into a polymer having an alicyclic structure before production of a substrate film by a melt extrusion method; a method using a master batch containing a high concentration of an ultraviolet absorber; and a method for blending an ultraviolet absorber into a polymer having an alicyclic structure upon producing a substrate film by a melt extrusion method. In these methods, the dispersibility of the ultraviolet absorber can be sufficiently enhanced by setting the amount of the ultraviolet absorber within the aforementioned range.

The method for molding the resin containing an alicyclic structure-containing polymer into the shape of a film is not particularly limited, and a known method such as an extrusion molding method or the like may be adopted. When extrusion molding is performed, a long-length film can be continuously molded, which is preferable from the viewpoint of production efficiency. The method of stretching the film to produce a stretched product is not either particularly limited, and examples of the stretching operation may include stretching in a lengthwise direction of the long-length film, stretching in the width direction, stretching in the oblique direction, and combinations thereof. The thickness of the film, the stretching ratio, and the thickness of the stretched product after the stretching may be appropriately adjusted within respective ranges by which a desired phase difference plate P1 is obtained.

The glass transition temperature of the thermoplastic resin is preferably 80° ° C. or higher, more preferably 100° C. or higher, and still more preferably 120° C. or higher, and is preferably 250° C. or lower, and more preferably 180° ° C. or lower. By setting the glass transition temperature of the thermoplastic resin to be equal to or higher than the lower limit value of the aforementioned range, durability of the substrate film in a high temperature environment can be enhanced, and by setting the glass transition temperature to be equal to or lower than the upper limit value, the stretching treatment can be easily performed.

Further, when the substrate film includes the first surface layer, the intermediate layer, and the second surface layer, it is preferable that the glass transition temperature TgA of the thermoplastic resin contained in the intermediate layer and the glass transition temperature TgB of the thermoplastic resin contained in the first surface layer and the second surface layer satisfy the relationship of TgB−TgA<15° C.

The light transmittance of the substrate film at a wavelength of 380 nm is preferably 10% or less, more preferably 5% or less, and particularly preferably 1% or less. The light transmittance of the substrate film at a wavelength of 280 nm to 370 nm is preferably 1.5% or less, and more preferably 1% or less.

Herein, the light transmittance may be measured by using a spectrophotometer according to JISK0115.

[5. Polarizing Plate and Image Display Device]

The polarizing plate of the present invention includes the multilayer phase difference plate of the present invention described above and a linear polarizer. Further, the image display device of the present invention includes the polarizing plate of the present invention described above. The polarizing plate of the present invention may include, as an optional constituent element, a protective film for protecting the polarizer and an adhesive layer for effecting adhesion thereof. The protective film is usually disposed on both sides of the polarizer directly or via an adhesive layer. However, the polarizing plate may be configured such that the protective film is omitted and the linear polarizer is protected by the multilayer phase difference plate instead of the protective film. The polarizing plate of the present invention, which includes the multilayer phase difference plate in addition to the linear polarizer, can be used as a constituent element of an optical member capable of achieving uniform optical effects in a wide wavelength range.

[5.1. Antireflection Film]

In a preferable example, the polarizing plate of the present invention may be used as an antireflection film in an image display device. Examples of the polarizing plate preferably used as the antireflection film may include the one with a layer configuration of (phase difference plate P2)/(phase difference plate P1)/(linear polarizer), in which the transmission axis of the linear polarizer and the slow axis of the phase difference plate P1 have a relationship of 40° to 50°, preferably 44° to 46°, typically 45°, with respect to each other and the multilayer phase difference plate functions as the ¼ wavelength plate. When such a polarizing plate is disposed in the image display device at a position closer to a viewing side than elements constituting pixels with a surface of the polarizing plate on a linear polarizer side directing toward the viewing side, light, which is made incident from the outside of the device and reflected in the inside of the device, can be prevented from being emitted to the outside of the device and viewed by an observer. Further, when the multilayer phase difference plate of the present invention is included as the phase difference plate, such an antireflection effect can be uniformly obtained in a wide wavelength range.

In such a configuration, optical characteristics of the phase difference plates P1 and P2 may be appropriately adjusted so as to minimize a reflectance Y value of the reflected light in the visible light region. For example, when the visible light region is defined as A=380 nm to 780 nm, the reflectance Y value may be obtained by the following formula (e10).

$$\text{Reflectance } Y \text{ value} = \frac{\int_{380}^{780} S(\lambda) * R(\lambda) * y(\lambda) * d\lambda}{\int_{380}^{780} S(\lambda) * y(\lambda) * d\lambda} \quad (e10)$$

In the formula (e10), $S(\lambda)$ represents a spectral distribution of incident light, $R(\lambda)$ represents a spectral distribution of reflectance, and $y(\lambda)$ represents the y value in the color-matching function. In the antireflection film utilizing the polarizing plate of the present invention, when the phase difference plates P1 and P2 are designed so as to minimize the reflectance Y value, a difference between the in-plane retardation $RePs(\lambda)$ of the multilayer phase difference plate and an ideal distribution can be made very small.

EXAMPLES

Hereinafter, the present invention will be specifically described referring to Examples. However, the present invention is not limited to the Examples described below. The present invention may be optionally modified for implementation without departing from the scope of claims of the present invention and its equivalents. In the following description, "%" and "part" representing quantity are on the basis of weight, unless otherwise specified. The operations described below were performed under the conditions of normal temperature and normal pressure, unless otherwise specified.

(Synthesis Example 1) Synthesis of LC1

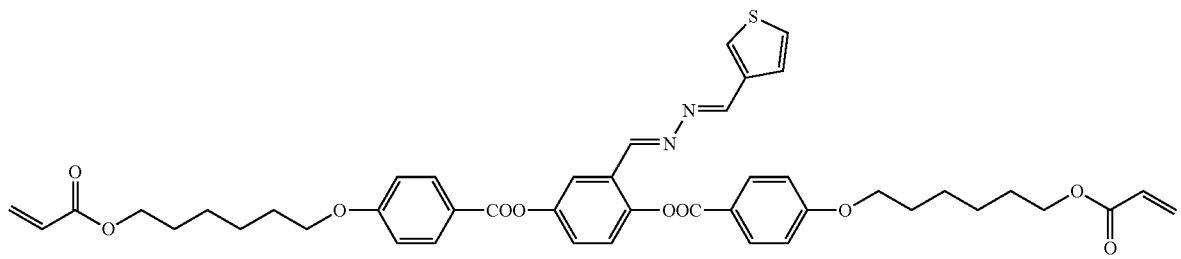

Step 1: Synthesis of Intermediate A

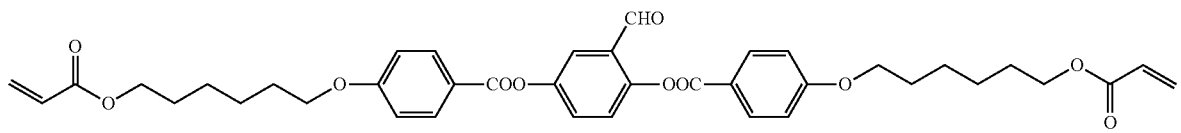

In a four-necked reaction vessel equipped with a thermometer, under a nitrogen flow, 20 g (144.8 mmol) of 2,5-dihydroxybenzaldehyde, 105.8 g (362.0 mmol) of 4-(6-acryloyl-hex-1-yloxy)benzoic acid (manufactured by DKSH Management Ltd.), and 5.3 g (43.4 mmol) of N, N-dimethylaminopyridine were dissolved in 200 ml of N-methylpyrrolidone. To this solution, 83.3 g (434.4 mmol) of 1-ethyl-3-(3-dimethylaminopropyl) carbodiimide hydrochloride (WSC) was added, and the mixture was stirred for 12 hours at the room temperature. After completing the reaction, the reaction liquid was poured into 1.5 liters of water and then extracted with 500 ml of ethyl acetate. The ethyl acetate layer was dried over anhydrous sodium sulfate. After removing sodium sulfate by filtration, ethyl acetate was distilled off under reduced pressure using a rotary evaporator to obtain a pale-yellow solid. The pale-yellow solid was purified by silica gel column chromatography (toluene:ethyl acetate=9:1) to obtain 75 g of an intermediate A represented by the aforementioned formula (A) as a white solid (yield: 75.4%). The structure was identified by $^1$H-NMR. $^1$H-NMR (400 MHZ, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H).

Step 2: Synthesis of Intermediate B

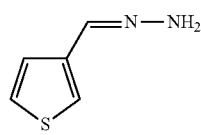

(B)

In a three-necked reaction vessel equipped with a thermometer, under a nitrogen flow, 11.16 g (222.9 mmol) of hydrazine monohydrate and 30 ml of ethanol were added. To this solution, a mixed solution of 5.0 g (44.58 mmol) of 3-thiophenecarboxaldehyde and 10 ml of ethanol was slowly added dropwise at the room temperature. After the dropwise addition was completed, the resulting mixture was stirred for 3 hours at the room temperature. After the reaction was completed, the mixture was washed by adding 300 ml of a saturated aqueous solution of sodium hydrogen carbonate and 800 ml of chloroform. Further, the organic layer was washed twice with 200 ml of the saturated aqueous solution of sodium hydrogen carbonate. Subsequently, the organic layer was collected, dried over anhydrous sodium sulfate, and filtered to remove sodium sulfate. After the solvent was removed by evaporation from the filtrate using the rotary evaporator, a residue thus obtained was dissolved in 30 ml of tetrahydrofuran (THF). To this solution, 300 ml of hexane was added to precipitate a solid, and the precipitated solid was separated by filtration. The solid thus obtained was vacuum-dried to obtain 4.1 g of an intermediate B represented by the aforementioned formula (B) as a pale-yellow solid (yield:73%). $^1$H-NMR (500 MHZ, CDCl$_3$, TMS, δ ppm): 7.82 (s, 1H), 7.39 (dd, 1H, J=1.0 Hz, 5.0 Hz), 7.29-7.31 (m, 2H), 5.41 (br, 2H).

Step 3: Synthesis of LC1

In a three-necked reaction vessel equipped with a thermometer, under a nitrogen flow, 10.2 g (14.86 mmol) of the intermediate A synthesized in the step 1 described above and 80 ml of THE were added. To this solution, 3.75 g (29.72 mmol) of the intermediate B synthesized in the step 2 described above was added. Then, a reaction was performed for 20 hours at the room temperature. After the reaction was completed, extraction was performed by adding 1 litter of the saturated aqueous solution of sodium hydrogen carbonate and 500 ml of ethyl acetate. Further, the organic layer was washed with 300 ml of the saturated aqueous solution of sodium hydrogen carbonate and then further washed with 100 ml of a saturated aqueous solution of sodium chloride. The organic layer was collected, dried over anhydrous sodium sulfate, and filtered to remove sodium sulfate. The solvent was removed by evaporation from the filtrate using the rotary evaporator to obtain a yellow oil. The yellow oil was purified by silica gel column chromatography (toluene: ethyl acetate=95:5) to obtain 5.8 g of a compound LC1 represented by the aforementioned formula LC1 as a pale-yellow oil (yield: 49.1%). The structure of the intended product was identified by $^1$H-NMR.

$^1$H-NMR (500 MHz, CDCl$_3$, TMS, δ ppm): 8.75 (s, 1H), 8.56 (s, 1H), 8.15-8.20 (m, 4H), 8.04 (d, 1H, J=3.0 Hz), 7.70 (dd, 1H, J=1.0 Hz, 3.0 Hz), 7.55 (dd, 1H, J=1.0 Hz, 5.0 Hz), 7.30-7.39 (m, 3H), 6.98-7.01 (m, 4H), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.192 (t, 2H, J=6.5 Hz), 4.191 (t, 2H, J=6.5 Hz), 4.08 (t, 2H, J=6.0 Hz), 4.07 (t, 2H, J=6.5 Hz), 1.83-1.89 (m, 4H), 1.71-1.77 (m, 4H), 1.45-1.57 (m, 8H).

(Synthesis Example 2) Synthesis of LC2

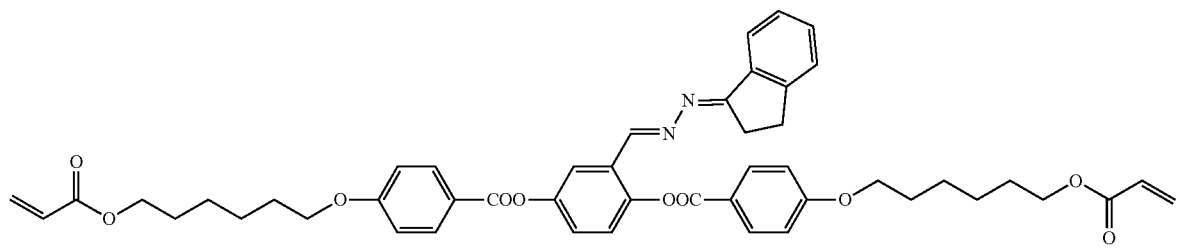

LC2

Step 1: Synthesis of Intermediate C

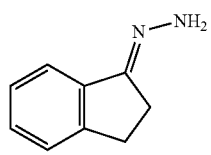
(C)

In a three-necked reaction vessel equipped with a thermometer, under a nitrogen flow, 5.68 g (113.5 mmol) of hydrazine monohydrate and 30 ml of ethanol were added. To this solution, 3.0 g (22.7 mmol) of 1-indanone was added, and the resulting mixture was heated at 60° C. for 6 hours. After the reaction was completed, extraction was performed by adding 300 ml of the saturated aqueous solution of sodium hydrogen carbonate and 600 ml of chloroform to the reaction liquid. Further, the organic layer was washed twice with 200 ml of the saturated aqueous solution of sodium hydrogen carbonate. Subsequently, the organic layer was collected, dried over anhydrous sodium sulfate, and filtered to remove sodium sulfate. After the solvent was removed by evaporation from the filtrate using the rotary evaporator, a residue thus obtained was dissolved in 30 ml of tetrahydrofuran (THF). To this solution, 300 ml of hexane was added to precipitate a solid, and the precipitated solid was separated by filtration. The solid thus obtained was vacuum-dried to obtain 2.46 g of an intermediate C represented by the aforementioned formula (C) as a pale-yellow solid (yield: 74%). $^1$H-NMR (500 MHZ, CDCl$_3$, TMS, δ ppm): 7.64 (d, 1H, J=7.5 Hz), 7.23-7.31 (m, 3H), 5.15 (br, 2H), 3.11-3.13 (m, 2H), 2.67-2.70 (m, 2H).

Step 2: Synthesis of LC2

In a three-necked reaction vessel equipped with a thermometer, under a nitrogen flow, 5.2 g (7.57 mmol) of the intermediate A synthesized in the step 1 in Synthesis Example 1 described above, 50 ml of THE, and 10 ml of ethanol were added. To this solution, 2.43 g (16.65 mmol) of the intermediate C synthesized in the step 1 described above was added. Subsequently, a reaction was performed at 60° C. for 3 hours. After the reaction was completed, extraction was performed by adding 1 litter of the saturated aqueous solution of sodium hydrogen carbonate and 300 ml of ethyl acetate. Further, the organic layer was washed with 300 ml of the saturated aqueous solution of sodium hydrogen carbonate and then further washed with 100 ml of the saturated aqueous solution of sodium chloride. The organic layer was collected, dried over anhydrous sodium sulfate, and filtered to remove sodium sulfate. The solvent was removed by evaporation from the filtrate using the rotary evaporator to obtain a yellow oil. The yellow oil was purified by silica gel column chromatography (toluene:ethyl acetate=90:10) to obtain 2.8 g of a compound LC2 represented by the aforementioned formula LC2 as a pale-yellow solid (yield: 45.4%). The structure of the intended product was identified by $^1$H-NMR. $^1$H-NMR (500 MHz, CDCl$_3$, TMS, δ ppm): 8.65 (s, 1H), 8.17-8.19 (m, 4H), 8.04 (d, 1H, J=3.0 Hz), 7.84 (d, 1H, J=8.0 Hz), 7.41 (td, 1H, J=1.0 Hz, 7.5 Hz), 7.34-7.36 (m, 2H), 7.25-7.31 (m, 2H), 6.99 (dd, 4H, J=1.0 Hz, 8.5 Hz), 6.41 (dd, 2H, J=1.0 Hz, 17.5 Hz), 6.13 (dd, 2H, J=10.5 Hz, 17.5 Hz), 5.832 (dd, 1H, J=1.0 Hz, 10.5 Hz), 5.831 (dd, 1H, J=1.0 Hz, 10.5 Hz), 4.19 (t, 4H, J=6.5 Hz), 4.069 (t, 2H, J=6.5 Hz), 4.067 (t, 2H, J=6.5 Hz), 3.06 (br, 4H), 1.86 (tt, 4H, J=6.5 Hz, 6.5 Hz), 1.74 (tt, 4H, J=7.0 Hz, 7.0 Hz), 1.45-1.60 (m, 8H).

(Synthesis Example 3) Synthesis of LC3

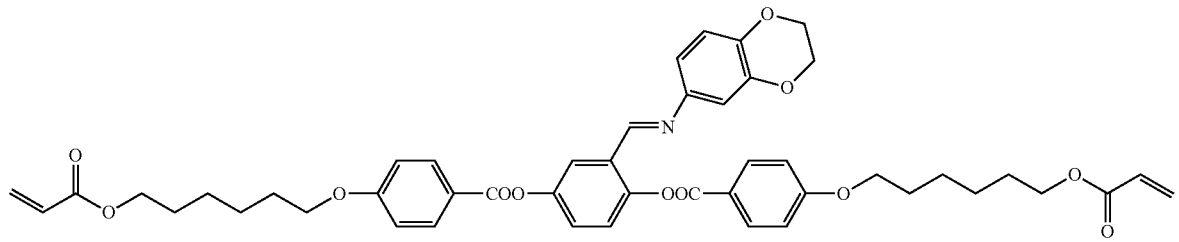
LC3

Step 1: Synthesis of Intermediate D

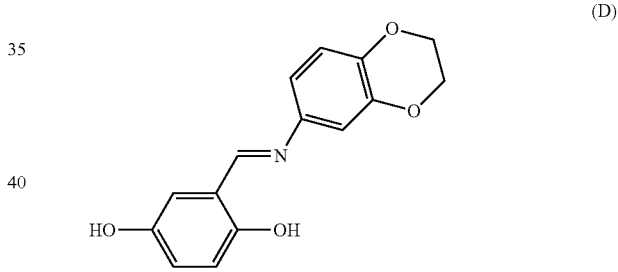
(D)

In a three-necked reaction vessel equipped with a thermometer, under a nitrogen flow, 10 g (72.4 mmol) of 2,5-dihydroxybenzaldehyde and 150 ml of ethanol were added. To this, 10.94 g (72.4 mmol) of 6-amino-1,4-benzodioxane was added, and the resulting mixture was stirred for 2 hours at the room temperature. After the reaction was completed, a precipitated solid was filtrated and washed with cold ethanol. The solid thus obtained was vacuum-dried to obtain 13.5 g of an intermediate D represented by the aforementioned formula (D) as a pale-yellow solid (yield: 68.7%). The structure of the intended product was identified by $^1$H-NMR. $^1$H-NMR (400 MHZ, DMSO-d6, TMS, δ ppm): 12.28 (s, 1H), 9.02 (s, 1H), 8.76 (s, 1H), 6.96-6.98 (1H, m), 6.95 (d, 1H, J=2.8 Hz), 6.86-6.90 (2H, m), 6.80 (dd, 1H, J=2.8 Hz, 8.8 Hz), 6.73 (d, 1H, J=8.8 Hz), 4.23 (s, 4H).

Step 2: Synthesis of LC3

In a four-necked reaction vessel equipped with a thermometer, under a nitrogen flow, 5.0 g (18.4 mmol) of the intermediate D synthesized in the step 1 described above and 13.47 g (46.1 mmol) of 4-(6-acryloyl-hex-1-yloxy)benzoic acid (manufactured by DKSH Management Ltd.) were dissolved in 100 ml of N-methylpyrrolidone. To this solution, 10.58 g (55.2 mmol) of 1-ethyl-3-(3-dimethylaminopropyl) carbodiimide hydrochloride (WSC) and 1.12 g (9.2 mmol) of N, N-dimethylaminopyridine were added, and the resulting mixture was stirred for 12 hours at the room temperature. After completing the reaction, the reaction liquid was mixed with 1 liter of water and then extracted with 500 ml of ethyl acetate. The ethyl acetate layer was washed with 200 ml of the saturated aqueous solution of sodium chloride. The organic layer was collected and dried over anhydrous sodium sulfate. After sodium sulfate was removed by filtration, ethyl acetate was distilled off under reduced pressure using the rotary evaporator to obtain a pale-yellow solid. The pale-yellow solid was purified by column chromatography (toluene:ethyl acetate=9:1) having alumina as a filler to obtain 3.8 of a compound LC3 represented by the aforementioned formula LC3 as a pale-yellow solid (yield: 25.2%). The structure was identified by $^1$H-NMR. $^1$H-NMR (500 MHZ, CDCl$_3$, TMS, δ ppm): 8.56 (s, 1H), 8.17 (d, 2H, J=9.0 Hz), 8.15 (d, 2H, J=9.0 Hz), 8.07 (d, 1H, J=3.0 Hz), 7.37 (dd, 1H, J=3.0 Hz, 8.5 Hz), 7.30 (d, 1H, J=8.5 Hz), 6.99 (d, 2H, J=7.5 Hz), 6.97 (d, 2H, J=7.5 Hz), 6.81 (d, 1H, J=8.5 Hz), 6.72 (d, 1H, J=2.5 Hz), 6.69 (dd, 1H, J=2.5 Hz, 8.5 Hz), 6.40 (dd, 2H, J=1.5 Hz, 17.5 Hz), 6.13 (2H, dd, J=10.5 Hz, 17.5 Hz), 5.82 (dd, 2H, J=1.5 Hz, 10.5 Hz), 4.22 (s, 4H), 4.18 (t, 4H, J=6.5 Hz), 4.05 (t, 4H, J=6.5 Hz), 1.80-1.87 (m, 4H), 1.69-1.76 (m, 4H), 1.44-1.57 (m, 8H).

<Measurement of Phase Transition Temperature>

Small amounts of the compounds LC1 to 3 in the solid state were placed between two glass substrates with a polyimide orientation film that had been subjected to a rubbing treatment (product name: orientation-treated glass substrate, manufactured by E. H. C. Co., Ltd.). The substrates were placed on a hot plate, and the temperature was increased from 40° C. to 100° C. and then decreased to 40° C. again. A change in a constitutional structure during the increase and decrease of the temperature was observed with a polarizing optical microscope (ECLIPSE LV100POL model, manufactured by Nikon Corp.).

The measured phase transition temperatures are shown in Table 1 below.

In Table 1, "C", "N", and "I" refer to "Crystal", "Nematic", and "Isotropic", respectively. The term "Crystal" herein means that a test compound is in a solid phase, the term "Nematic" means that a test compound is in a nematic liquid crystal phase, and the term "Isotropic" means that a test compound is in an isotropic liquid phase.

TABLE 1

| Compound number | Phase transition temperature |
|---|---|
| LC1 | C ⇌ (40° C. or less) N ⇌ (54° C.) I ; 77° C. |
| LC2 | C ⇌ (40° C. or less) N ⇌ (60° C.) I ; 89° C. |
| LC3 | C ⇌ (40° C. or less) N ⇌ (47° C.) I ; 74° C. |

Example 1

(1-1. Preparation of Liquid Crystal Composition)

Materials (1a) to (1e) described below were weighed and placed in a light-shielding bottle to prepare a mixture.

(1a) Liquid crystal compound: compound LC1 synthesized in Synthesis Example 1 (number of ∥ electrons 10) 21.0 parts by weight.

(1b) Surfactant:1 wt % cyclopentanone solution of "MEGAFACE F-562" (product name, manufactured by DIC Corporation) 6.3 parts by weight.

(1c) Polymerization initiator: "N1919" (product name, manufactured by Adeka Corp.) 0.9 part by weight.

(1d) Solvent:1,3-dioxolane 46.8 parts by weight.

(1e) Solvent: cyclopentanone 25.0 parts by weight.

LC1

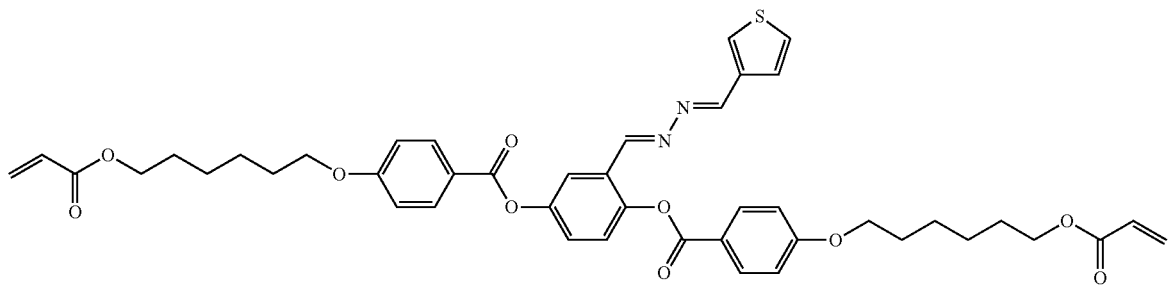

The mixture was stirred in a light-shielding bottle at 60° C. for 1.0 hour. After completion of the stirring, the mixture was allowed to stand at the room temperature to be cooled down. The mixture cooled down to the room temperature was passed through a membrane filter of 0.45 µm. In this manner, the liquid crystal composition was prepared.

(1-2. Preparation of Support Body)

As a support body, "ZEONOR film" manufactured by ZEON Corporation was prepared. This support body was a long-length film having a thickness of 47 µm. The glass transition temperature (Tg) of the resin constituting the film was 126° C. This support body had a phase difference, and the in-plane retardation Re of the support body at a wavelength of 550 nm was 141 nm and the in-plane slow axis direction of the support body was inclined at an angle of 45° with respect to the width direction of the support body.

(1-3. Phase Difference Plate P2)

The liquid crystal composition obtained in (1-1) was applied onto one surface of the support body obtained in (1-2). The application was performed by a bar coating using a wire bar of count No. 03. After the application, the support body was placed in an oven at 65° C. to perform a heating treatment for 2 minutes. After drying, the support body was allowed to stand at the room temperature for 1 hour. In this manner, the liquid crystal compound in the layer of the liquid crystal composition was oriented.

Subsequently, the layer of the liquid crystal composition was irradiated with ultraviolet rays. The irradiation of ultraviolet rays was performed at an exposure of 150 mJ/cm$^2$ or more using H-Bulb (manufactured by Heraeus Noblelight GmbH). In this manner, the layer of the liquid crystal composition was cured to produce the phase difference plate P2, and a multilayer product (i) having a layer configuration of (support body)/(phase difference plate P2) was obtained. The phase difference plate P2 thus obtained had a film thickness of 1.67 μm.

A surface of the multilayer product thus obtained on a side of the phase difference plate P2 was bonded to a glass substrate via an adhesive, and the support body was peeled off. In this manner, a multilayer product (ii) of (glass substrate)/(adhesive layer)/(phase difference plate P2) was obtained.

(1-4. Wavelength Distribution Measurement of Phase Difference Plate P2)

The in-plane retardation Re of the phase difference plate P2 on the multilayer product (ii) obtained in (1-3) was measured. The measurement was performed at intervals of 5 nm in a range of wavelength λ=380 nm to 780 nm. A phase difference meter (manufactured by Axometrics, Inc.) was used for the measurement. The measurement results thus obtained showed the wavelength distribution which generally followed the Cauchy distribution formula, although there were some fluctuations in the measurement values possibly due to interference of the film.

(1-5. Calculation of Cauchy Fitting, Linear Index, and Re(400)/Re(700))

From the measurement results in (1-4), values of Re(450)/Re(550), Re(550)/Re(550), and Re(650)/Re(550) were obtained, and these values were subjected to the Cauchy fitting. That is, values of constants A, B, and C minimizing X calculated by the following formula were obtained.

$$X=\{Re(450)/Re(550)-Re(450)c/Re(550)c\}^2+\{Re(550)/Re(550)-Re(550)c/Re(550)c\}^2+\{Re(650)/Re(550)-Re(650)c/Re(550)c\}^2$$

In the formula described above, Re(450)/Re(550), Re(550)/Re(550), and Re(650)/Re(550) are the actual measurement values described above, and Re(450) c/Re(550) c, Re(550) c/Re(550) c, and Re(650)/Re(550) c are values obtained from calculated values of Re(λ) c/Re(550)c=A+ $(B/\lambda^2)+(C/\lambda^4)$.

The relationship between the wavelength λ and Re(λ)/Re(550) was calculated at intervals of 10 nm in a range of 380 nm to 780 nm on the basis of the values of the constants A, B, and C obtained as the result of the Cauchy fitting. The result is shown in Table 2. In the following calculations in present Example, values corrected by the Cauchy fitting were used as the in-plane retardation ReP2(λ) of the phase difference plate P2 at each wavelength λ.

Further, the linear index and the value of Re(400)/Re(700) of the phase difference plate P2 were calculated from the values of ReP2(400)/ReP2(550), ReP2(550)/ReP2(550), and ReP2(700)/ReP2(550) obtained as the result of the Cauchy fitting. The result is shown in Table 3.

(1-6. Phase Difference Plate P1)

100 parts of a dried thermoplastic resin (COP1) containing an alicyclic structure-containing polymer (manufactured by ZEON Corporation, glass transition temperature of 123° C.) and 5.5 parts of a benzotriazole-based ultraviolet absorber ("LA-31" manufactured by Adeka Corp.) were mixed by a biaxial extruder. Subsequently, the mixture was fed to a hopper connected to an extruder, supplied to a uniaxial extruder, and melt-extruded to obtain a thermoplastic resin (J1) containing the ultraviolet absorber. The amount of the ultraviolet absorber in the thermoplastic resin (J1) was 5.2% by weight.

A uniaxial extruder that was equipped with a leaf disc-shaped polymer filter having an opening of 3 μm and had a double flight screw with a diameter of 50 mm (a ratio of screw effective length L relative to screw diameter D, L/D=32) was prepared. The thermoplastic resin (J1) described above was fed to a hopper mounted on the uniaxial extruder. Then, the thermoplastic resin (J1) was melted, and the melted thermoplastic resin (J1) was supplied to a multi-manifold die at an outlet temperature of the extruder of 280° C. and a rotation speed of a gear pump of the extruder of 10 rpm. The die lip of the multi-manifold die had an arithmetic surface roughness R$^a$ of 0.1 μm.

On the other hand, apart from the uniaxial extruder to which the thermoplastic resin (J1) was fed, another uniaxial extruder that was equipped with a leaf disc-shaped polymer filter having an opening of 3 μm and had a screw with a diameter of 50 mm (L/D=32) was prepared. The thermoplastic resin (COP1) containing the same alicyclic structure-containing polymer as that used in the production of the thermoplastic resin (J1) was fed to a hopper mounted on the uniaxial extruder. Then, the thermoplastic resin (COP1) was melted, and the melted thermoplastic resin (COP1) was supplied to the multi-manifold die described above at the outlet temperature of the extruder of 285° C. and the rotation speed of the gear pump of the extruder of 4 rpm.

The melted thermoplastic resin (COP1), the melted thermoplastic resin (J1) containing the ultraviolet absorber, and the melted thermoplastic resin (COP1) were each discharged from the multi-manifold die at 280° C. and casted on a cooling roll whose temperature was adjusted to 150° C. to obtain a pre-stretch film. Upon discharging the resins, the air gap amount was set to 50 mm. Further, as a method for casting the discharged resins on the cooling roll, edge pinning was adopted.

The pre-stretch film thus obtained was a multilayer film of three-layered structure including a resin layer formed of the thermoplastic resin (COP1) with a thickness of 15 μm, a resin layer formed of the thermoplastic resin (J1) containing the ultraviolet absorber with a thickness of 40 μm, and a resin layer formed of the thermoplastic resin (COP1) with a thickness of 15 μm in this order. Further, the pre-stretch film had a width of 1,400 mm and a total thickness of 70 μm. The pre-stretch film thus obtained was subjected to a trimming treatment in which both end portions of the pre-stretch film in the width direction were trimmed by 50 mm to trim the width thereof to 1,300 mm.

The pre-stretch film described above was stretched in a diagonal direction that was not parallel or perpendicular to the lengthwise direction of the pre-stretch film under conditions of a stretching temperature of 140° C. and a stretching rate of 20 m/min to obtain a stretched film as a substrate film. The stretched film thus obtained was a multilayer film of three-layered structure including a first surface layer formed of the thermoplastic resin (COP1) with a thickness of 8 µm, an intermediate layer formed of the thermoplastic resin (J1) containing the ultraviolet absorber with a thickness of 31 µm, and a second surface layer formed of the thermoplastic resin (COP1) with a thickness of 8 µm in this order. Further, the stretched film had a width of 1,330 mm, a thickness of 47 µm, and a slow axis inclined at an angle of 45° with respect to the lengthwise direction of the stretched film.

The stretched film had an in-plane retardation at a measurement wavelength 550 nm of 100 nm, a light transmittance at a measurement wavelength 380 nm of 0.02%, and a refractive index of 1.53.

On the assumption that the stretched film described above was used as the phase difference plate P1, the in-plane retardation ReP1($\lambda$) of this film at each wavelength $\lambda$ was measured and subjected to the Cauchy fitting to calculate a relationship between the wavelength $\lambda$ and ReP1($\lambda$)/ReP1 (550). The specific method thereof was the same as that performed in (1-4) for the phase difference plate P2. The result is shown in Table 2. In the following calculation, this value was used as the in-plane retardation ReP1($\lambda$) of the phase difference plate P1 at each wavelength A.

(1-7. Simulation)

On the assumption that a multilayer phase difference plate was constituted by using the phase difference plate P1 in (1-6) and the phase difference plate P2 in (1-4) and an antireflection film was constituted by combining this multilayer phase difference plate with a linear polarizer, performance of the antireflection film was simulated. Simulation details are as follows.

The antireflection film was disposed on a reflection plate causing ideal mirror reflection, and the reflectance Y value obtained when light incident on the antireflection film was discharged from the antireflection film was calculated. The layer configuration of the antireflection film was (phase difference plate P2)/(phase difference plate P1)/(linear polarizer) in the order from the side closer to the reflection plate. The slow axis of the phase difference plate P2 was set to the direction orthogonal to the direction of the slow axis of the phase difference plate P1. Further, the slow axis of the phase difference plate P1 was inclined at an angle of 45° with respect to the absorption axis of the linear polarizer.

In the aforementioned configuration, the combination of the phase difference plate P2 and the phase difference plate P1 is assumed to be equivalent to a single phase difference plate Ps. In a case where the slow axis direction of the phase difference plate Ps is set to the same direction as that of the phase difference plate P1, the in-plane retardation RePs($\lambda$) of the phase difference plate Ps, the in-plane retardation ReP2($\lambda$) of the phase difference plate P2, and the in-plane retardation ReP1($\lambda$) of the phase difference plate P1 at the wavelength $\lambda$ have a relationship of RePs($\lambda$)=ReP1($\lambda$)–ReP2($\lambda$).

In the aforementioned configuration, a ratio R (A) of the reflected light with respect to the incident light at the wavelength $\lambda$ is as presented by the following formula (e11) assuming that the polarizing plate has an ideal polarization effect.

$$R(\lambda) = S(\lambda)\left(\cos\left(\frac{\pi \times 2 RePs(\lambda)}{\lambda}\right)\right)^2 \qquad (e11)$$

In the formula (e11), S($\lambda$) represents a spectral distribution of the incident light and was set to 1 at all wavelengths in the present simulation.

It was premised that the thickness of the phase difference plates P1 and P2 were set such that the phase difference plate Ps functions as an ideal ¼ wavelength plate at the center of the visible wavelength of 550 nm. That is, it was premised that RePs(550)=137.5 nm. Under this premise, studies were conducted as to cases wherein the thicknesses of the phase difference plate P1 and the phase difference plate P2 take a variety of values. That is, a variety of combinations of ReP1($\lambda$) and ReP2($\lambda$) satisfying the relationship of ReP1 (550)–ReP2(550)=137.5 nm were set and, of these, the combination minimizing the reflectance Y value of the reflected light was determined.

The reflectance Y value was approximately calculated by the following formula (e12).

$$\text{Reflectance } Y \text{ value} = \frac{\sum_{n=38}^{78} y(10n) \times \left(\cos\left(\frac{\pi \times 2 RePs(10n)}{10n}\right)\right)^2}{\sum_{n=38}^{78} y(10n)} \qquad (e12)$$

In the formula (e12), 10n are values of $\lambda$ at intervals of 10 nm (i.e., n=$\lambda$/10). The value of RePs($\lambda$) at each wavelength was obtained from values of Rep1($\lambda$)/ReP1(550) and ReP2 ($\lambda$)/ReP2(550) shown in Table 2 and values of ReP1(550) and ReP2(550) in the combinations thus set. The function y($\lambda$) is a function of the wavelength $\lambda$ and the y value of the color matching function, and the values shown in Table 2 were adopted. The minimum value of the reflectance Y value and values of ReP1(550) and ReP2(550) that give the minimum value of the reflectance Y value (ReP1(550) min and ReP2(550)) obtained as the result of the aforementioned calculation are shown in Table 3.

Further, in the case of the aforementioned conditions where the reflectance Y value showed the minimum value, a displacement index, as an index of displacement in wavelength distribution observed between the wavelength distribution of the phase difference plate Ps and the ideal wavelength distribution shown by a virtual phase difference plate Pi, was calculated on the basis of the following formula (e13). The results are shown in Table 3.

$$\text{Displacement index} = \sum_{n=38}^{78} \left(\frac{RePs(10n)}{RePs(550)} - \frac{RePi(10n)}{RePi(550)}\right)^2 \qquad (e13)$$

In the formula (e13), RePi($\lambda$) is a function showing the ideal distribution and satisfies (RePi($\lambda$)/RePi(550))=$\lambda$/550.

Example 2

(2-1. Wavelength Distribution Measurement of Phase Difference Plate P2)

A phase difference plate P2 was obtained and an in-plane retardation Re thereof was measured by the same operation as that of (1-1) to (1-4) of Example 1 except that the compound LC2 (the number of π electrons was 12) synthesized in Synthesis Example 2 was used instead of the compound LC1 synthesized in Synthesis Example 1 as the liquid crystal compound of (1a).

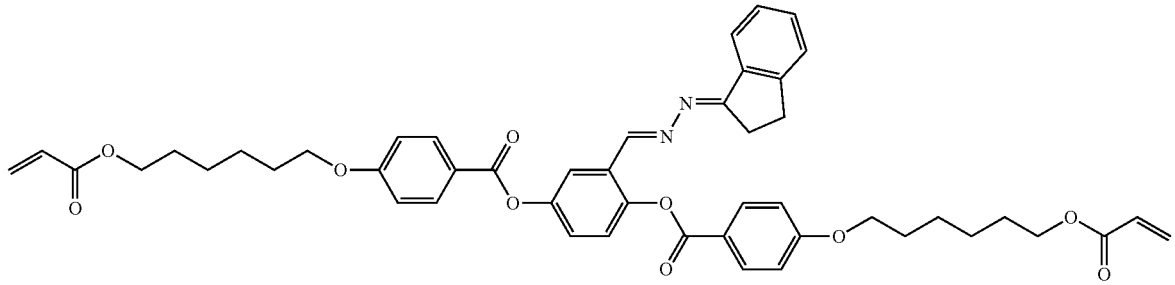

LC2

(2-2. Evaluation)

The simulation and the like were performed by the same operation as that of (1-5) to (1-7) of Example 1 except that the measurement result in (2-1) was used instead of the measurement result in (1-4).

The results are shown in Table 2 and 3.

Example 3

(3-1. Wavelength Distribution Measurement of Phase Difference Plate P2)

A phase difference plate P2 was obtained and an in-plane retardation Re thereof was measured by the same operation as that of (1-1) to (1-4) of Example 1 except that the compound LC3 (the number of π electrons was 12) synthesized in Synthesis Example 3 was used instead of the compound LC1 synthesized in Synthesis Example 1 as the liquid crystal compound of (1a).

values of Re(450)/Re(550), Re(550)/Re(550), and Re(650)/Re(550) were set to 1.18, 1.00, and 0.93, respectively. The results are shown in Table 2 and Table 3.

Comparative Example 2

According to Example 1 in Japanese Patent Application Laid-Open No. 2014-206684 A, a ¼ wavelength plate satisfying Re(450)/Re(550)=1.10 and Re(650)/Re(550)=0.95 was obtained. The Cauchy fitting and simulation were performed in a case where this ¼ wavelength plate was adopted as the phase difference plate P2. That is, the simulation and the like were performed by the same operation as that of (1-5) to (1-7) of Example 1 except that

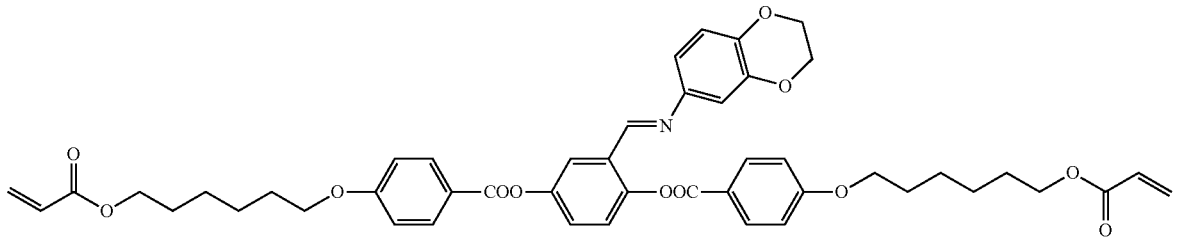

LC3

(3-2. Evaluation)

The simulation and the like were performed by the same operation as that of (1-5) to (1-7) of Example 1 except that the measurement result in (3-1) was used instead of the measurement result in (1-4).

The results are shown in Table 2 and 3.

Comparative Example 1

According to Examples 4 and 6 in Japanese Patent Application Laid-Open No. 2014-206684 A, a ¼ wavelength plate satisfying Re(450)/Re(550)=1.18 and Re(650)/Re(550)=0.93 was obtained. The Cauchy fitting and simulation were performed in a case where this ¼ wavelength plate was adopted as the phase difference plate P2. That is, the simulation and the like were performed by the same operation as that of (1-5) to (1-7) of Example 1 except that values of Re(450)/Re(550), Re(550)/Re(550), and Re(650)/Re(550) were set to 1.10, 1.00, and 0.95, respectively. The results are shown in Table 2 and Table 3.

Comparative Example 3

(C3-1. Wavelength Distribution Measurement of Phase Difference Plate P2)

A phase difference plate P2 was obtained and an in-plane retardation Re thereof was measured by the same operation as that of (1-1) to (1-4) of Example 1 except that the liquid crystal compound represented by the following formula LC4 was used instead of the compound LC1 synthesized in Synthesis Example 1 as the liquid crystal compound of (1a).

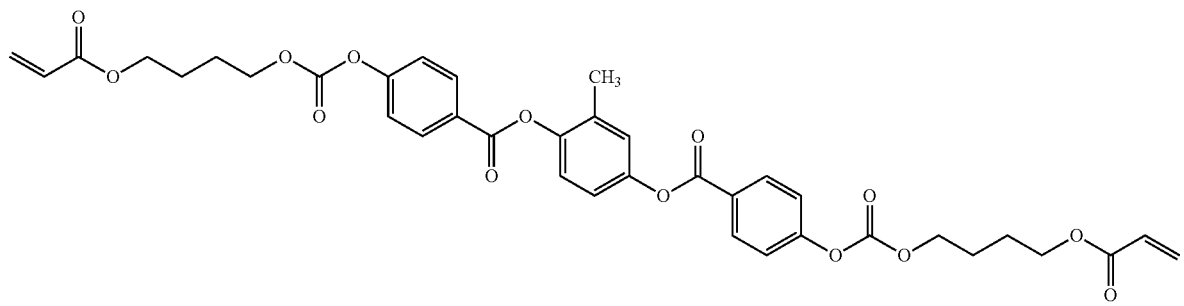

LC4

(C3-2. Evaluation)
The simulation was performed by the same operation as that of (1-5) to (1-7) of Example 1 except that the measurement result in (C3-1) was used instead of the measurement result in (1-4). The results are shown in Table 2 and 3.

Comparative Example 4

(C4-1. Wavelength Distribution Measurement of Phase Difference Plate P2)
A phase difference plate P2 was obtained and an in-plane retardation Re thereof was measured by the same operation as that of (1-1) to (1-4) of Example 1 except that the liquid crystal compound represented by the following formula LC5 was used instead of the compound LC1 synthesized in Synthesis Example 1 as the liquid crystal compound of (1a) and the temperature of the oven was set to 100° C.

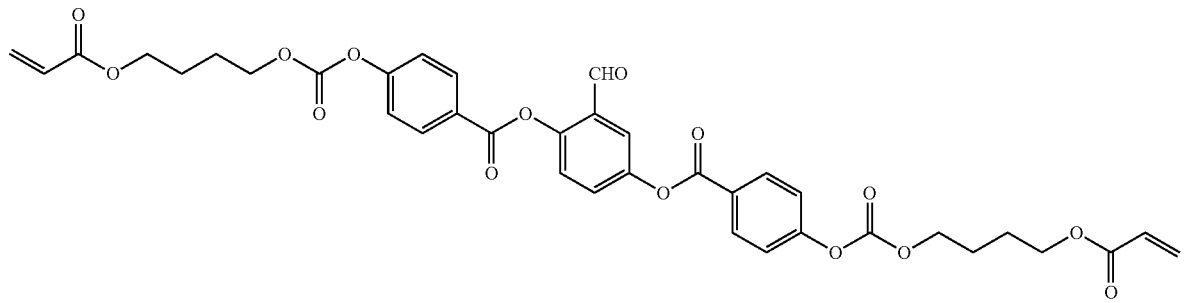

LC5

(C4-2. Evaluation)
The simulation and the like were performed by the same operation as that of (1-5) to (1-7) of Example 1 except that the measurement result in (C4-1) was used instead of the measurement result in (1-4). The results are shown in Table 2 and 3.

TABLE 2

|  | ReP2 ($\lambda$)/ Re (550) | | | | | | | RreP1 | color- |
| --- | --- | --- | --- | --- | --- | --- | --- | --- | --- |
| $\lambda$ (nm) | Ex. 1 | Ex. 2 | Ex. 3 | Comp. Ex. 1 | Comp. Ex. 2 | Comp. Ex. 3 | Comp. Ex. 4 | ($\lambda$)/ (Re550) | matching function |
| 380 | 1.567 | 1.505 | 1.139 | 1.493 | 1.244 | 1.283 | 1.107 | 1.050 | 0.000 |
| 390 | 1.523 | 1.470 | 1.127 | 1.430 | 1.217 | 1.250 | 1.097 | 1.045 | 0.000 |
| 400 | 1.480 | 1.434 | 1.116 | 1.375 | 1.192 | 1.220 | 1.088 | 1.040 | 0.000 |
| 410 | 1.439 | 1.399 | 1.106 | 1.326 | 1.170 | 1.193 | 1.080 | 1.036 | 0.001 |
| 420 | 1.399 | 1.365 | 1.096 | 1.282 | 1.150 | 1.169 | 1.071 | 1.032 | 0.004 |
| 430 | 1.360 | 1.331 | 1.086 | 1.244 | 1.132 | 1.147 | 1.064 | 1.028 | 0.012 |
| 440 | 1.323 | 1.298 | 1.077 | 1.210 | 1.115 | 1.128 | 1.057 | 1.025 | 0.023 |
| 450 | 1.287 | 1.266 | 1.068 | 1.179 | 1.100 | 1.110 | 1.050 | 1.022 | 0.038 |

TABLE 2-continued

| | ReP2 (λ)/ Re (550) | | | | | | | ReP1 | color- |
| λ (nm) | Ex. 1 | Ex. 2 | Ex. 3 | Comp. Ex. 1 | Comp. Ex. 2 | Comp. Ex. 3 | Comp. Ex. 4 | (λ)/ (Re550) | matching function |
|---|---|---|---|---|---|---|---|---|---|
| 460 | 1.252 | 1.235 | 1.060 | 1.152 | 1.086 | 1.094 | 1.044 | 1.019 | 0.060 |
| 470 | 1.219 | 1.205 | 1.052 | 1.127 | 1.073 | 1.080 | 1.038 | 1.016 | 0.091 |
| 480 | 1.188 | 1.176 | 1.044 | 1.105 | 1.061 | 1.066 | 1.032 | 1.014 | 0.139 |
| 490 | 1.157 | 1.148 | 1.037 | 1.085 | 1.051 | 1.054 | 1.027 | 1.011 | 0.208 |
| 500 | 1.128 | 1.121 | 1.030 | 1.068 | 1.040 | 1.043 | 1.022 | 1.009 | 0.323 |
| 510 | 1.100 | 1.095 | 1.023 | 1.051 | 1.031 | 1.033 | 1.017 | 1.007 | 0.503 |
| 520 | 1.074 | 1.070 | 1.017 | 1.037 | 1.023 | 1.024 | 1.012 | 1.005 | 0.710 |
| 530 | 1.048 | 1.045 | 1.011 | 1.023 | 1.014 | 1.015 | 1.008 | 1.003 | 0.862 |
| 540 | 1.023 | 1.022 | 1.005 | 1.011 | 1.007 | 1.007 | 1.004 | 1.002 | 0.954 |
| 550 | 1.000 | 1.000 | 1.000 | 1.000 | 1.000 | 1.000 | 1.000 | 1.000 | 0.995 |
| 560 | 0.977 | 0.979 | 0.995 | 0.990 | 0.993 | 0.993 | 0.996 | 0.999 | 0.995 |
| 570 | 0.956 | 0.958 | 0.990 | 0.981 | 0.987 | 0.987 | 0.993 | 0.997 | 0.952 |
| 580 | 0.935 | 0.938 | 0.985 | 0.972 | 0.982 | 0.981 | 0.989 | 0.996 | 0.870 |
| 590 | 0.915 | 0.919 | 0.980 | 0.964 | 0.976 | 0.976 | 0.986 | 0.995 | 0.757 |
| 600 | 0.896 | 0.901 | 0.976 | 0.957 | 0.971 | 0.971 | 0.983 | 0.993 | 0.631 |
| 610 | 0.878 | 0.883 | 0.972 | 0.951 | 0.966 | 0.966 | 0.980 | 0.992 | 0.503 |
| 620 | 0.861 | 0.866 | 0.968 | 0.945 | 0.962 | 0.962 | 0.978 | 0.991 | 0.381 |
| 630 | 0.844 | 0.850 | 0.964 | 0.939 | 0.958 | 0.957 | 0.975 | 0.990 | 0.265 |
| 640 | 0.828 | 0.834 | 0.960 | 0.934 | 0.954 | 0.954 | 0.972 | 0.989 | 0.175 |
| 650 | 0.812 | 0.819 | 0.957 | 0.929 | 0.950 | 0.950 | 0.970 | 0.988 | 0.107 |
| 660 | 0.797 | 0.804 | 0.953 | 0.925 | 0.946 | 0.947 | 0.968 | 0.988 | 0.061 |
| 670 | 0.783 | 0.790 | 0.950 | 0.921 | 0.943 | 0.943 | 0.965 | 0.987 | 0.032 |
| 680 | 0.769 | 0.777 | 0.947 | 0.917 | 0.940 | 0.940 | 0.963 | 0.986 | 0.017 |
| 690 | 0.756 | 0.764 | 0.944 | 0.913 | 0.937 | 0.938 | 0.961 | 0.985 | 0.008 |
| 700 | 0.743 | 0.751 | 0.941 | 0.910 | 0.934 | 0.935 | 0.959 | 0.985 | 0.004 |
| 710 | 0.730 | 0.739 | 0.938 | 0.907 | 0.931 | 0.932 | 0.957 | 0.984 | 0.002 |
| 720 | 0.719 | 0.727 | 0.936 | 0.904 | 0.929 | 0.930 | 0.956 | 0.983 | 0.001 |
| 730 | 0.707 | 0.716 | 0.933 | 0.901 | 0.926 | 0.928 | 0.954 | 0.983 | 0.001 |
| 740 | 0.696 | 0.705 | 0.930 | 0.899 | 0.924 | 0.926 | 0.952 | 0.982 | 0.000 |
| 750 | 0.685 | 0.695 | 0.928 | 0.897 | 0.921 | 0.924 | 0.951 | 0.981 | 0.000 |
| 760 | 0.675 | 0.685 | 0.926 | 0.894 | 0.919 | 0.922 | 0.949 | 0.981 | 0.000 |
| 770 | 0.665 | 0.675 | 0.924 | 0.892 | 0.917 | 0.920 | 0.948 | 0.980 | 0.000 |
| 780 | 0.656 | 0.665 | 0.921 | 0.890 | 0.915 | 0.918 | 0.946 | 0.980 | 0.000 |

TABLE 3

| | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|
| Linear index | 1.87 | 1.75 | 1.97 | 4.16 | 2.91 | 3.37 | 2.17 |
| ReP2 (400)/ ReP2 (700) | 1.99 | 1.91 | 1.19 | 1.51 | 1.28 | 1.30 | 1.13 |
| ReP1 (550) min (nm) | 267.5 | 277.5 | 847.5 | 387.5 | 617.5 | 377.5 | 767.5 |
| ReP2 (550) min (nm) | 130 | 140 | 710 | 250 | 480 | 240 | 630 |
| Minimum reflectance Y value (%) | 0.03 | 0.03 | 0.02 | 0.19 | 0.10 | 0.34 | 0.20 |
| Displacement index | 0.16 | 0.12 | 0.14 | 1.06 | 0.58 | 2.21 | 1.46 |

As is evident from the results in Table 3, in Example 1 to Example 3, where the linear index of the phase difference plate P2 was less than 2.90, the deviation from the ideal distribution was significantly small and, as a result, the minimum reflectance Y value was also significantly small. Further, in Example 1 and Example 2, where ReP2(400)/ReP2(700) was 1.50 or more, the optimum value of ReP2 (550) was as small as approximately that of the ¼ wavelength plate. The phase difference plate having such a phase difference value can be made with a reduced thickness, can be easily produced, and therefore can be usefully employed.

Example 4

Simulation was conducted for evaluating the performance of the phase difference plate obtained in Example 1 when it was used as a film for improving sunglass-readability in a liquid crystal display device.

When the liquid crystal display device is viewed by a user wearing polarized sunglasses, visibility of the display screen may change depending on an angle formed by the liquid crystal display device and the sunglasses. The sunglass-readability refers to performance of the display device which allows a user to recognize a uniform image at a variety of angles with little change in the visibility.

The simulation was performed by setting a model shown in FIG. 1 using a simulation software "LCD Master" manufactured by Shintec Inc. As shown in FIG. 1, a simulation model 10 includes a liquid crystal display device 110 and sunglasses 120, and the liquid crystal display device 110 includes a phase difference plate 110P1, a phase difference plate 110P2, and a panel 111 in the order from the viewing side. In the model 10, the sunglasses 120, the phase difference plate 110P1, the phase difference plate 110P2, and the panel 111 are disposed in parallel.

In the model 10, the sunglasses 120 are an ideal polarizing film having the absorption axis in a direction of an arrow A 120.

In the model 10, as the panel 111, a commercially available liquid crystal display device (product name "iPad Air", manufactured by Apple Inc.) was used, and spectra obtained by displaying white image on the display surface were subjected to the simulation. The panel 111 includes a linear polarizer having the absorption axis in a direction of an arrow A 111 on the viewing side of the panel 111, and thus light discharged from the panel 111 is linearly polarized light. Broken lines B110P1 and B110P2 represent directions at which the arrow A 111 direction is projected on the phase difference plates 110P1 and 110P2, respectively. θP1 represents an angle formed by the broken line B110P1 and a slow axis direction A110P1 of the phase difference plate P1, while θP2 represents an angle formed by the broken line B110P2 and a slow axis direction A110P2 of the phase difference plate P2. θP1 was set to 45° and θP2 was set to 135°.

In the simulation, a situation in which a user viewed the liquid crystal display device 110 via the sunglasses 120 was assumed. The viewing direction was set to a direction having a polar angle of 0° (a direction shown by a broken line B120) with respect to the display surface of the liquid crystal display device 110. L*, a*, and b* of light discharged from the liquid crystal display device 110 and passed through the sunglasses 120 were each calculated when the liquid crystal display device 110 is rotated about the broken line B120 as an axis such that an azimuth angle (an angle formed by the absorption axis A111 of the panel 111 and the absorption axis A120 of the sunglasses 120) was changed in increments of 5° in a range of 0° to 360, while the position of the sunglasses 120 is fixed. Subsequently, L0*, a0*, and b0* of light discharged from the liquid crystal display device 110 in a case without the existence the sunglasses 120 were calculated. A value of $\Delta E^* (=\sqrt{((L^*-L0^*)^2+(a^*-a0^*)^2+(b^*-b0^*)^2)})$ was calculated in each direction, and a difference between the maximum value and the minimum value of the values thus obtained was calculated as ΔE*(Max–Min).

Under the premise that RePs(550) took value of 137.5 nm, studies were conducted by variously changing the thickness of the phase difference plate P1 and the phase difference plate P2. Of these, ReP1(550) and ReP2(550) minimizing ΔE*(Max–Min), as well as ΔE*(Max–Min) in this case, were obtained. The results are shown in Table 5. The smaller value of ΔE*(Max–Min) is indicative of less changes in a luminance and a color tone and less azimuth angle dependency of the sunglasses, and thus indicative of higher sunglass-readability.

Example 5

(5-1. Phase Difference Plate 2)

A phase difference plate P2 was obtained, and values of the linear index, ReP2(400)/ReP2(700), and Re(2)/Re(550) at each wavelength were obtained in the phase difference plate P2 by the same operation as that of (1-1) to (1-5) of Example 1 except for the following change. The results are shown in Table 4 and Table 5.

In the preparation of the liquid crystal composition in (1-1), a mixture of the compound LC1 and a compound LC4 was used instead of the compound LC1 as the liquid crystal compound of (1a). The weight ratio of the compound LC1 and the compound LC4 was set to 80:20.

(5-2. Evaluation of Sunglass-Readability by Simulation)

The simulation was performed by the same method as that in Example 4 using as the phase difference plate P2 the one obtained in (5-1) instead of the one obtained in (1-4) in Example 1 to calculate ΔE*(Max–Min). The result is shown in Table 5.

Example 6

(6-1. Phase Difference Plate 2)

A phase difference plate P2 was obtained and values of the linear index, ReP2(400)/ReP2(700), and Re(2)/Re(550) at each wavelength were obtained in the phase difference plate P2 by the same operation as that of (1-1) to (1-5) of Example 1 except for the following change. The results are shown in Table 4 and Table 5.

In the preparation of the liquid crystal composition in (1-1), a mixture of the compound LC1 and the compound LC4 was used instead of the compound LC1 as the liquid crystal compound of (1a). The weight ratio of the compound LC1 and the compound LC4 was set to 60:40.

(6-2. Evaluation of Sunglass-Readability by Simulation)

The simulation was performed by the same method as that in Example 4 using as the phase difference plate P2 the one obtained in (6-1) instead of the one obtained in (1-4) in Example 1 to calculate ΔE*(Max–Min). The result is shown in Table 5.

Comparative Example 5

On the basis of the result obtained in Comparative Example 3, the simulation was performed by the same operation as that of Example 4 using as the phase difference plate P2 the one obtained in Comparative Example (C3-1) instead of the one obtained in (1-4) in Example 1 to calculate ΔE*(Max–Min). The result is shown in Table 5.

TABLE 4

| | ReP2 (λ)/Re (550) | |
|---|---|---|
| λ (nm) | Ex. 5 | Ex. 6 |
| 380 | 1.429 | 1.340 |
| 390 | 1.396 | 1.312 |
| 400 | 1.362 | 1.284 |
| 410 | 1.337 | 1.262 |
| 420 | 1.307 | 1.239 |
| 430 | 1.270 | 1.210 |
| 440 | 1.248 | 1.191 |
| 450 | 1.222 | 1.170 |
| 460 | 1.187 | 1.144 |
| 470 | 1.161 | 1.124 |
| 480 | 1.144 | 1.109 |
| 490 | 1.122 | 1.093 |
| 500 | 1.092 | 1.071 |
| 510 | 1.067 | 1.051 |
| 520 | 1.055 | 1.041 |
| 530 | 1.040 | 1.030 |
| 540 | 1.025 | 1.018 |
| 550 | 1.000 | 1.000 |
| 560 | 0.981 | 0.986 |
| 570 | 0.968 | 0.977 |
| 580 | 0.960 | 0.971 |
| 590 | 0.950 | 0.963 |
| 600 | 0.935 | 0.953 |
| 610 | 0.919 | 0.940 |
| 620 | 0.903 | 0.929 |
| 630 | 0.890 | 0.920 |
| 640 | 0.880 | 0.913 |

TABLE 4-continued

| | ReP2 (λ)/Re (550) | |
|---|---|---|
| λ (nm) | Ex. 5 | Ex. 6 |
| 650 | 0.873 | 0.908 |
| 660 | 0.869 | 0.904 |
| 670 | 0.859 | 0.897 |
| 680 | 0.848 | 0.889 |
| 690 | 0.835 | 0.880 |
| 700 | 0.824 | 0.872 |
| 710 | 0.813 | 0.864 |
| 720 | 0.804 | 0.857 |
| 730 | 0.797 | 0.852 |
| 740 | 0.792 | 0.849 |
| 750 | 0.786 | 0.844 |
| 760 | 0.782 | 0.841 |
| 770 | 0.776 | 0.837 |
| 780 | 0.768 | 0.830 |

TABLE 5

| | Ex. 4 | Ex. 5 | Ex. 6 | Comp. Ex. 5 |
|---|---|---|---|---|
| Linear index | 1.87 | 2.06 | 2.22 | 3.37 |
| ReP2 (400)/ReP2 (700) | 1.99 | 1.65 | 1.47 | 1.30 |
| ReP1 (550) (nm) | 241 | 282 | 330 | 330 |
| ReP2 (550) (nm) | 103 | 143 | 191 | 191 |
| ΔE* (Max-Min) | 0.371 | 0.318 | 0.398 | 3.215 |

As is evident from the result in Table 5, in Example 4 to Example 6, where the value of Re(400)/Re(700) is greater than 1.13 and the linear index of the phase difference plate P2 is less than 2.90, the phase difference plate capable of constituting the liquid crystal display device having high sunglass-readability can be constituted.

REFERENCE SIGN LIST

10 Simulation model
110 Liquid crystal display device
110P1 Phase difference plate
110P2 Phase difference plate
111 Panel
120 Sunglasses
A111 Absorption axis
A110P1 Slow axis
A110P2 Slow axis
A120 Absorption axis

The invention claimed is:

1. A multilayer phase difference plate comprising a phase difference plate P1 and a phase difference plate P2, wherein
an in-plane slow axis of the phase difference plate P1 is orthogonal to an in-plane slow axis of the phase difference plate P2,
the phase difference plate P2 is the phase difference plate comprising a layer of a liquid crystal material oriented in an in-plane direction,
an in-plane retardation ReP2(λ) at a wavelength λ nm of the phase difference plate P2 satisfies the following formulae (e1) and (e2):

$$\{Re2(400) - Re2(550)\}/\{Re2(550) - Re2(700)\} \leq 2.0 \quad \text{(e1), and}$$

$$Re2(400)/Re2(700) \geq 1.90 \quad \text{(e2),}$$

an in-plane retardation ReP1(λ) of the phase difference plate P1 at a wavelength λ nm and the in-plane retardation ReP2(2) of the phase difference plate P2 at the wavelength λ nm satisfy the following formulae (e4) and (e5):

$$ReP1(550) > ReP2(550) \quad \text{(e4), and}$$

$$ReP1(400)/ReP1(700) < ReP2(400)/ReP2(700) \quad \text{(e5).}$$

2. The multilayer phase difference plate according to claim 1, wherein the liquid crystal material comprises a polymer of a liquid crystal compound represented by the following formula (I):

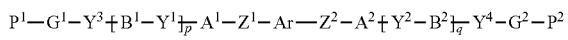

(I)

[in the formula (I),
Ar is a divalent aromatic hydrocarbon ring group having D as a substituent, or a divalent aromatic heterocyclic ring group having D as a substituent,
D is an organic group of 1 to 67 carbon atoms having one or more aromatic rings selected from the group consisting of an aromatic hydrocarbon ring and an aromatic heterocyclic ring,
$Z^1$ and $Z^2$ are each independently a single bond, —O—, —O—CH$_2$—, —CH$_2$—O—, —O—CH$_2$—CH$_2$—, —CH$_2$—CH$_2$—O—, —C(=O)—O—, —O—C(=O)—, —C(=O)—S—, —S—C(=O)—, —NR$^{21}$—C(=O)—, —C(=O)—NR$^{21}$—, —CF$_2$—O—, —O—CF$_2$—, —CH$_2$—CH$_2$—, —CF$_2$—CF$_2$—, —O—CH$_2$—CH$_2$—O—, —CH=CH—C(=O)—O—, —O—C(=O)—CH=CH—, —CH$_2$—C(=O)—O—, —O—C(=O)—CH$_2$—, —CH$_2$—O—C(=O)—, —C(=O)—O—CH$_2$—, —CH$_2$—CH$_2$—C(=O)—O—, —O—C(=O)—CH$_2$—CH$_2$—, —CH$_2$—CH$_2$—O—C(=O)—, —C(=O)—O—CH$_2$—CH$_2$—, —CH=CH—, —N=CH—, —CH=N—, —N=C(CH$_3$)—, —C(CH$_3$)=N—, —N=N—, or —C≡C—, and R$^{21}$ independently represents a hydrogen atom or an alkyl group of 1 to 6 carbon atoms,
$A^1$ and $A^2$, and $B^1$ and $B^2$ each independently represent a cyclic aliphatic group optionally having a substituent or an aromatic group optionally having a substituent,
$Y^1$ to $Y^4$ each independently represent a single bond, —O—, —C(=O)—, —C(=O)—O—, —O—C(=O)—, —NR$^{22}$—C(=O)—, —C(=O)—NR$^{22}$—, —O—C(=O)—O—, —NR$^{22}$—C(=O)—O—, —O—C(=O)—NR$^{22}$—, or —NR$^{22}$—C(=O)—NR$^{23}$, and R$^{22}$ and R$^{23}$ each independently represent a hydrogen atom or an alkyl group of 1 to 6 carbon atoms,
$G^1$ and $G^2$ are each independently any of organic groups that are an aliphatic hydrocarbon group of 1 to 20 carbon atoms and a group in which one or more methylene groups (—CH$_2$—) contained in an aliphatic hydrocarbon group of 3 to 20 carbon atoms are substituted by —O— or —C(=O)—, and hydrogen atoms in the organic groups of $G^1$ and $G^2$ may be substituted by an alkyl group of 1 to 5 carbon atoms, an alkoxy group of 1 to 5 carbon atoms, or a halogen atom,
P1 and P2 each independently represent a polymerizable group, and p and q are each independently 0 or 1].

3. The multilayer phase difference plate according to claim 1, wherein
the $\text{ReP1}(\lambda)$ satisfies the following formula (e6):

$$\text{ReP1}(400)/\text{ReP1}(700) < 1.10 \qquad \text{(e6)}.$$

4. The multilayer phase difference plate according to claim 1, wherein
the phase difference plate P1 is a stretched product of a film made of a resin containing an alicyclic structure-containing polymer.

5. The multilayer phase difference plate according to claim 1, wherein
the $\text{ReP1}(\lambda)$ and the $\text{ReP2}(\lambda)$ satisfy the following formula (e7):

$$90 \text{ nm} < \text{ReP1}(550) - \text{ReP2}(550) < 160 \text{ nm} \qquad \text{(e7)}.$$

6. The multilayer phase difference plate according to claim 1, wherein
the ReP1(2) and ReP2(2) satisfy the following formulae (e8) and (e9):

$$180 \text{ nm} \leq \text{ReP1}(550) \leq 350 \text{ nm} \qquad \text{(e8), and}$$

$$90 \text{ nm} \leq \text{ReP2}(550) \leq 160 \text{ nm} \qquad \text{(e9)}.$$

7. A polarizing plate comprising the multilayer phase difference plate according to claim 1, and a linear polarizer.

8. An image display device comprising the polarizing plate according to claim 7.

\* \* \* \* \*